(12) United States Patent
Jenkins et al.

(10) Patent No.: US 10,376,327 B2
(45) Date of Patent: Aug. 13, 2019

(54) COMPUTER PROGRAMS FOR VISUALIZATIONS USING IMAGE DATA AND PREDEFINED DATA OF SURGICAL TOOLS

(71) Applicant: MRI Interventions, Inc., Irvine, CA (US)

(72) Inventors: Kimble Jenkins, Memphis, TN (US); Peter Piferi, Orange, CA (US); Philip Bradley Hotte, Mississauga (CA); Pavel Farberov, Vaughan (CA); Timothy Neil Orr, North York (CA); Paul Arthur Geiger, Toronto (CA); David John Sayler, Portland, OR (US)

(73) Assignee: MRI Interventions, Inc., Irvine, CA (US)

( * ) Notice: Subject to any disclaimer, the term of this patent is extended or adjusted under 35 U.S.C. 154(b) by 483 days.

(21) Appl. No.: 15/067,615

(22) Filed: Mar. 11, 2016

(65) Prior Publication Data

US 2016/0256069 A1  Sep. 8, 2016

Related U.S. Application Data

(60) Continuation of application No. 13/610,338, filed on Sep. 11, 2012, now Pat. No. 9,314,305, which is a
(Continued)

(51) Int. Cl.
*A61B 5/00* (2006.01)
*A61B 34/00* (2016.01)
(Continued)

(52) U.S. Cl.
CPC ............ *A61B 34/74* (2016.02); *A61B 5/0042* (2013.01); *A61B 5/055* (2013.01); *A61B 5/7435* (2013.01);
(Continued)

(58) Field of Classification Search
CPC ...... A61B 5/055; A61B 5/7435; A61B 5/0042; A61B 5/0555; A61B 90/37; A61B 90/11;
(Continued)

(56) References Cited

U.S. PATENT DOCUMENTS 2,697,433 A   12/1954  Zehnder
4,051,845 A   10/1977  Collins
(Continued)

FOREIGN PATENT DOCUMENTS

DE   19625834   1/1998
DE   10029736   3/2002
(Continued)

OTHER PUBLICATIONS

Dorward et al., Accuracy of true frameless stereotaxy: in vivo measurement and laboratory phantom studies, J. Neurosurg., 1999, 90:160-168.
(Continued)

*Primary Examiner* — Peter Luong
(74) *Attorney, Agent, or Firm* — Myers Bigel, P.A.

(57) ABSTRACT

Circuits and computer program products onboard and/or adapted to communicate with an scanner that electronically recognize predefined physical characteristics of the at least one tool to automatically segment image data provided by the scanner whereby the at least one tool constitutes a point of interface with the system. The circuits and computer program products are configured to provide a User Interface that defines workflow progression for an image guided surgical procedure and allows a user to select steps in the workflow, and generate multi-dimensional visualizations using the predefined data of the at least one tool and data from images of the patient in substantially real time during the surgical procedure.

21 Claims, 40 Drawing Sheets

Related U.S. Application Data division of application No. 12/236,854, filed on Sep. 24, 2008, now Pat. No. 8,315,689, which is a continuation-in-part of application No. 12/134,412, filed on Jun. 6, 2008, now Pat. No. 8,175,677.

(60) Provisional application No. 60/974,821, filed on Sep. 24, 2007.

(51) Int. Cl.

| | | |
|---|---|---|
| *G01R 33/28* | (2006.01) | |
| *G01R 33/3415* | (2006.01) | |
| *A61B 90/96* | (2016.01) | |
| *A61B 90/11* | (2016.01) | |
| *A61B 34/10* | (2016.01) | |
| *A61B 90/00* | (2016.01) | |
| *A61B 5/055* | (2006.01) | |
| *A61B 17/00* | (2006.01) | |
| *A61B 17/34* | (2006.01) | |
| *G01R 33/54* | (2006.01) | |
| *A61B 90/10* | (2016.01) | |
| *A61B 90/14* | (2016.01) | |

(52) U.S. Cl.
CPC .............. *A61B 34/10* (2016.02); *A61B 34/25* (2016.02); *A61B 90/11* (2016.02); *A61B 90/37* (2016.02); *A61B 90/96* (2016.02); *G01R 33/286* (2013.01); *G01R 33/3415* (2013.01); *A61B 5/0555* (2013.01); *A61B 90/14* (2016.02); *A61B 90/361* (2016.02); *A61B 2017/00212* (2013.01); *A61B 2017/3407* (2013.01); *A61B 2017/3409* (2013.01); *A61B 2034/101* (2016.02); *A61B 2034/107* (2016.02); *A61B 2034/252* (2016.02); *A61B 2034/254* (2016.02); *A61B 2034/256* (2016.02); *A61B 2090/103* (2016.02); *A61B 2090/374* (2016.02); *A61B 2090/395* (2016.02); *A61B 2090/3933* (2016.02); *A61B 2090/3937* (2016.02); *A61B 2090/3954* (2016.02); *A61B 2090/3983* (2016.02); *G01R 33/546* (2013.01)

(58) Field of Classification Search
CPC ....... A61B 90/96; A61B 90/361; A61B 90/14; A61B 34/74; A61B 34/10; A61B 34/25; A61B 2034/252; A61B 2034/107; A61B 2034/256; A61B 2034/254; A61B 2034/101; A61B 2090/3954; A61B 2090/395; A61B 2090/3937; A61B 2090/374; A61B 2090/3933; A61B 2090/3983; A61B 2090/103; A61B 2017/3407; A61B 2017/00212; A61B 2017/3409; G01R 33/3415; G01R 33/286; G01R 33/546

See application file for complete search history.

(56) References Cited

U.S. PATENT DOCUMENTS

| | | | |
|---|---|---|---|
| 4,209,258 A | 6/1980 | Oakes | |
| 4,276,697 A | 7/1981 | Drake et al. | |
| 4,319,136 A | 3/1982 | Jinkins | |
| 4,386,602 A | 6/1983 | Sheldon et al. | |
| 4,838,265 A | 6/1989 | Cosman et al. | |
| 4,922,915 A | 5/1990 | Arnold et al. | |
| 5,052,035 A | 9/1991 | Krupnick | |
| 5,125,888 A | 5/1992 | Howard et al. | |
| 5,154,179 A | 10/1992 | Ratner | |
| 5,154,723 A | 10/1992 | Kubota et al. | |
| 5,201,742 A | 4/1993 | Hasson | |
| 5,260,985 A | 11/1993 | Mosby | |
| 5,342,356 A | 8/1994 | Ellman et al. | |
| 5,427,099 A | 6/1995 | Adams | |
| 5,469,847 A | 11/1995 | Zinreich et al. | |
| 5,638,819 A | 6/1997 | Manwaring et al. | |
| 5,655,084 A | 8/1997 | Pinsky et al. | |
| 5,695,501 A | 12/1997 | Carol et al. | |
| 5,697,958 A | 12/1997 | Paul et al. | |
| 5,699,801 A | 12/1997 | Atalar et al. | |
| 5,707,335 A | 1/1998 | Howard et al. | |
| 5,728,079 A | 3/1998 | Webber et al. | |
| 5,743,899 A | 4/1998 | Zinreich | |
| 5,776,144 A | 7/1998 | Leysieffer et al. | |
| 5,779,694 A | 7/1998 | Howard et al. | |
| 5,800,353 A | 9/1998 | McLaurin | |
| 5,817,017 A | 10/1998 | Young et al. | |
| 5,855,582 A | 1/1999 | Gildenberg | |
| 5,873,822 A | 2/1999 | Ferre et al. | |
| 5,928,145 A | 7/1999 | Ocali et al. | |
| 5,943,433 A | 8/1999 | Avinash | |
| 5,961,455 A | 10/1999 | Daum et al. | |
| 5,971,984 A | 10/1999 | Taylor et al. | |
| 5,971,997 A | 10/1999 | Guthrie et al. | |
| 5,993,463 A | 11/1999 | Truwit | |
| 6,006,126 A | 12/1999 | Cosman | |
| 6,050,992 A | 4/2000 | Nichols | |
| 6,052,477 A | 4/2000 | Wang et al. | |
| 6,119,032 A | 9/2000 | Martin et al. | |
| 6,159,497 A | 12/2000 | LaPrade et al. | |
| 6,167,292 A | 12/2000 | Bandano et al. | |
| 6,167,311 A | 12/2000 | Rezai | |
| 6,195,577 B1 | 2/2001 | Truwit et al. | |
| 6,206,890 B1 | 3/2001 | Truwit | |
| 6,216,030 B1 | 4/2001 | Howard et al. | |
| 6,263,229 B1 | 7/2001 | Atalar et al. | |
| 6,264,607 B1 | 7/2001 | Goll et al. | |
| 6,267,769 B1 | 7/2001 | Truwit et al. | |
| 6,267,770 B1 | 7/2001 | Truwit | |
| 6,273,896 B1 | 8/2001 | Franck et al. | |
| 6,282,437 B1 | 8/2001 | Franck et al. | |
| 6,284,971 B1 | 9/2001 | Atalar et al. | |
| 6,298,262 B1 | 10/2001 | Franck et al. | |
| 6,351,573 B1 | 2/2002 | Schneider | |
| 6,351,662 B1 | 2/2002 | Franck et al. | |
| 6,356,786 B1 | 3/2002 | Rezai et al. | |
| 6,360,116 B1 | 3/2002 | Jackson et al. | |
| 6,368,329 B1 | 4/2002 | Truwit | |
| 6,405,079 B1 | 6/2002 | Ansarinia | |
| 6,419,680 B1 | 7/2002 | Cosman et al. | |
| 6,438,423 B1 | 8/2002 | Rezai et al. | |
| 6,526,318 B1 | 2/2003 | Ansarinia | |
| 6,529,765 B1 | 3/2003 | Franck et al. | |
| 6,539,263 B1 | 3/2003 | Schiff et al. | |
| 6,546,277 B1 | 4/2003 | Franck et al. | |
| 6,574,497 B1 | 6/2003 | Pacetti | |
| 6,584,351 B1 | 6/2003 | Ekwall | |
| 6,591,128 B1 | 7/2003 | Wu et al. | |
| 6,606,513 B2 | 8/2003 | Lardo et al. | |
| 6,609,030 B1 | 8/2003 | Rezai et al. | |
| 6,628,980 B2 | 9/2003 | Atalar et al. | |
| 6,675,033 B1 | 1/2004 | Lardo et al. | |
| 6,701,176 B1 | 3/2004 | Halperin et al. | |
| 6,708,064 B2 | 3/2004 | Rezai | |
| 6,725,080 B2 | 4/2004 | Melkent et al. | |
| 6,725,092 B2 | 4/2004 | MacDonald et al. | |
| 6,752,812 B1 | 6/2004 | Truwit | |
| 6,772,000 B2 | 8/2004 | Talpade | |
| 6,782,288 B2 | 8/2004 | Truwit et al. | |
| 6,902,569 B2 | 6/2005 | Parmer et al. | |
| 6,904,307 B2 | 6/2005 | Karmarkar et al. | |
| 6,920,347 B2 | 7/2005 | Simon et al. | |
| 6,989,015 B2 | 1/2006 | Daum et al. | |
| 7,022,082 B2 | 4/2006 | Sonek | |
| 7,155,316 B2 | 12/2006 | Sutherland et al. | |
| 7,167,760 B2 | 1/2007 | Dawant et al. | |
| 7,174,219 B2 | 2/2007 | Wahlstrand et al. | |
| 7,203,551 B2 | 4/2007 | Houben et al. | |

(56) References Cited

U.S. PATENT DOCUMENTS

| | | |
|---|---|---|
| 7,204,840 B2 | 4/2007 | Skakoon et al. |
| 7,212,611 B2 | 5/2007 | De Godzinsky |
| 7,217,276 B2 | 5/2007 | Henderson et al. |
| 7,235,084 B2 | 6/2007 | Skakoon et al. |
| 7,241,283 B2 | 7/2007 | Putz |
| 7,313,430 B2 | 12/2007 | Urquhart et al. |
| 7,559,935 B2 | 7/2009 | Solar et al. |
| 7,561,906 B2 | 7/2009 | Atalar et al. |
| 7,602,190 B2 | 10/2009 | Piferi et al. |
| 7,636,596 B2 | 12/2009 | Solar |
| 7,637,915 B2 | 12/2009 | Parmer et al. |
| 7,658,879 B2 | 2/2010 | Solar |
| 7,660,621 B2 | 2/2010 | Skakoon et al. |
| 7,697,972 B2 | 4/2010 | Verard et al. |
| 7,699,854 B2 | 4/2010 | Mazzocchi et al. |
| 7,792,568 B2 | 9/2010 | Zhong et al. |
| 7,794,469 B2 | 9/2010 | Kao et al. |
| 7,896,889 B2 | 3/2011 | Mazzocchi et al. |
| 7,955,385 B2 | 6/2011 | Crittenden |
| 8,128,577 B2 | 3/2012 | Viola |
| 8,175,677 B2 | 5/2012 | Sayler et al. |
| 8,195,272 B2 | 6/2012 | Piferi et al. |
| 8,374,677 B2 | 2/2013 | Piferi et al. |
| 2001/0004676 A1 | 6/2001 | Ouchi |
| 2001/0047126 A1 | 11/2001 | Nagai et al. |
| 2001/0053879 A1 | 12/2001 | Mills et al. |
| 2001/0056232 A1 | 12/2001 | Lardo |
| 2002/0019641 A1 | 2/2002 | Truwit |
| 2002/0049451 A1 | 4/2002 | Parmer et al. |
| 2002/0052610 A1 | 5/2002 | Skakoon et al. |
| 2002/0082495 A1 | 6/2002 | Biswal et al. |
| 2003/0009095 A1 | 1/2003 | Skarda |
| 2003/0028095 A1 | 2/2003 | Tulley et al. |
| 2003/0050557 A1 | 3/2003 | Susil et al. |
| 2003/0055436 A1 | 3/2003 | Daum et al. |
| 2003/0055449 A1 | 3/2003 | Lee et al. |
| 2003/0073901 A1 | 4/2003 | Simon et al. |
| 2003/0097116 A1 | 5/2003 | Putz |
| 2003/0120143 A1 | 6/2003 | Franklin et al. |
| 2003/0205233 A1 | 11/2003 | Aboul-Hosn et al. |
| 2004/0002642 A1 | 1/2004 | Dekel et al. |
| 2004/0024308 A1 | 2/2004 | Wickline et al. |
| 2004/0044279 A1 | 3/2004 | Lewin et al. |
| 2004/0046557 A1 | 3/2004 | Karmarkar et al. |
| 2004/0064148 A1 | 4/2004 | Daum et al. |
| 2004/0092810 A1 | 5/2004 | Daum et al. |
| 2004/0167393 A1 | 8/2004 | Solar et al. |
| 2004/0167542 A1 | 8/2004 | Solar et al. |
| 2004/0228796 A1 | 11/2004 | Talpade |
| 2005/0004453 A1 | 1/2005 | Tearney et al. |
| 2005/0049486 A1 | 3/2005 | Urquhart et al. |
| 2005/0058363 A1 | 3/2005 | Florent et al. |
| 2005/0070781 A1 | 3/2005 | Dawant et al. |
| 2005/0131522 A1 | 6/2005 | Stinson et al. |
| 2005/0165301 A1 | 7/2005 | Smith et al. |
| 2005/0171425 A1 | 8/2005 | Burke |
| 2005/0193609 A1 | 9/2005 | Schwartz |
| 2005/0203384 A1 | 9/2005 | Sati et al. |
| 2005/0255046 A1 | 11/2005 | Zhong et al. |
| 2006/0173283 A1 | 8/2006 | Axelsson et al. |
| 2006/0229641 A1 | 10/2006 | Gupta et al. |
| 2006/0241368 A1 | 10/2006 | Fichtinger et al. |
| 2006/0241400 A1 | 10/2006 | Bucholz |
| 2008/0039709 A1 | 2/2008 | Karmarkar |
| 2009/0118610 A1 | 5/2009 | Karmarkar et al. |

FOREIGN PATENT DOCUMENTS

| | | |
|---|---|---|
| DE | 10029737 | 5/2003 |
| EP | 1524626 | 4/2005 |
| JP | 2001161660 | 6/2001 |
| JP | 2002052642 | 2/2002 |
| JP | 2002524191 | 8/2002 |
| JP | 2003210433 | 7/2003 |
| JP | 2005084309 | 3/2005 |
| JP | 2005137498 | 6/2005 |
| JP | 2005334645 | 12/2005 |
| WO | WO 1998/52064 | 11/1998 |
| WO | WO 1999/034732 | 7/1999 |
| WO | WO 2003/102614 | 12/2003 |
| WO | WO 2004/029782 | 4/2004 |
| WO | WO 2004/058086 | 6/2004 |
| WO | WO 2006/014966 | 2/2006 |
| WO | WO 2006/081409 | 8/2006 |
| WO | WO 2006/099475 | 9/2006 |
| WO | WO 2007/032341 | 3/2007 |
| WO | WO 2007/033206 | 3/2007 |
| WO | WO 2007/047966 | 4/2007 |
| WO | WO 2007/064739 | 6/2007 |
| WO | WO 2007/106558 | 9/2007 |

OTHER PUBLICATIONS

Fitzpatrick, et al., Accuracy of Customized Miniature Stereotactic Platforms, abstract only, Stereotactic and Functional Neurosurgery, vol. 83, No. 1, 2005, http://content.karger.com, 2 sheets.

Francel, Nexframe System, Bilateral Activa Lead Delivery to STN Using NEXFRAME, Oklahoma University Presbyterian Hospital, Image-Guided Neurolgics, 2004.

Franck, et al., STarFix™, Power Point presentation, www.tgt.vanderbilt.edu/reu2/REU2002/chris.ppt, 2002, 19 Sheets.

Grimson et al., An automatic registration method for frameless stereotaxy, image guided surgery, and visualization, IEEE Tran on Medical Imaging, Apr. 1996, 129-140.

Hall et al., Brian biopsy sampling by using prospective stereotaxis and a trajectory guide, J. Neurosurg., 2001, 94:67-71.

International Search Report and Written Opinion for corresponding PCT application No. PCT/US2008/011050, dated Jun. 24, 2009.

Invitation to Pay Additional Fees and Partial International Search for PCT application PCT/US2008/007169, dated Nov. 19, 2008.

Invitation to Pay Additional Fees and Partial International Search for corresponding PCT application PCT/US2008/011050, dated Mar. 10, 2009.

Jorgensen, Erik, Brain Image Analsis Team Joins SCI Institute, http://www.sci.utah.edu/stories/2007/Gerig_NeuroimageAnalysis.html, (2007), 3 Pages.

Lin, Fa-Hsuan et al., A Wavelet-Based Approximation of Surface Coil Sensitivity Profiles for Correction of Image Intensity Inhomogeneity and Parallel Imaging Reconstruction, Human Brain Mapping, vol. 19, No. 2, pp. 96-111, (2003).

Liu et al., Remotely-Controlled Approach for Stereotactic Neurobiopsy, Computer Aided Surgery, 2002, 7:237-247.

Martin et al., Placement of Deep Brain Stimulator Electrodes Using Real-Time High-Field Interventional Magnetic Resonance Imaging, Magnetic Resonance in Medicine, 2005, 54:1107-1114.

Sauser, Brittany, A 3-D View of the Brain, http://www.technologyreview.com/Biotech/19140, Aug. 6, 2007, 3 Pages.

Singh, Manbir and Moriel NessAiver, Accurate Intensity Correction for Endorectal Surface Coil MR Imaging of the Prostate, IEEE Transactions on Nuclear Science, vol. 40, No. 4, pp. 1307-1309, (1993).

Smith et al., The NEUROSTATION—A Highly Accurate, Minimally Invasive Solution to Frameless Stereotactic Neurosurgery, Computerized Medical Imaging and Graphics, 1994, 247-256, 18(4).

STarFix™—Dr. Joel Franck and FHC engineer Ron Franklin—creators, 2002, www.tgt.vanderbilt.edu/reu2/REU2002/chris.ppt.

Truwit et al., Prospective Stereotaxy: A Novel Method of Trajectory Alignment Using Real-Time Image Guidance, J. Magn. Reson. Imag., 2001, 13:452-457.

Willems, et al., Frameless Stereotaxy, VHL Family Alliance, http://www.vhl.org/newsletter/vhl2000/00aefrst.htm, Mar. 2000, 3 Sheets.

Wirtz et al., Image-Guided Neurosurgery with Intraoperative MRI: Update of Frameless Stereotaxy and Radicality Control, Sterotact Funct Neurosurg 1997, 68:39-43.

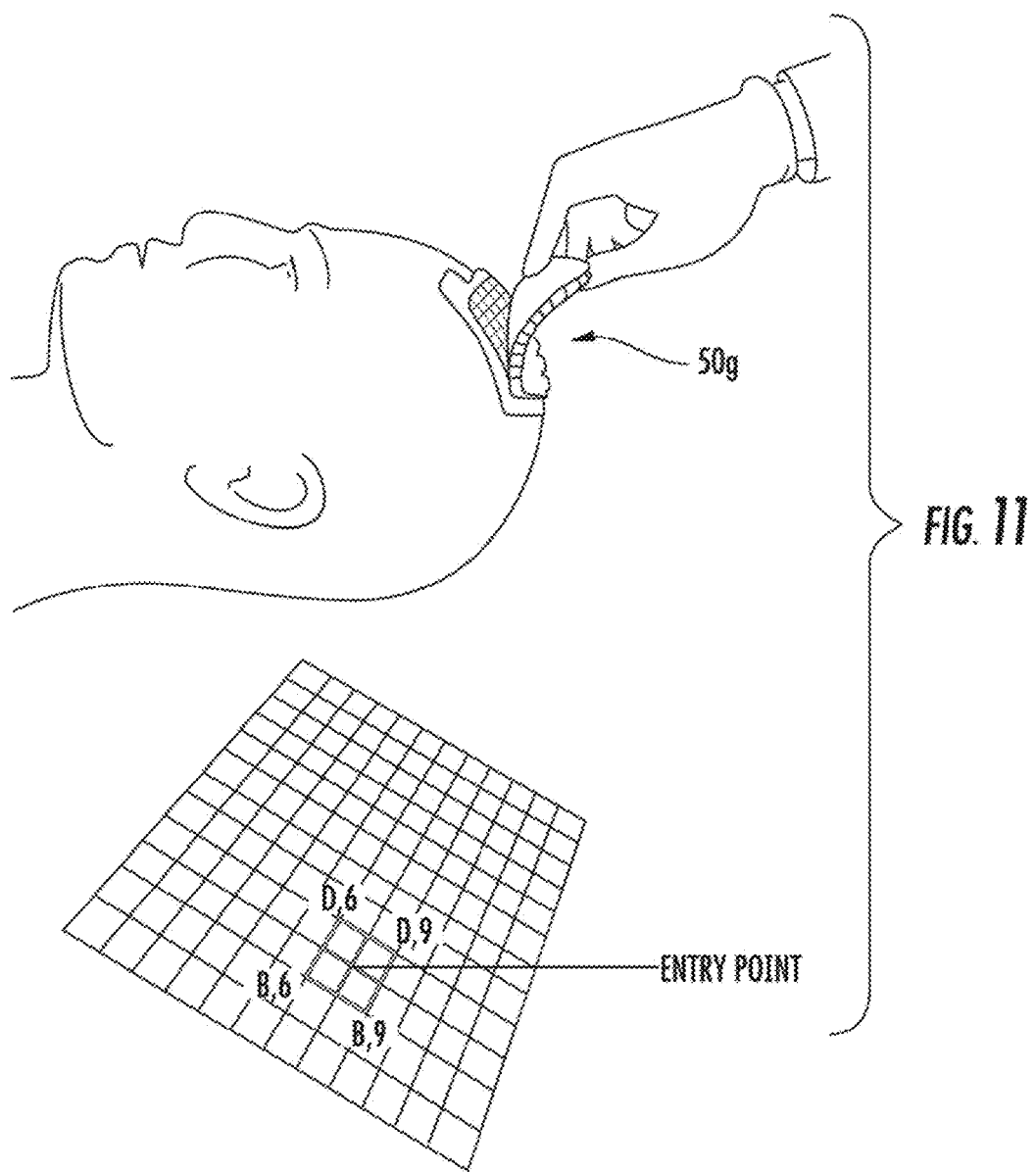

AN EXAMPLE HISTOGRAM, WITH A NOISE REGION

EXAMPLE OF AN INITIAL DISTANCE IMAGE

THE RESULT OF SEARCHING FOR THE GRID IN THE INITIAL DISTANCE IMAGE

THE RESULT OF SEARCHING FOR THE GRID IN THE OPTIMAL DISTANCE IMAGE, WITH SMALL STEP SIZES

THE RESULT OF DEFORMING THE GRID TO FIT THE HEAD SURFACE, AND INTERPOLATING THE GRID CELLS TO FIND THE VERTICES

AN EXAMPLE HISTOGRAM, WITH A NOISE REGION

CROSS SECTION OF AN IMAGED FRAME-MARKER

RESULT OF FITTING A CIRCLE TO THE EDGE MASK

FIG. 38

COMPUTER PROGRAMS FOR VISUALIZATIONS USING IMAGE DATA AND PREDEFINED DATA OF SURGICAL TOOLS

RELATED APPLICATIONS

This application is a continuation application (an indirect divisional application) of U.S. patent application Ser. No. 13/610,338, filed Sep. 11, 2012, which is a first divisional application of U.S. patent application Ser. No. 12/236,854, filed Sep. 24, 2008, which is a continuation-in-part of U.S. application Ser. No. 12/134,412, filed Jun. 6, 2008, which issued on May 8, 2012 as U.S. Pat. No. 8,175,677, and which also claims priority to U.S. Provisional Application Ser. No. 60/974,821, filed Sep. 24, 2007, the contents of which are hereby incorporated by reference as if recited in full herein.

FIELD OF THE INVENTION

The present invention relates to MRI-guided diagnostic or interventional systems that may be particularly suitable for placement/localization of interventional medical devices and/or therapies in the body. Embodiments of the present invention may be particularly suitable for placing neuromodulation leads, such as Deep Brain Stimulation ("DBS") leads, placing implantable parasympathetic or sympathetic nerve chain leads and/or CNS stimulation leads and/or for delivering therapies to target internal locations in the body including atrial fibrillation (AFIB) therapies.

BACKGROUND OF THE INVENTION

Deep Brain Stimulation (DBS) is becoming an acceptable therapeutic modality in neurosurgical treatment of patients suffering from chronic pain, Parkinson's disease or seizure, and other medical conditions. Other electro-stimulation therapies have also been carried out or proposed using internal stimulation of the sympathetic nerve chain and/or spinal cord, etc.

One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

It is believed that the clinical outcome of certain medical procedures, particularly those using DBS, may depend on the precise location of the electrodes that are in contact with the tissue of interest. For example, to treat Parkinson's tremor, DBS stimulation leads are conventionally implanted during a stereotactic surgery, based on pre-operative MRI and CT images. These procedures can be long in duration and may have reduced efficacy as it has been reported that, in about 30% of the patients implanted with these devices, the clinical efficacy of the device/procedure is less than optimum.

SUMMARY OF EMBODIMENTS OF THE INVENTION

Some embodiments of the present invention are directed to MRI-guided systems that can generate substantially real time patient-specific visualizations of the patient and one or more surgical tools in logical space and provide feedback to a clinician to improve the speed and/or reliability of an intrabody procedure.

The visualizations can be based (in-part) on predefined data of the tool(s) which define a point of interface for the system (e.g., software) based on predefined characteristics of the tool(s), e.g., dimensions, shape or configuration and/or known rotational, translational and/or other functional and/or dynamic behavior of one or more surgical tools. The visualizations can include patient function data (e.g., fMRI data, electrical activity, active regions of a brain during a defined stimulation, fiber tracks, and the like).

The system can be configured to interrogate and segment image data to locate fiducial markers and generate successive visualizations of the patient's anatomical structure and tool(s) using MRI image data and a priori data of the tool(s) to provide (substantially real-time) visualizations of the patient.

Some embodiments are directed to MRI-guided surgical systems. The systems include: (a) at least one MRI-compatible surgical tool; (b) a circuit adapted to communicate with an MRI scanner; and (c) at least one display in communication with the circuit. The circuit electronically recognizes predefined physical characteristics of the at least one tool to automatically segment MR image data provided by the MRI scanner whereby the at least one tool constitutes a point of interface with the system. The circuit is configured to provide a User Interface that defines workflow progression for an MRI-guided surgical procedure and allows a user to select steps in the workflow, and wherein the circuit is configured to generate multi-dimensional visualizations using the predefined data of the at least one tool and data from MRI images of the patient in substantially real time during the surgical procedure.

Other embodiments are directed to methods for performing an MRI-guided surgical procedure. The methods include: (a) defining dimensional and/or functional data of at least one MRI compatible surgical tool; (b) obtaining MRI image data of the patient; (c) electronically segmenting the MRI image data to identify known fiducial markers on the at least one tool based on the defining step; (d) generating visualizations of the at least one tool registered to patient anatomical structure; (e) electronically generating directions on adjustments for a pitch, roll or X-Y actuator to adjust a trajectory of a trajectory guide; and (f) guiding the tool to a location in the patient using patient MRI image data, the directions for adjustment and the visualizations thereby facilitating an MRI-guided surgical procedure.

Still other embodiments are directed to computer program products for facilitating an MRI-guided surgical procedure. The computer program product includes a computer readable storage medium having computer readable program code embodied in the medium. The computer-readable program code includes: (a) computer readable program code that comprises predefined physical data of a plurality of different surgical tools; (b) computer readable program code that communicates with an MRI scanner to obtain MRI image data of a patient; and (c) computer readable program code that generates visualizations of the patient using data from the tools and the image data of the patient in substantially real-time.

Yet other embodiments are directed to MRI-guided interventional deep brain systems. The systems include: (a) an MRI Scanner; (b) a clinician workstation with a circuit and a display, the workstation in communication with the MRI Scanner; (c) at least one flexible patch with a grid thereon configured to releasably attach to a patient's skull; and (d) at least one trajectory guide attachable to a skull of a patient. The guide has a base with an aperture configured to reside over a burr hole formed in a patient's skull. The base aperture provides a mechanical center of rotation for a pivot axis associated with the trajectory guide, the base having a plurality of fiducial markers spaced apart about the base aperture. The circuit comprises physical data regarding the patch and is configured to interrogate patient imaging data provided by the MRI Scanner and segment the image data to define a burr hole location that intersects the patch with a desired intrabrain trajectory. The circuit comprises tool-specific data of the trajectory guide and is configured to interrogate patient imaging data provided by the MRI Scanner and interactively generate visualizations of the patient's brain and the trajectory guide to the display.

In some embodiments, the circuit is configured to provide a default trajectory for the trajectory guide on the display that extends through a center location of the grid patch.

Embodiments of the invention can provide output to a user such as one or more of: (a) electronic generated warnings to alert an improper planned trajectory for a trajectory guide; (b) warnings regarding a physical interference with a planned projected trajectory associated with the MRI bore size and (isocenter) position (and optionally, patient head size and angle(s) or configuration of a surgical tool); (c) electronic instructions on what grid entry location to use to obtain a desired trajectory or entry point into the patient brain; (d) calculate and provide suggested physical adjustments to actuators to obtain a desired trajectory orientation and generate instructions on what adjustments to make to X, Y, pitch and roll adjustment mechanisms (e.g., rotate X button or dial left or right, potentially with a number of rotations or increments and the like) associated with the trajectory guide to obtain the desired trajectory; and (e) generate electronic data of electrode offset values for stimulation leads in the brain to define where the electrodes are anatomically positioned whereby pulse generator programming may be accelerated over conventional techniques.

Some embodiments of the present invention can provide visualizations to allow more precise control, delivery, and/or feedback of a therapy so that the therapy or a tool associated therewith can be more precisely placed, delivered, confirmed and visualized.

These and other embodiments will be described further below.

BRIEF DESCRIPTION OF THE DRAWINGS

FIG. 11 is a schematic illustration of a marking grid patch and associated screen display of coordinates of a surgical entry site according to embodiments of the present invention.

FIG. 14B illustrates UI selectable steps for a selected workflow group according to some embodiments of the present invention.

FIGS. 16-19 and 22-38 are screen shots of exemplary displays of different workflow groups and/or steps associated with a User Interface provided to a user to facilitate an MRI-guided procedure.

DETAILED DESCRIPTION OF EMBODIMENTS OF THE INVENTION

Figure 1:
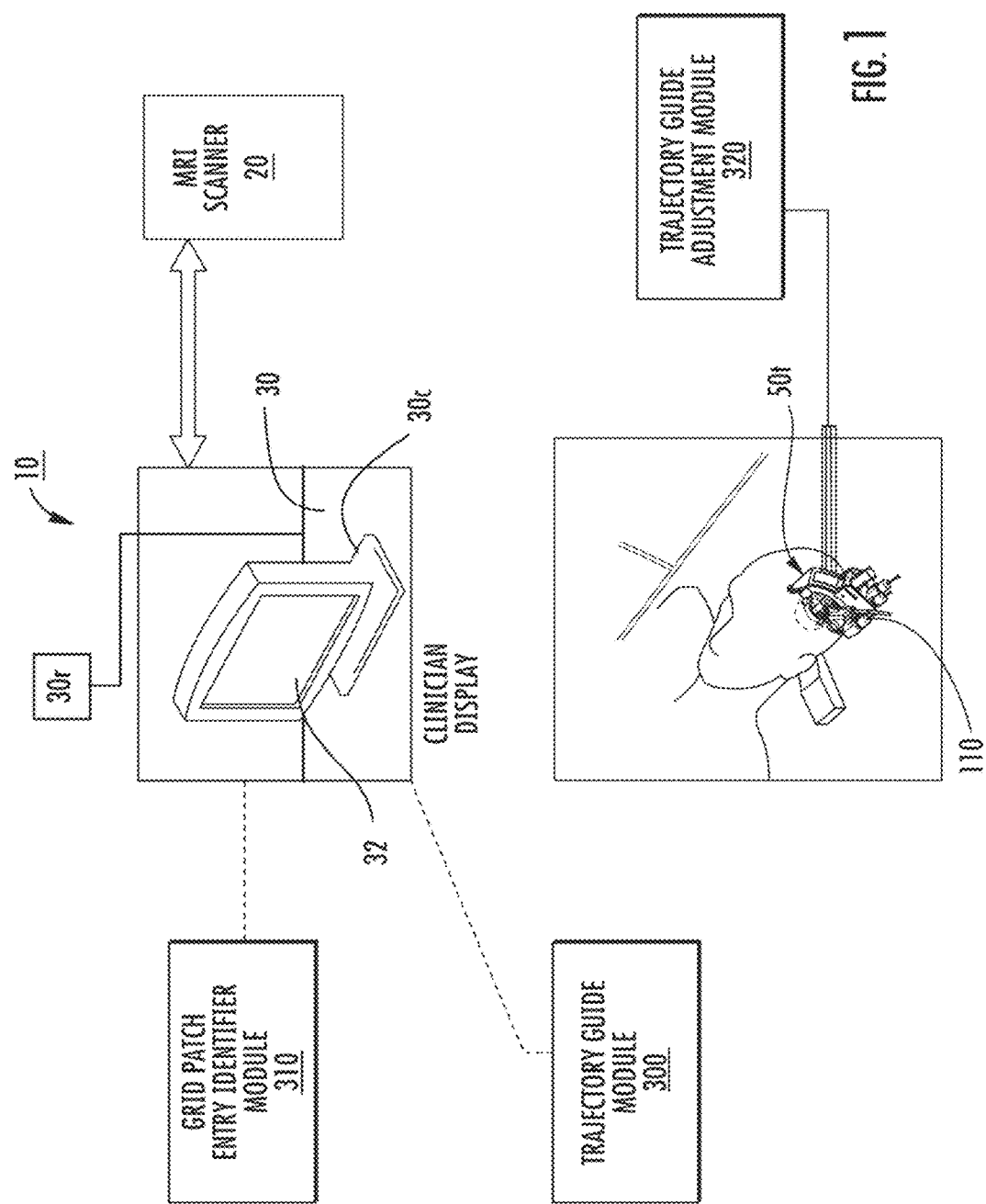
FIG. 1 is a schematic illustration of a MRI-guided surgical system according to some embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "electroanatomical visualization" or refers to a visualization or map of the anatomical structure, e.g., brain or heart, typically a volumetric, 3-D map or 4-D map, that illustrates or shows electrical activity of tissue correlated to anatomical and/or coordinate spatial position. The visualization can be in color and color-coded to provide an easy to understand map or image with different measures or gradients of activity in different colors and/or intensities. The term "color-coded" means that certain features electrical activity or other output are shown with defined colors of different color and/or intensity to visually accentuate different tissue, different and similar electrical activity or potential in tissue and/or to show abnormalities or lesions in tissue versus normal or non-lesion tissue. In some embodiments, the systems can be configured to allow a clinician to increase or decrease the intensity or change a color of certain tissue types or electrical outputs, e.g., in high-contrast color and/or intensity, darker opacity or the like.

The actual visualization can be shown on a screen or display so that the map and/or anatomical or tool structure is in a flat 2-D view and/or in 2-D what appears to be 3-D volumetric images with data representing features or electrical output with different visual characteristics such as with differing intensity, opacity, color, texture and the like. A 4-D map illustrates time-dependent activity, such as electrical activity or blood flow movement.

The systems are configured to operate based on known physical characteristics of one or more surgical tools such that the hardware is a point of interface for the circuit or software. The systems can communicate with databases that define dimensions, configurations or shapes and spacing of components on the tool(s). The defined physical data can be obtained from a CAD model of a tool. The physical characteristics can include dimensions or other physical features or attributes and may also include relative changes in position of certain components or features upon a change in position of a tool or portion thereof. The defined physical characteristics can be electronically (programmatically) accessible by the system or known a priori and electronically stored locally or remotely and used to automatically calculate certain information and/or to segment image data. That is, the tool data from the model can be used to segment image data and/or correlate a position and orientation of a tool and/or provide trajectory adjustment guidelines or error estimates, warnings of improper trajectories and the like. For example, a grid for marking a burr hole location and/or a trajectory guide that adjusts an intrabrain path for placing a diagnostic or therapy device and such can be input, transposed, and/or overlayed in a visualization of the tool and patient structure or otherwise used, such as, for example, to project the information onto a patient's anatomical structure or determine certain operational parameters including which image volume to obtain high resolution MRI image data that include select portions of the targeting canula. At least some of the resulting visualizations are not merely an MRI image of the patient during a procedure.

The visualizations are rendered visualizations that can combine multiple sources of data to provide visualizations of spatially encoded tool position and orientation with anatomical structure and can be used to provide position adjustment data output so that a clinician can move a controller a certain amount to obtain a desired trajectory path, thereby providing a smart-adjustment system without requiring undue "guess" work on what adjustments to make to obtain the desired trajectory.

The term "animation" refers to a sequence or series of images shown in succession, typically in relatively quick succession, such as in about 1-50 frames per second. The term "frame" refers to a single visualization or static image. The term "animation frame" refers to one image frame of the different images in the sequence of images. The term "ACPC coordinate space" refers to a right-handed coordinate system defined by anterior and posterior commissures (AC, PC) and Mid-Sagittal plane points, with positive directions corresponding to a patient's anatomical Right, Anterior and Head directions with origin at the mid-comissure point.

The term "grid" refers to a pattern of crossed lines or shapes used as a reference for locating points or small spaces, e.g., a series of rows and intersecting columns, such as horizontal rows and vertical columns (but orientations other than vertical and horizontal can also be used). The grid can include associated visual indicia such as alphabetical markings (e.g., A-Z and the like) for rows and numbers for columns (e.g., 1-10) or the reverse. Other marking indicia may also be used. The grid can be provided as a flexible patch that can be releasably attached to the skull of a patient.

For additional description of suitable grid devices, see co-pending, co-assigned U.S. patent application Ser. No. 12/236,621.

The term "fiducial marker" refers to a marker that can be electronically identified using image recognition and/or electronic interrogation of MRI image data. The fiducial marker can be provided in any suitable manner, such as, but not limited to, a geometric shape of a portion of the tool, a component on or in the tool, a coating or fluid-filled component or feature (or combinations of different types of fiducial markers) that makes the fiducial marker(s) MRI-visible with sufficient signal intensity (brightness) for identifying location and/or orientation information for the tool and/or components thereof in space.

The term "RF safe" means that the lead or probe is configured to safely operate when exposed to RF signals, particularly RF signals associated with MRI systems, without inducing unplanned current that inadvertently unduly heats local tissue or interferes with the planned therapy. The term "MRI visible" means that the device is visible, directly or indirectly, in an MRI image. The visibility may be indicated by the increased SNR of the MRI signal proximate the device.

The system can include an intrabody MRI receive imaging probe antenna to collect signal from local tissue. The term "MRI compatible" means that the so-called component(s) is safe for use in an MRI environment and as such is typically made of a non-ferromagnetic MRI compatible material(s) suitable to reside and/or operate in a high magnetic field environment. The term "high-magnetic field" refers to field strengths above about 0.5 T, typically above 1.0 T, and more typically between about 1.5 T and 10 T. MRI Scanners are well known and include high-field closed bore and open bore systems.

Embodiments of the present invention can be configured to carry out diagnostic and interventional procedures such as to guide and/or place interventional devices to any desired internal region of the body or object, but may be particularly suitable for neurosurgeries. The object can be any object, and may be particularly suitable for animal and/or human subjects. Although primarily described with respect to placement of stimulation leads in the brain, the invention is not limited thereto. For example, the system can be used for gene and/or stem-cell based therapy delivery or other neural therapy delivery and allow user-defined custom targets in the brain or to other locations. In addition, embodiments of the systems can be used to ablate tissue in the brain or other locations. In some embodiments, it is contemplated that the systems can be configured to treat AFIB in cardiac tissue, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

Examples of known treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Embodiments of the present invention may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Generally stated, embodiments of the systems are configured to provide a substantially automated or semi-automated and relatively easy-to-use MRI-guided systems with defined workflow steps and interactive visualizations. In particular embodiments, the systems define and present workflow with discrete steps for finding target and entry point(s), localizing the entry point(s) to a physical identified grid position, guiding the alignment of the targeting canula to a planned trajectory, monitoring the insertion of the probe, and adjusting the X-Y position in cases where the placement needs to be corrected. During steps where specific MR scans are used, the circuit or computer module can display data for scan plane center and angulation to be entered at the console. The workstation/circuit can passively or actively communicate with the MR scanner. The system can also be configured to use functional patient data (e.g., fiber tracks, fMRI and the like) to help plan or refine a target surgical site.

Embodiments of the present invention will now be described in further detail below with reference to the figures. FIG. 1 illustrates an MRI guided interventional system 10 with an MRI scanner 20, a clinician workstation 30 with at least one circuit 30c, at least one display 32 and at least one MRI compatible interventional and/or surgical tool 50. An MRI scanner interface 40 may be used to allow communication between the workstation 30 and the scanner 20. The interface 40 and/or circuit 30c may be hardware, software or a combination of same. The interface 40 and/or circuit 30c may reside partially or totally in the scanner 20, partially or totally in the workstation 30, or partially or totally in a discrete device therebetween. The system 10 can be configured to render or generate real time visualizations of the target anatomical space using MRI image data and predefined data of at least one surgical tool to segment the image data and place the tool 50 in the rendered visualization in the correct orientation and position in 3D space, anatomically registered to a patient. The tool 50 can include or cooperate with tracking, monitoring and/or interventional components. The system 10 can optionally include a reader 30r that can electronically read (e.g., optically such as via a bar code or otherwise electronically read such a via an RFID tag) a label or tag or other indicia to confirm that the hardware is authentic or compatible to inhibit counterfeit hardware and potential misuse of the system as the system is configured so that certain hardware define a point of interface with the software or circuit 30c. Alternatively, or additionally, the system 10 can allow a user to manually input the tool/hardware indicia. Proper operation of the system requires that the proper hardware having the specific predefined characteristics used by the system is used for the surgical procedure.

Figure 2:
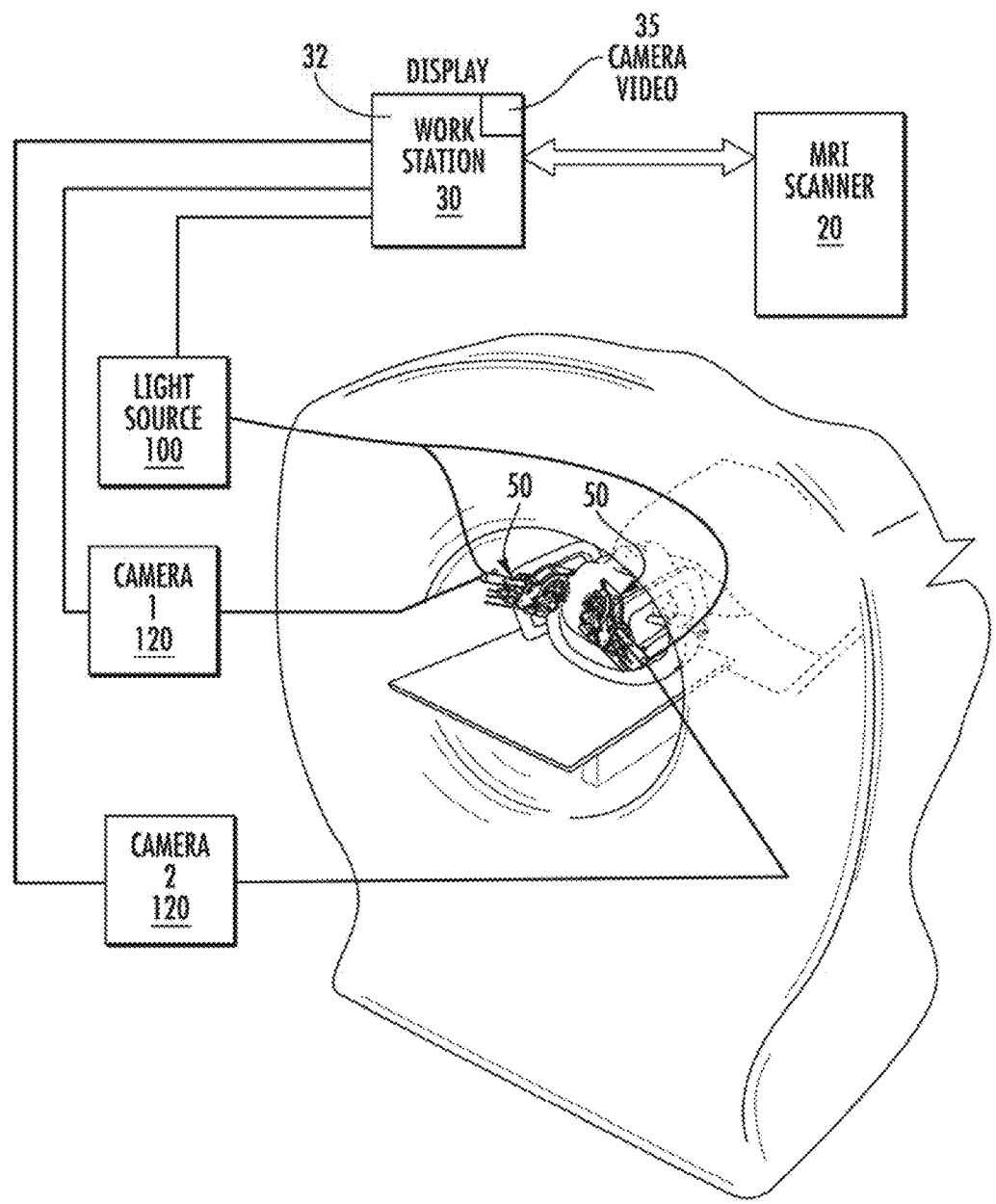
FIG. 2 is a schematic illustration of an MRI-guided surgical system with MRI compatible cameras according to embodiments of the present invention.
Figure 3:
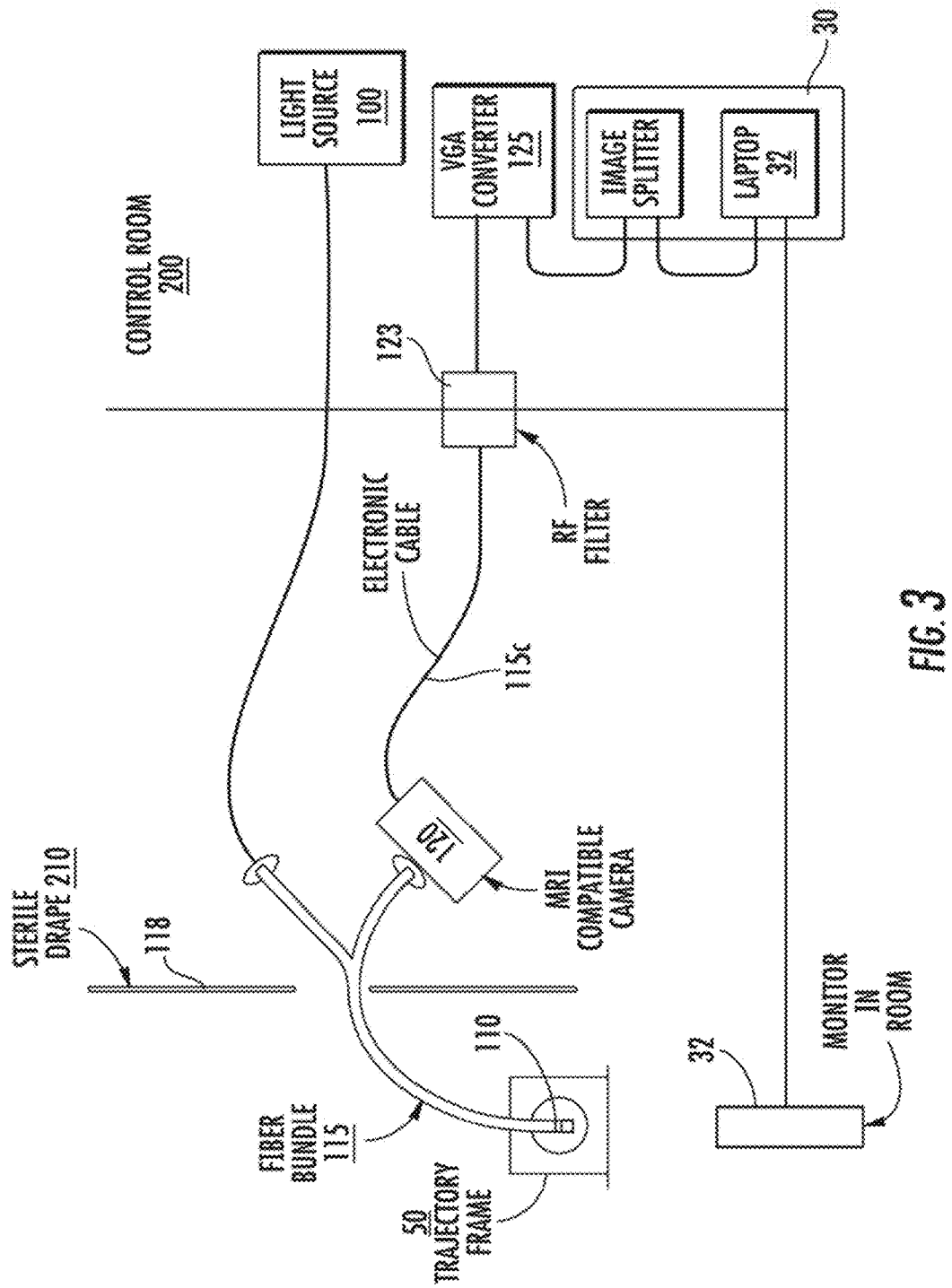
FIG. 3 is a schematic illustration of an MRI-guided surgical system according to some embodiments of the present invention.

FIGS. 2 and 3 are schematics of embodiments of the system 10 which illustrate that the system 10 can include a light source 100 in communication with a camera device 110 via a fiber optic fiber bundle cable 115. FIG. 2 illustrates that the system 10 can be used for bilateral procedures. The camera device (fiberscope) 110 can have a distal lens and can be configured with a relatively small local field of view (residing proximate the burr hole or surgical entry location) to allow a clinician to monitor the surgical entry point. The fiber-optic camera device 110 can be mounted to the trajectory guide 50. The return signal is fed to an MRI compatible video camera 120 and the signal is transmitted as a video of the patient and can be shown in a display or split screen 32 at the workstation 30. The workstation 30 can be in a control room 200 and the feed from the fiber optic cable from the camera 115c can be via an RF filter 123 to inhibit signal distortion to the video stream shown on the display 32. A separate display or monitor can also reside in the surgical room 210. A sterile surgical drape 118 can be used to maintain a sterile side inside the surgical room 210 on the bore end of the magnet facing the camera 120. On example of a suitable MR compatible video camera is available from MRC Systems GmbH, Heidelberg, Germany.

Figure 4:
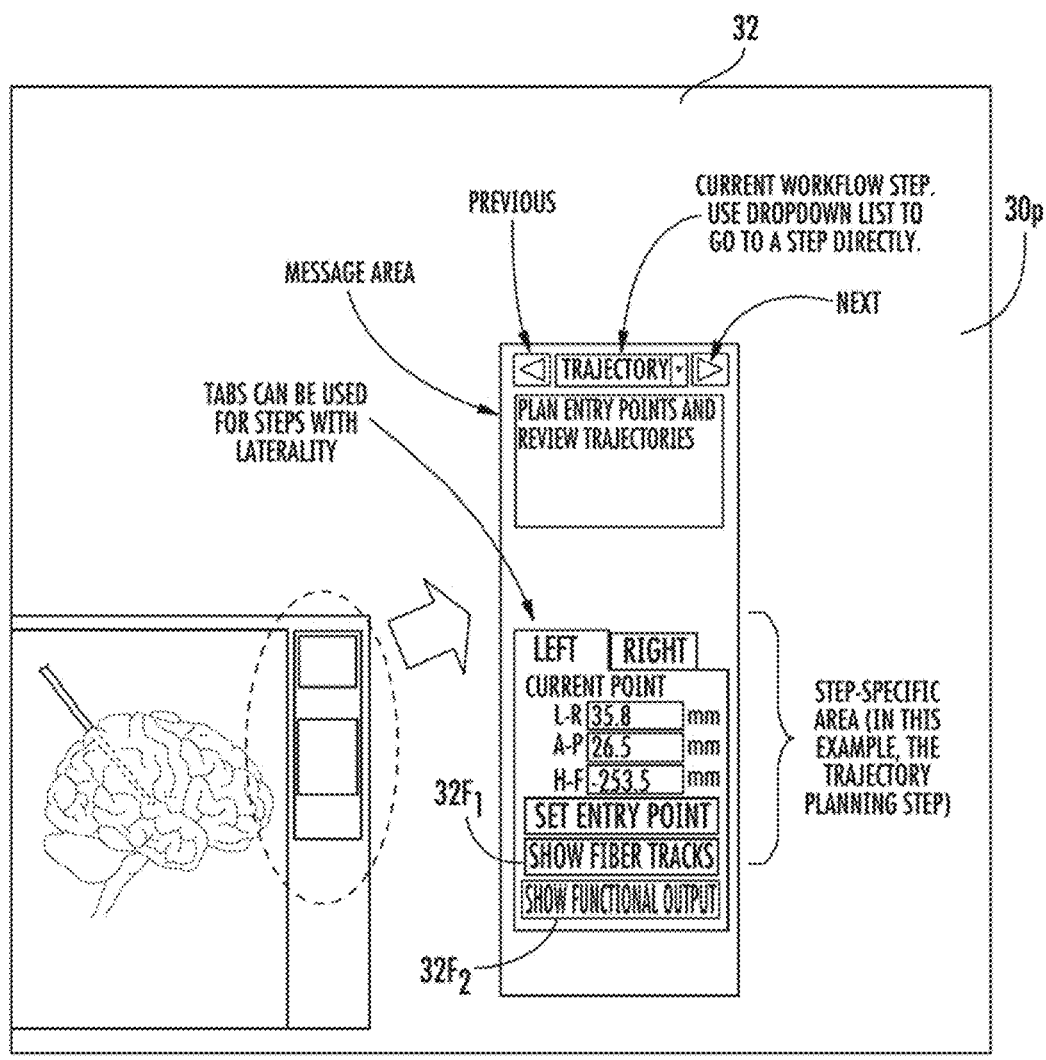
FIG. 4 is a schematic illustration of an exemplary screen shot of a user interface according to some embodiments of the present invention.

The system 10 can be configured to provide workflow for a unilateral or bilateral (or even trilateral or more) procedure. Selection of the procedure type can initiate the associated work flow presented. FIG. 4 illustrates an example of a workstation control panel 30p on display screen 32. The panel 30p can illustrate a current workflow step and allow a user to go to a step directly (such as via a drop down list or selection of a workflow step in a toolbar or the like) and can be presented adjacent different views of the intrabody trajectory and patient anatomy. Tabs or other user-selectable features with visual feedback on status of a step for each side can be used for steps with laterality (e.g., left or right for bilateral procedures) to allow a user to control selection of laterality, such as left 30a and right 30b, to complete trajectory planning for each side independently (or to allow a user to toggle back and forth while maintaining control over each side). The display 32 can include viewer tools such as zoom, pan, width/level, magnifier, etc.

The MRI scanner 20 can include a console that has a "launch" application or portal for allowing communication to the circuit 30c of the workstation 30. The scanner console can acquire volumetric T1-weighted (post-contrast scan) data or other image data (e.g., high resolution image data for a specific volume) of a patient's head or other anatomy. In some embodiments, the console can push DICOM images or other suitable image data to the workstation 30 and/or circuit 30c. The workstation 30 and/or circuit 30c can be configured to passively wait for data to be sent from the MR scanner 20 and the circuit 30c/workstation 30 does not query the Scanner or initiate a communication to the Scanner. In other embodiments, a dynamic or active communication protocol between the circuit 30c/workstation 30 and the Scanner 20 may be used to acquire image data and initiate or request particular scans and/or scan volumes. Also, in some embodiments, pre-DICOM, but reconstructed image data, can be sent to the circuit 30c/workstation 30 for processing or display. In other embodiments, pre-reconstruction image data (e.g., substantially "raw" image data) can be sent to the circuit 30c/workstation 30 for Fourier Transform and reconstruction.

Generally described, for some unilateral scenarios, the user will proceed through a set of discrete workflow steps to load MR image data, identify a target point, identify an entry point, verify the planned trajectory, and align the targeting canula. A target point or region can also be planned or refined based on real-time functional image data of a patient. The functional image data can include, but is not limited to, images of fiber tracks, images of activity in brain regions during vocalization (e.g., reading, singing, talking), or based on physical or olefactory or sense-based stimulation, such as exposure to electrical (discomfort/shock input), heat and/or cold, light or dark, visual images, pictures or movies, chemicals, scents, taste, and sounds or the like) and/or using fMRI or other imaging techniques. The enhanced visualization gives neurosurgeons a much clearer picture of the spatial relationship of a patient's brain structures. The visualizations can serve as a trajectory guide for surgical procedures, such as brain-tumor removal and epilepsy surgery.

In some embodiments, the visualizations can be generated using data collated from different types of brain-imaging methods, including conventional magnetic resonance imaging (MRI), functional MRI (fMRI), diffusion-tensor imaging (DTI) and even hyperpolarized noble gas MRI imaging. The MRI gives details on the anatomy, fMRI or other active stimulation-based imaging protocol can provide information on the activated areas of the brain, and DTI provides images of the network of nerve fibers connecting different brain areas. The fusion of one or all of these different images and the tool information can be used to produce a 3-D display with trajectory information that surgeons can manipulate.

Thus, a target location and trajectory can be planned, confirmed or refined based in-part on functional information of the patient. This functional information can be provided in real-time visualizations of the patient with the trajectory guide tools for trajectory path and target planning, e.g., visualize a patient's fiber track structures and/or functional information of a patient's brain for a surgeon's ease of reference. This information can also be selected or suppressed from views via a UI selection, such as "Show Fiber Tracks" $32F_1$ and/or "Show Functional Output" $32F_2$ (e.g., toolbar option) as shown in FIG. 4. It is noted that the patient functional information can be shown automatically without requiring a user selection or in response to a stage of a procedure or when selecting certain steps. In addition, such information may be shown or selected in any appropriate display or step described herein although not specifically described with respect to that particular step or screen display. Knowing where susceptible or sensitive brain regions are or where critical fiber tracks are in the patient's brain, can allow a surgeon to plan a better, less-risky or less-intrusive trajectory and/or allow a surgeon to more precisely reach a desired target site and/or more precisely place a device and/or deliver a planned therapy, e.g., implant a stimulation lead, ablate tissue and/or treat a tumor site and/or excise a tumor, deliver a gene and/or stem cell therapy and the like.

To align the targeting canula, scan volumes can be defined by the system based on known dimensions of the canula, such as a canula length a position of a proximal or distal marker on the canula, and angulation and lateral (X-Y) pivot limit. In particular embodiments, the user can then gradually advance a probe and a peel away sheath (that is configured to guide an interventional device to a desired location along the defined trajectory) and acquire images to check for hemorrhage and to verify the trajectory and/or avoid functionally sensitive structure. When the probe has been advanced to the target point, high-resolution confirmation images can be obtained to verify the tip location relative to the planned location. If actual placement is unacceptable, the probe can be withdrawn. At that point, either the X-Y placement can be adjusted appropriately (e.g., by moving a platform or stage an amount to cause the desired adjustment) or a trajectory angulation can be re-planned and a second attempt can be made.

For some bilateral scenarios, the above steps can be repeated for both left and right sides, with the additional goal that the patient should not be moved into or out of the scanner. To satisfy that goal, trajectory planning should be completed for both sides prior to removing the patient from the scanner. Also, burring and frame attachment (the member that holds the trajectory guide to the patient's head) should be completed for both sides prior to moving the patient back into the scanner to promote speed of the procedure.

The system 10 can be configured with a hardware interface that provides a network connection, e.g., a standard TCP/IP over Ethernet network connection, to provide access to MR scanner 20, such as the DICOM server. The workstation 30 can provide a DICOM C-STORE storage class provider. The scanner console can be configured to be able to push images to the workstation 30 and the workstation 30 can be configured to directly or indirectly receive DICOM MR image data pushed from an MR Scanner console. Alternatively, as noted above, the system can be configured with an interface that allows for a dynamic and interactive communication with the Scanner 20 and can obtain image data in other formats and stages (e.g., pre-DICOM reconstructed or raw image data).

As noted above, the systems 10 are configured so that hardware, e.g., one or more specific surgical tools, constitute a point of interface with the system (software or computer programs) because the circuit 30c is configured with predefined tool data that recognizes physical characteristics of specific tool hardware.

Figure 5:
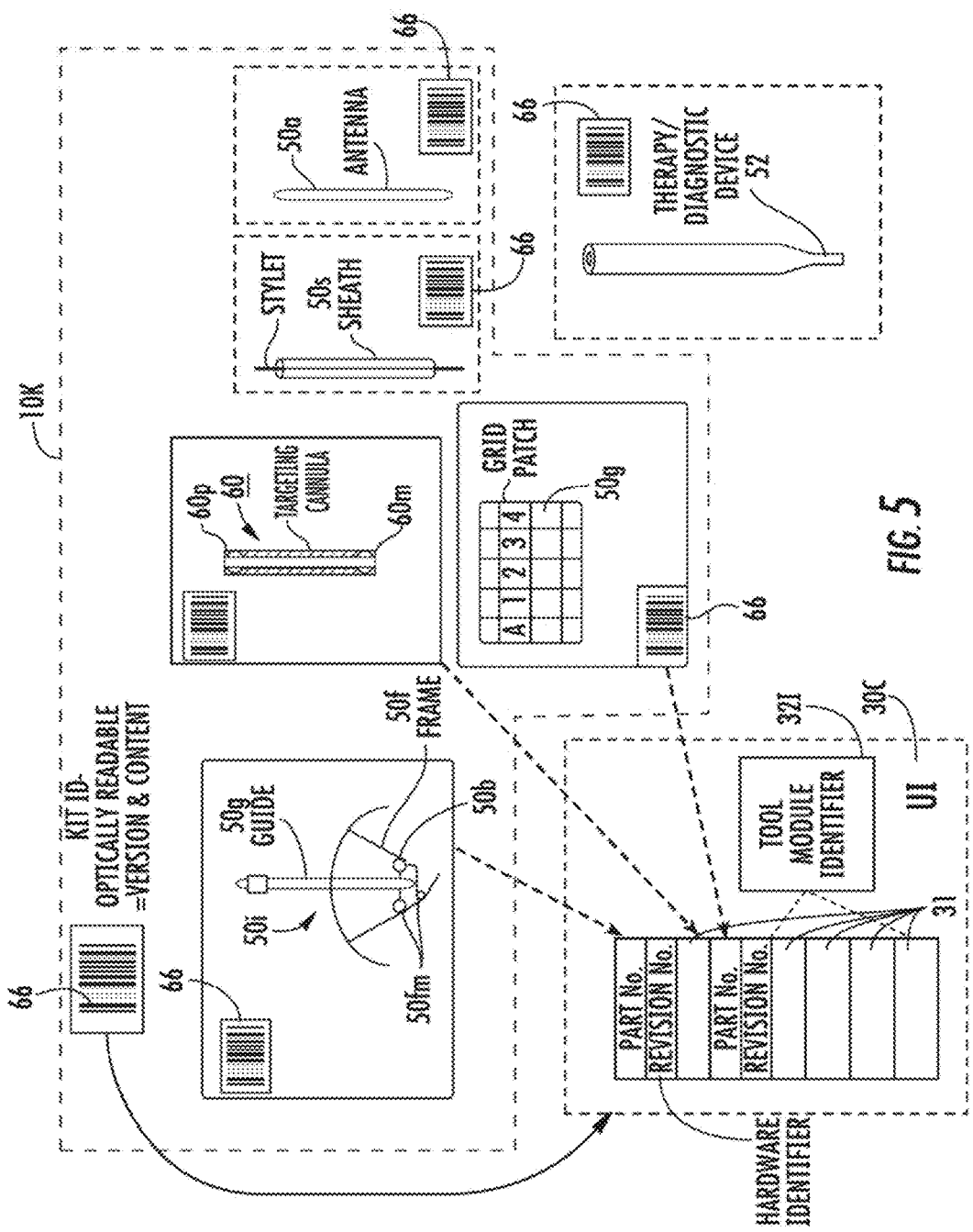
FIG. 5 is a schematic of exemplary disposable hardware that can be used to carryout embodiments of the present invention.

As shown in FIG. 5, to assure proper operation, the system 10 can be configured to require entry of a valid identifier and/or revision controlled/based part number to validate that the hardware planned for use is appropriate for use in the system 10 (or at least that version of the system). Thus, a reader 30r associated with the workstation 30 can be configured to read a single "group" identifier 66 that can be placed on the kit package or provided with the kit 10k and/or the reader can be configured to read each tool that has predefined characteristics to confirm the appropriate part and version is in the kit. Alternatively, or additionally, the system 10 can allow a user to manually input the tool/hardware identifier data (e.g., hardware version and/or part number) into a UI associated with the circuit 30c. The workstation 30 can include a look-up chart of a correlation table 31 that confirms the correct hardware is in the kit 10k or otherwise provided for use. Thus, the workstation 30 can be configured with a user interface 32I (shown as a Tool Version Identifier Panel) that requires a user to electronically or manually enter the identifier 66 and/or to acknowledge compliance with the tool-specific operation of the system 10. It is envisioned that the circuit 30c can be configured with updates and backward compatibility for future controlled changes to the specific tools and/or with the ability to use different module versions of the system according to the version of the tool or tools then in use at the surgical site.

To inhibit the use of counterfeit hardware with the system 10, the identifier may include indicia that can be keyed to a particular authorized use site and/or authorized user. The system may be configured to require a user to certify that the hardware is OEM hardware or authorized hardware to be able to receive an electronic key to be able to activate the system. A user may be required to contact the OEM or other authorized party to obtain an electronic key or identifier to allow use of the hardware with the system 10.

Figure 8:
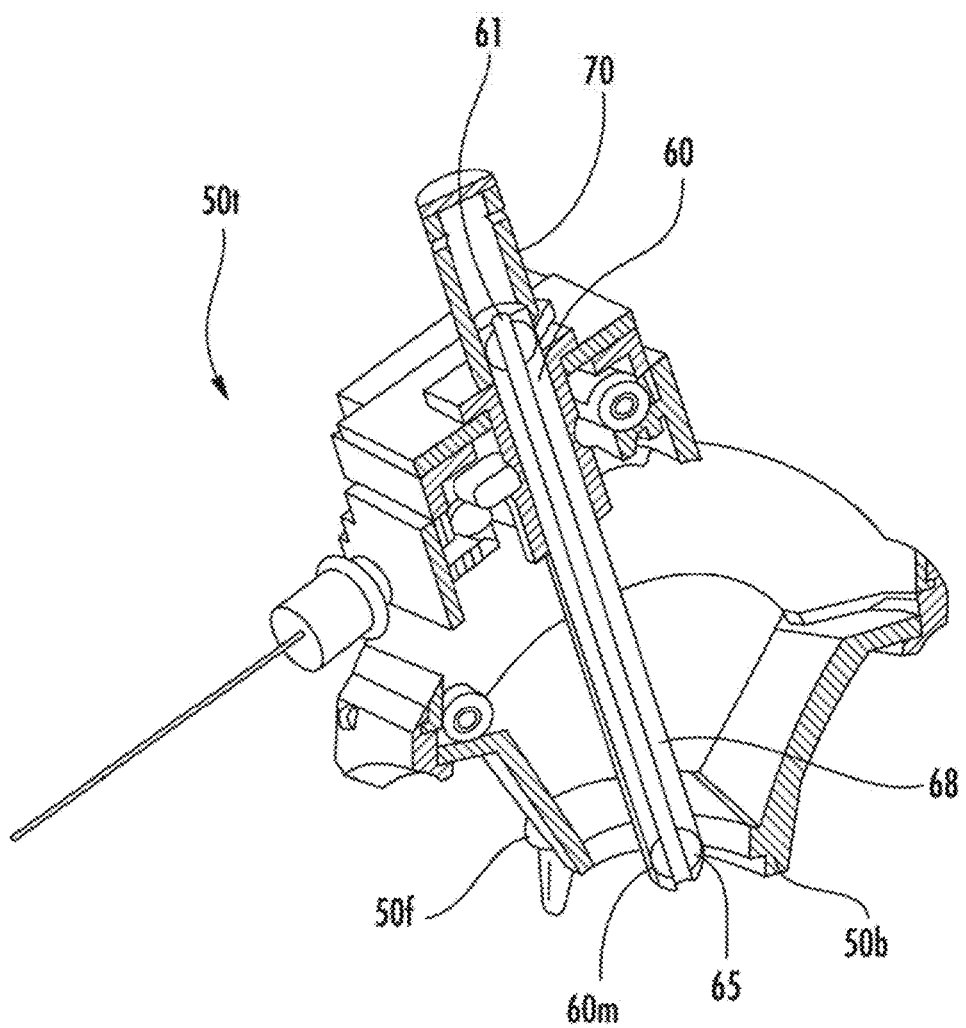
FIG. 8 is a sectional view of the trajectory guide with a targeting canula according to some embodiments of the present invention.

As shown in FIG. 5, in some embodiments, the system is programmatically configured to recognize defined physical characteristics of different tools. Those tools that can be provided as a kit 10k (typically a single-use disposable hardware) or in other groups or sub-groups or even individually, typically provided in suitable sterile packaging. The tools can include at least one marking grid 50g (also referred to as a grid patch), a targeting canula 60 with a distal marker 60m and an opposing proximal portion of the canula 60p. The targeting canula 60 can include an open center lumen or passage 61 (FIG. 8). The distal maker 60m typically includes a substantially spherical fluid filled component 65 (FIG. 8). The proximal portion of the canula 60p can include a marker, but is typically identified in the image data based, at least in-part) on the distal maker 60m and its known distance and orientation with respect thereto based on the physical characteristics of the targeting canula 60. Still referring to FIG. 5, the system 10 can also include a trajectory guide 50t with a plurality of MRI visible frame fiducial markers 50fm around a base 50b thereof. The system 10 may also include a stylet that can communicate with a peel-away sheath 50s and an imaging probe 50a (that provides an intrabody receive antenna that can be slidably introduced via the passage of the targeting canula 60). Certain components of the kit may be replaced or omitted depending on the desired procedure. Certain components can be provided in duplicate for bilateral procedures. As shown in FIG. 5, a therapy delivery device 52 may optionally be provided, also with an identifier such as a label or tag 66. The device 52 can be configured to flowably introduce and/or inject a desired therapy (e.g., gene therapy or stem-cell or other therapy type) or obtain a biopsy and the like.

Figure 6A:
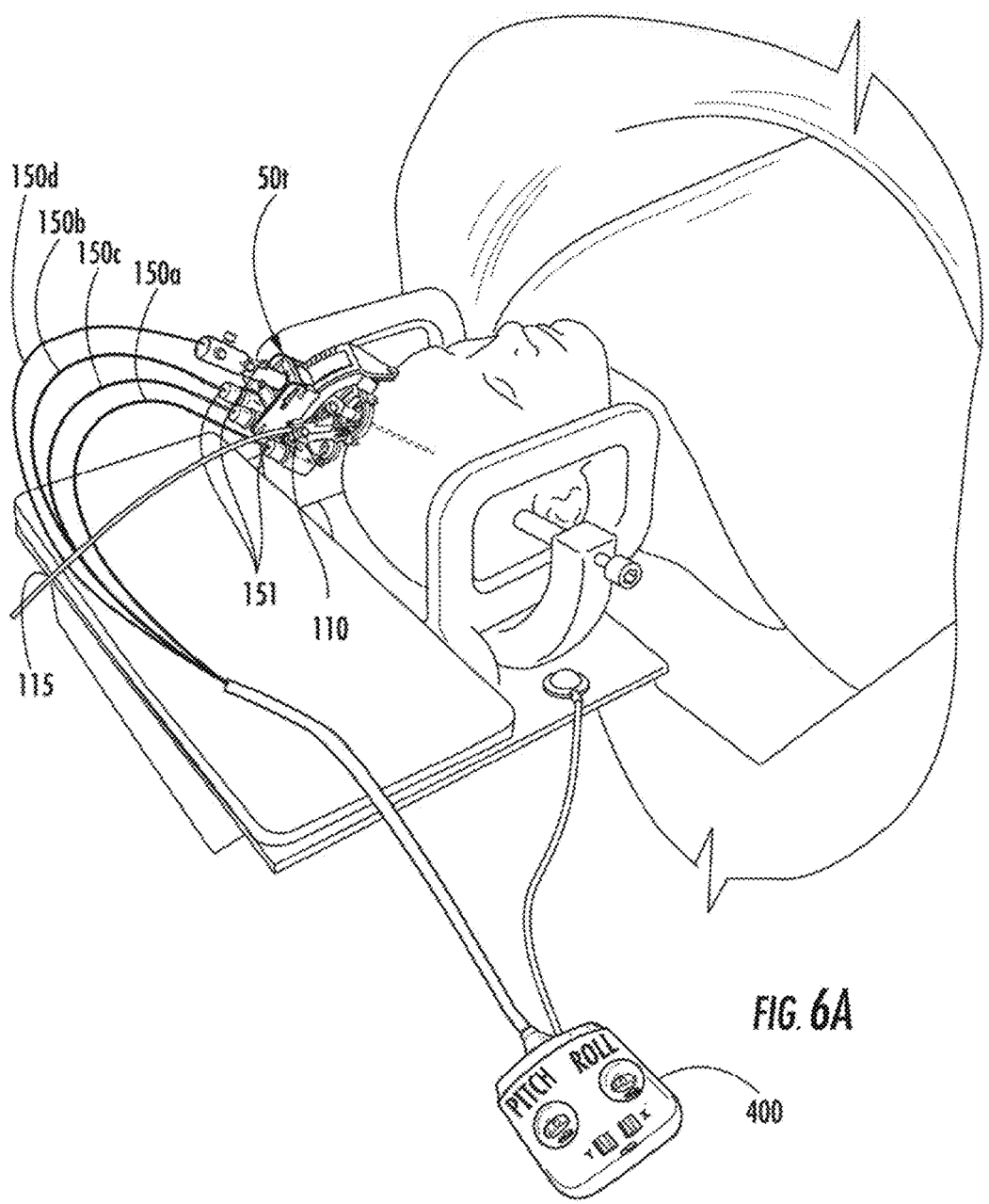
FIG. 6A is a schematic of an exemplary trajectory guide in position on a patient according to some embodiments of the present invention.

FIGS. 6A-6C, and 7-10 illustrate the trajectory guide 50t with the targeting canula 60 and various features described above. FIG. 6A illustrates a trajectory guide 50t and targeting canula 60 in position on a patient with trajectory guide actuators 151 and respective actuator cables 150a-150d (providing X-Y adjustment and pitch and roll adjustment) in communication with a trajectory adjustment controller 400. The frame 150f can include control arcs 152 (FIGS. 7, 10) that cooperate with a platform 153 (FIG. 7) to provide pitch and roll adjustments. The platform 153 can allow for X-Y adjustments of the trajectory. For additional discussion of suitable trajectory guides, see, U.S. application Ser. No. 12/134,412, and co-pending, co-assigned U.S. patent application Ser. No. 12/236,950, the contents of which are hereby incorporated by reference as if recited in full herein.

Figure 6B:
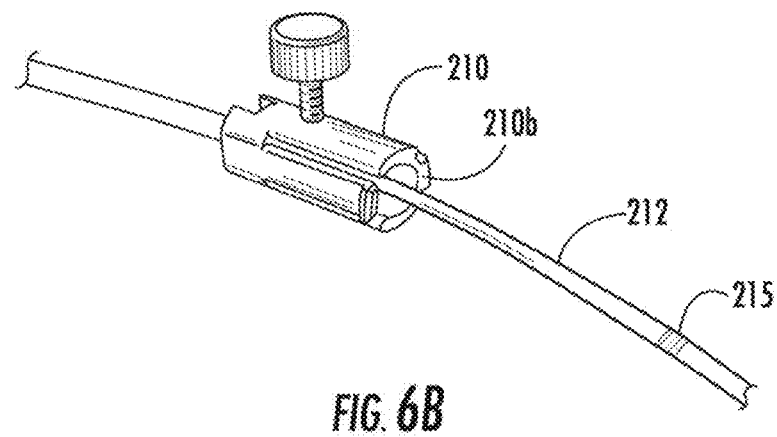
FIG. 6B is a side view of a depth stop with a cooperating elongate member according to some embodiments of the present invention.
Figure 6C:
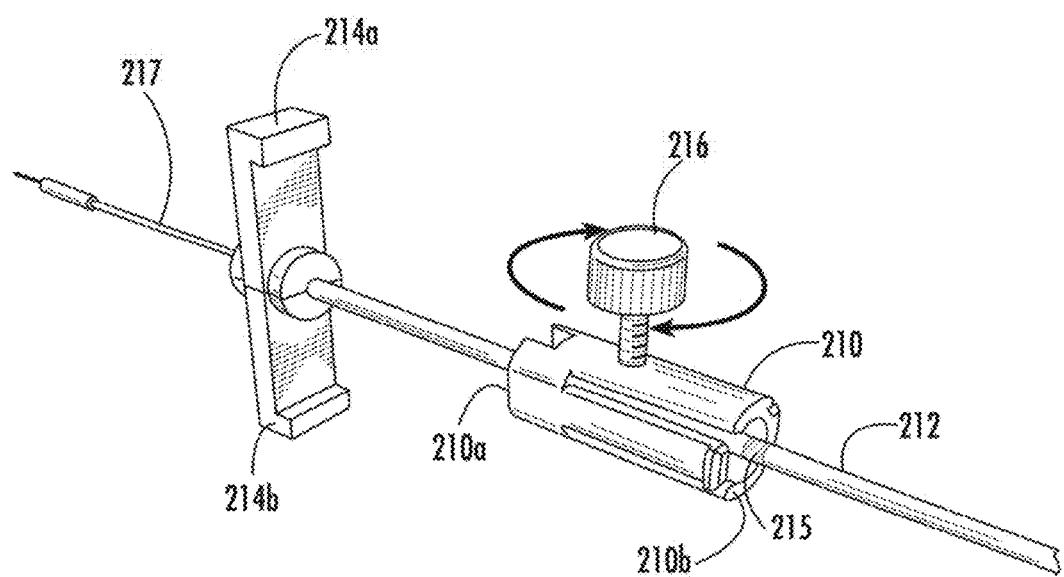
FIG. 6C is a side view of a depth stop cooperating with an elongate member and peel-away sheath according to some embodiments of the present invention.

FIGS. 6B and 6C illustrate examples of a depth stop 210 cooperating with an elongate member 212 such as, for example, a stimulation or ablation lead, a diagnostic and/or imaging probe, a removable sheath and/or other therapy or diagnostic device inserted and secured therein as illustrated. The illustrated depth stop 210 has a generally cylindrical configuration with opposite proximal and distal ends 210a, 210b and is adapted to be removably secured within the proximal end of the tubular trajectory guide member 50t (FIG. 6A). The depth stop 210 is configured to limit a distance that the member 212 extends into the body of a patient when the depth stop is inserted within the tubular member 50t or 60. The member 212 can include visual indicia of insertion depth 215 to allow a user to visually attach the stop 210 at the appropriate location that provides the desired insertion depth.

Figure 6D:
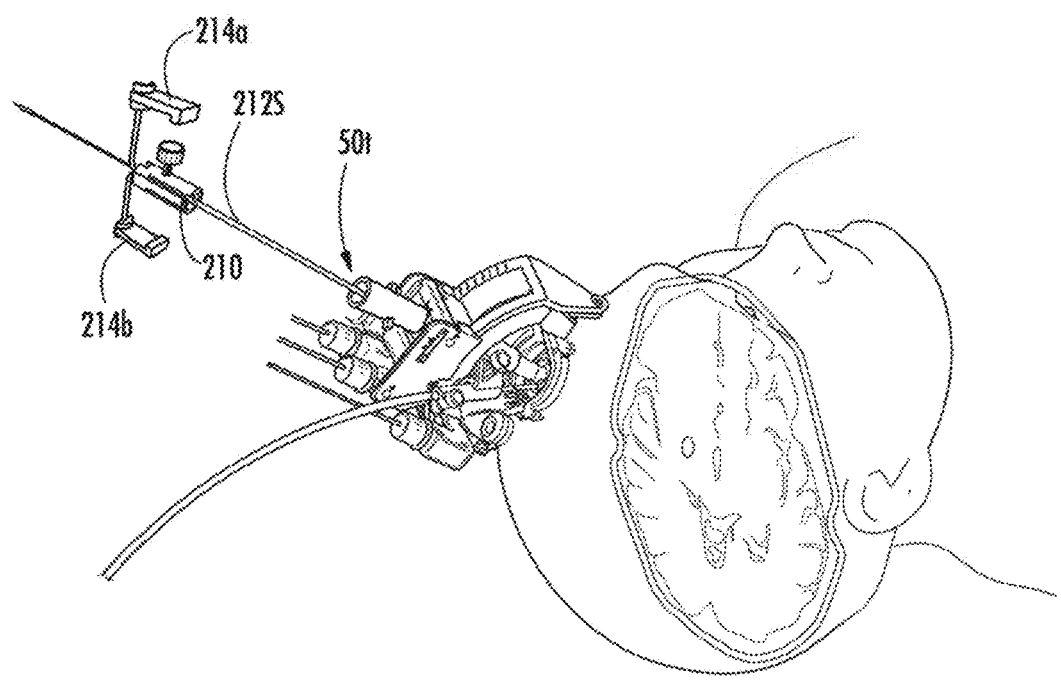
FIG. 6D is a side perspective view of the depth stop and sheath cooperating with the trajectory guide according to some embodiments of the present invention.

As shown in FIGS. 6C and 6D, in some embodiments, the depth stop 210 is attached to a peel-away sheath 212s (see also probe 50s, FIG. 5) and can be configured to receive and guide an elongated interventional device, such as a stylet or imaging probe, therethrough. As shown in FIGS. 6C and 6D, the sheath 212s can include opposing tabs that, when pulled apart, cause the sheath to peel away for removal from the targeting canula 60. In other embodiments, the depth stop 210 can be attached to a stimulation lead to allow for a defined insertion depth (see, e.g., FIG. 38 below) or other device where insertion depth control is desired.

Figure 7:
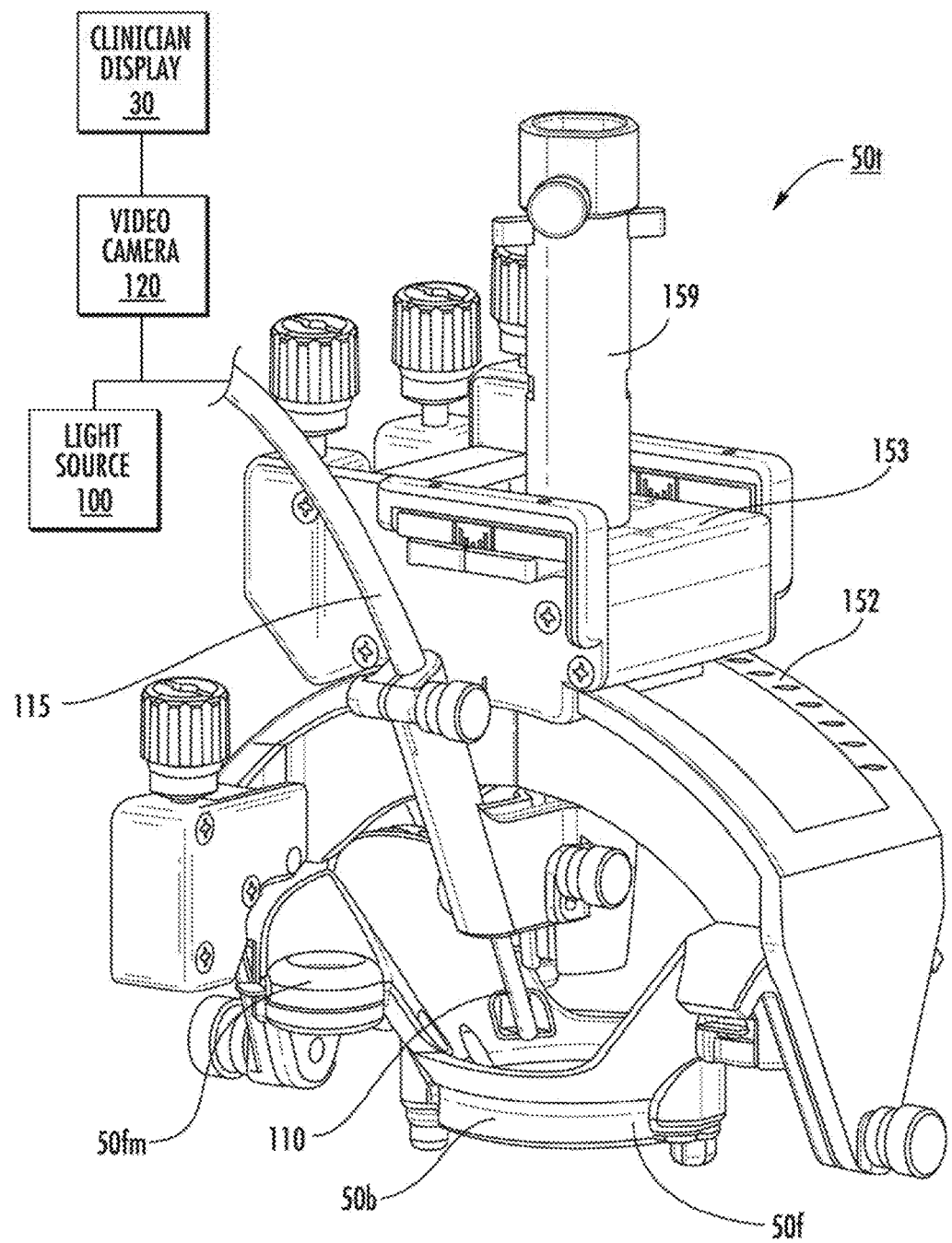
FIG. 7 is a side perspective view of a trajectory guide and optional camera device according to some embodiments of the present invention.

As shown in FIG. 7, the targeting canula 60 can be attached to the trajectory guide 50t. The targeting canula 60 can include a through passage 61. The distal end of the targeting canula 60 has a fiducial marker 60m, shown as a substantially spherical or round (cross-section) marker shape. The proximal end 60p can be configured with a fluid filled channel 68 concentric with the passage 61 that can define a cylindrical fiducial marker. Along the axis of the canula 60, there is the lumen or passage 61 through which another device can be slidably introduced and/or withdrawn, e.g., a stylet 50s, imaging probe 50a, therapy delivery or diagnostic device 52 (FIG. 5) and DBS stimulation leads for implantation, can be advanced into the brain.

FIG. 11A illustrates an example of a grid patch 50g with physical characteristics that are predefined and available to or in the circuit 30c (e.g., software application). FIG. 11B illustrates that the grid can allow for precise correlation of logical points in an MR volume with the physical patient. The system 10 can be configured to generate a 3-D volumetric view on the display 32 with overlays to show the grid 50g and an entry point and grid coordinates (and optionally grid edges) allowing a burr hole mark to be made on a skull at the desired planned entry point.

Figure 12A:
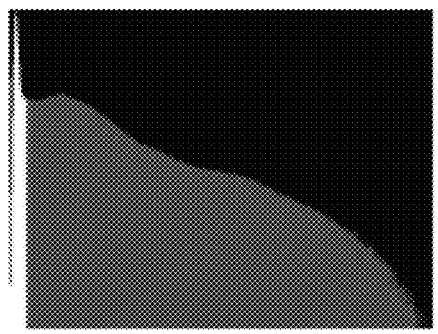
FIGS. 12A-12E are schematic illustrations of grid segmentation and grid deformation that can be used to define an entry site location according to embodiments of the present invention.
Figure 12B:
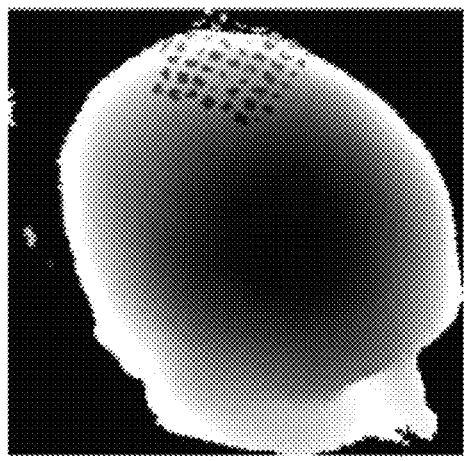
Figure 12C:
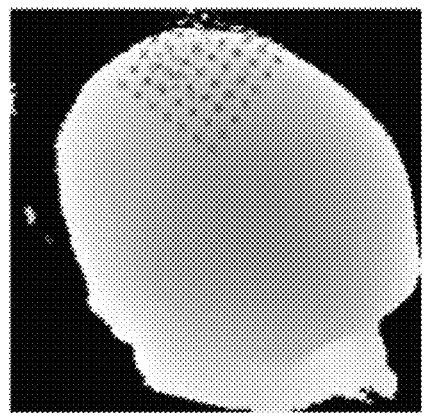
Figure 12D:
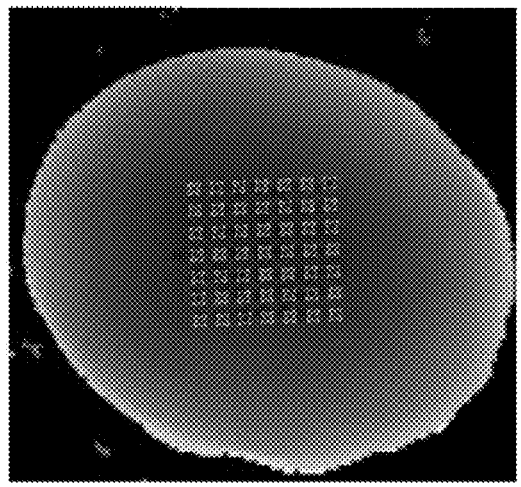
Figure 12E:
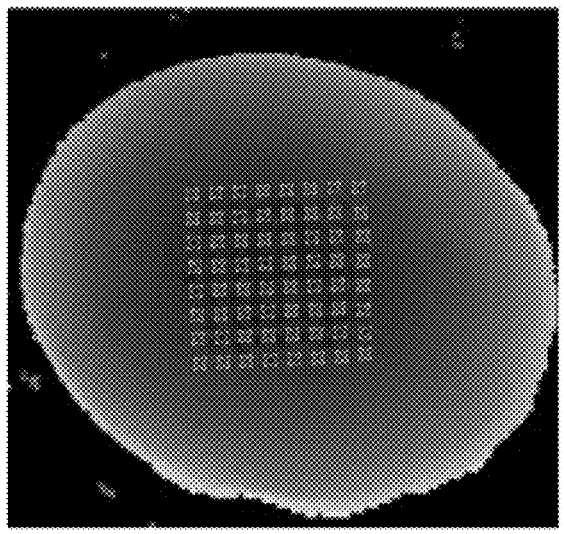

FIGS. 12A-12E illustrate a series of operations that can be carried out for the grid 50g segmentation. Some or all of these operations may be carried out behind the scene (e.g., not actually displayed). FIG. 12A illustrates an example of a histogram. FIG. 12B is an example of an initial distance image. FIG. 12C is an image of a result of searching for the grid in the initial distance image. FIG. 12D illustrates the result of searching for the grid in the optimal distance image, with small step sizes. FIG. 12E illustrates the result of spatially deforming the grid to fit the head surface and interpolating the grid cells to find the vertices.

With reference to FIG. 12A, the amplitude of the background noise in the input image stack can be estimated. To do so, a histogram of the stack can be constructed. The first negative maximum of the slope of the histogram can be located. The first peak to the left of this maximum can be located (this can be termed the "noise peak"). The difference between the noise peak and the first negative maximum of the slope can approximate the standard deviation of the noise. The noise threshold can be obtained using the following Equation (1).

(noise threshold)=(noise peak)+4*(noise standard deviation)  EQUATION (1)

The above can be considered as a first step in the grid segmentation of the image data. Steps 2-5 can be carried out as described below to place the grid in position and deform to curvature of the skull for the grid segmentation.

2. Estimate the "optimal view direction" for the grid. This is defined as the vector from the grid center to the midpoint of the AC-PC line:
   a. Construct an initial distance image as shown in FIG. 12B starting from a rough estimate of the optimal view direction:
      i. Create an image plane that is perpendicular to the estimated view direction, and outside of the head volume.
      ii. For each pixel in the image plane, record its distance to the first voxel in the image volume that is above the noise threshold.
   b. Find the grid cells in the distance image:
      i. The grid cells are "bumps" on the head surface, so they appear as local minima in the distance image. This characteristic is enhanced by applying a Laplacian-of-Gaussian operator to the distance image.
      ii. For each location in the image, place a virtual grid (whose dimensions match those of the physical grid), at several orientations. Compute a score by tallying 1 point for each virtual grid cell that lands on one of the image minima. The highest score corresponds to the location and orientation of the grid in the distance image.

c. The center of the grid so obtained gives a new estimate of the optimal view direction. This estimate is used as a starting point of a new iteration of steps 2a, and 2b, in order to refine the estimate.

3. Find the grid using the optimal view direction:
a. Construct a distance-image as described in step 2a, but using the optimal view direction obtained in step 2.
b. Find the grid in the new distance image, as described in 2b.
c. Refine the grid position and orientation by repeating the search procedure of 2b, but search only in a small region around the known approximate location, with very fine step-sizes (see, FIG. 12D).

4. Deform the grid to the shape of the head:
a. Up to this point, the grid has been taken to be planar.
b. Fit the grid cell locations in the distance image to a cubic surface using a robust regression algorithm, and snap each grid cell from step 3 to this surface. (This is to avoid producing a very irregular grid surface due to noise and low resolution in the distance image.)

Note that, in general, it is not possible to maintain equal distances between the grid cells when they are snapped to an arbitrary curved surface. Therefore an algorithm which simulates the behavior of the physical grid patch is used to minimize the amount of stretching and bending during the deformation.

5. Interpolate between the grid cells to compute the grid vertices. FIG. 12E illustrates a deformation result.

Figure 9:
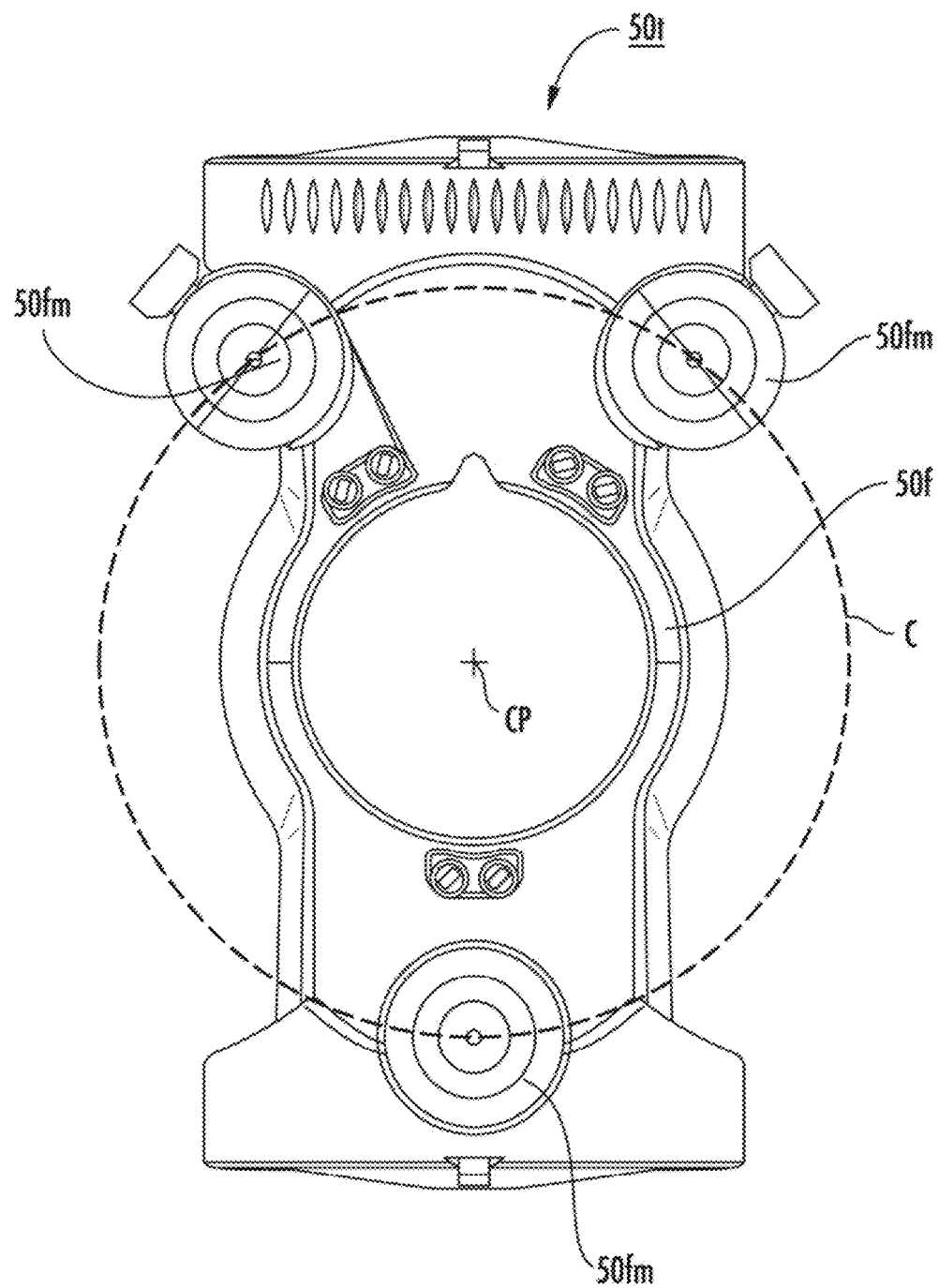
FIG. 9 is a top view of a base of a trajectory guide with fiducials according to some embodiments of the present invention.
Figure 10:
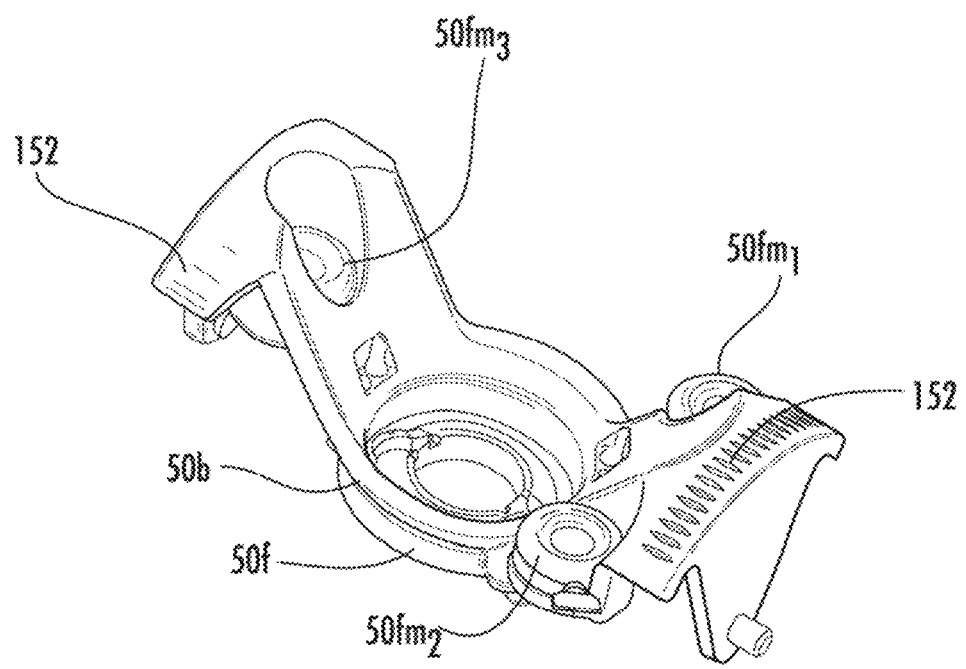
FIG. 10 is a side perspective view of the base shown in FIG. 9.
Figure 13A:
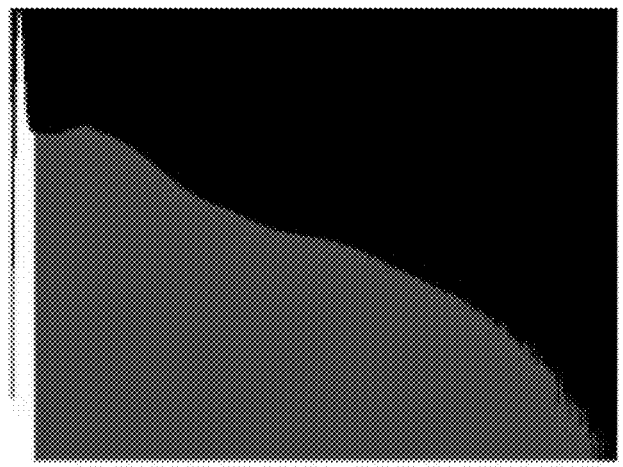
FIGS. 13A-13C are schematic illustrations of a base or frame marker segmentation that can be used to define position and orientation of a base or frame of a trajectory guide according to embodiments of the present invention.
Figure 13B:
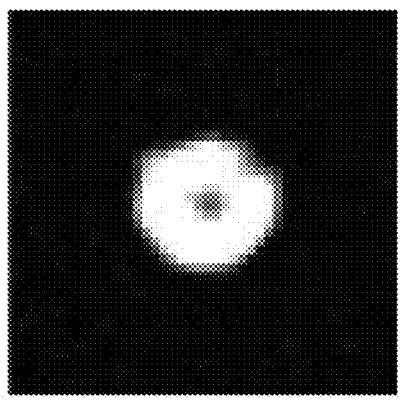
Figure 13C:
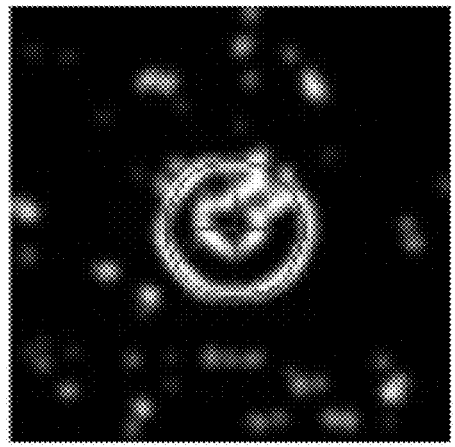

FIGS. 13A-13C illustrate images associated with a series of operations that can be carried out for frame marker segmentation. FIGS. 9 and 10 illustrate an example of a frame 50$f$ with fiducial markers 50$fm$ circumferentially spaced apart around a center "cp" and around a space for the burr hole with two of the markers 50$fm_1$, 50$fm_2$ closer together than a third 50$fm_3$ (FIG. 10). Different arrangements, configurations or numbers of fiducial makers as well as different locations on the frame 50$f$ and/or guide 50$t$ may be used and the frame segmentation can be altered accordingly.

Some or all of these operations illustrated in or described with respect to FIGS. 13A-C may be carried out behind the scene (e.g., not actually displayed). FIG. 13A illustrates an exemplary histogram with a noise region. FIG. 13B illustrates a cross-section of an imaged frame-marker. FIG. 13C illustrates a result of fitting a circle to the edge mask shown in FIG. 13B. The frame marker segmentation can define the orientation of the trajectory guide on the patient that can be correlated to mechanical output to cause the trajectory guide 50$t$ to translate to provide a desired trajectory, e.g., rotations and/or direction left, right, counterclockwise or clockwise or other translation for moving the actuators to change pitch and/or roll (or X-Y location).

With reference to FIG. 13A, the amplitude of the background noise in the input image stack can be estimated. To do so, a histogram of the stack can be constructed, the first negative maximum of the slope of the histogram can be located, the first peak to the left of this maximum can be located (this is the noise peak). The difference between the noise peak and the first negative maximum of the slope can approximate the standard deviation of the noise. The noise threshold can be obtained using the Equation (1) above. Again, this can be considered a first step in segmentation. Then, Steps 2-6 can be carried out with respect to the frame marker segmentation based on fit of an expected fiducial geometry to the observed fiducial positions because the fiducial markers are arranged with a fixed geometric relationship inside the volume.

2. Use a region-growing algorithm to find all "clumps" of pixels that are above the noise threshold.
3. Discard all clumps whose volumes are far from the known frame-marker volume.
4. Discard all clumps whose bounding-box dimension are far from the known bounding-box dimensions of the frame-markers.
5. Among the remaining clumps, look for triplets whose spatial arrangement matches the known spatial arrangement of the frame-markers of the trajectory base 50$b$ (i.e., the centroids of the clumps should form a triangle (e.g., an isosceles triangle) of known dimensions.)

At this point, if the number of clumps found for each frame (where bilateral procedures are used, there are two frames) is not exactly 3, then the segmentation is deemed to have failed.

6. For each triplet of markers, refine the marker locations:
a. Extract a 2D image of each marker by reformatting the stack onto the plane defined by the 3 marker centroids.
b. Compute the Canny edge mask of each 2D marker image.
c. Fit a circle to the Canny edge mask. The circle diameter is set equal to the diameter of the physical frame markers. The fit is performed by moving the circle until its overlap with the edge mask is maximized. The center of the fit circle is taken to be the location of the frame-marker's center.

In some embodiments, circuit 30$c$ can be configured so that the program application can have distinct ordered workflow steps that are organized into logical groups based on major divisions in the clinical workflow as shown in Table 1. A user may return to previous workflow steps if desired. Subsequent workflow steps may be non-interactive if requisite steps have not been completed. The major workflow groups and steps can include the following features or steps in the general workflow steps of "start", "plan entry", "plan target", "navigate", and "refine," ultimately leading to delivering the therapy (here placing the stimulation lead).

TABLE 1

EXEMPLARY CLINICAL WORKFLOW GROUPS/STEPS

| Group | Step | Description |
|---|---|---|
| Start | Start | Set overall procedure parameters (Optionally confirm hardware compatibility) |
| Plan Entry | ACPC | Acquire a volume and determine AC, PC, and MSP points |
| | Target | Define initial target point(s) for entry planning |
| | Trajectory | Explore potential trajectories to determine entry point(s) |
| | Grid | Locate physical entry point via fiducial grid. |
| Plan Target | ACPC | With hole burred and frame attached, acquire a volume and determine revised AC, PC, and MSP points. |
| | Target | Acquire high-resolution slabs (e.g., T2 slabs) to determine target positions in new volume. |
| | Trajectory | Review final planned trajectory prior to starting procedure. |
| Navigate | Initiate | Acquire slabs to locate initial position of canula. |
| | Alignment | Dynamically re-acquire scan showing position of top of canula. With each update show projected target position to determine when alignment is correct. |
| | Insertion | Acquire slabs as probe is inserted into brain. Verify that probe is following planned trajectory. |

TABLE 1-continued

EXEMPLARY CLINICAL WORKFLOW GROUPS/STEPS

| Group | Step | Description |
|---|---|---|
| Refine | Target | Acquire images with probes in place. Review position and redefine target if necessary. |
| | Adjust XY Offset | Dynamically re-acquire scan showing position of bottom of canula. With each update show projected target position to determine when offset is correct. |
| | Insertion | Acquire slabs as probe is inserted into brain. Verify that probe is following planned trajectory. |
| | Lead Placement | Once probe position is finalized, prompt user to place DBS leads or other device. |
| Admin | Admin | Reporting and Archive functionality. |

TABLES 2A-2P provide additional examples of some exemplary operations that may be associated with exemplary workflow steps according to some embodiments of the present invention.

TABLE 2A

Workflow Group Start Step Description

The start step can provide UI (User Interface) for selecting procedure laterally.
The start step can provide UI for selecting target: STN, Gpi, or Custom
The start step can provide UI for specifying the scanner bore diameter or scanner type that defines the size.
The start step can provide UI for entering hardware identifier data (e.g., version code) from the disposable hardware kit. If the version does not match the version supported by the software, an error can be shown, and the application can remain disabled.

TABLE 2B

Plan Entry - AC-PC Step Description

While data is being sent to the application, the UI can be disabled.
Given a 3D MR series of a whole human head, the application can automatically identify the AC, PC, and MSP points.
The application can display reformatted coronal, sagittal, and axial views aligned to the current AC, PC, and MSP points.
AC, PC, and MSP points can be editable in any MPR view in this step. On changing these points, the views can update to realign to the new ACPC coordinate system.
If a new series is sent while in this step, it will replace the existing series and clear all annotations.
While detecting the AC, PC, and MSP points, the UI can be disabled.
If additional data belonging to the current 3D MR series is sent, the AC, PC, and MSP points can be re-calculated automatically.

The AC, PC and MSP locations can be identified in any suitable manner. In some embodiments, the AC-PC step can have an automatic, electronic AC, PC MSP Identification Library. The AC, PC and MSP anatomical landmarks define an AC-PC coordinate system, e.g., a Talairach-Tournoux coordination system that can be useful for surgical planning. This library can be used to automatically identify the location of the landmarks. It can be provided as a dynamic linked library that a host application can interface through a set of Application Programming Interface (API) on Microsoft Windows®. This library can receive a stack of MR brain images and fully automatically locates the AC, PC and MSP. The success rate and accuracy can be optimized, and typically it takes a few seconds for the processing. The output is returned as 3D coordinates for AC and PC, and a third point that defines the MSP. This library is purely computation and is typically UI-less. This library can fit a known brain atlas to the MR brain dataset. The utility can be available in form of a dynamic linked library that a host application can interface through a set of Application Programming Interface (API) on Microsoft Windows®. The input to this library can contain the MR brain dataset and can communicate with applications or other servers that include a brain atlas or include a brain atlas (e.g., have an integrated brain atlas). The design can be independent of any particular atlas; but one suitable atlas is the Cerefy® atlas of brain anatomy (note: typically not included in the library). The library can be configured to perform segmentation of the brain and identify certain landmarks. The atlas can then be fitted in 3D to the dataset based on piecewise affine transformation. The output can be a list of vertices of the interested structures.

In some embodiments, the mid-sagittal plane (MSP) is approximated using several extracted axial slices from the lower part of the input volume, e.g., about 15 equally spaced slices. A brightness equalization can be applied to each slice and an edge mask from each slice can be created using a Canny algorithm A symmetry axis can be found for each edge mask and identify the actual symmetry axis based on an iterative review and ranking or scoring of tentative symmetry axes. The ranking/scoring cam be based on whether a point on the Canny mask, reflected through the symmetry axis lands on the Canny mask (if so, this axes is scored for that slice). An active appearance model (AAM) can be applied to a brain stem in a reformatted input stack with the defined MSP to identify the AC and PC points.

The MSP plane estimate can be refined as well as the AC and PC points. The MSP plane estimate can be refined using a cropped image with a small region that surrounds a portion of the brain ventricle and an edge mask using a Canny algorithm. The symmetry axis on this edge mask if found following the procedure described above. The AC and PC points are estimated as noted above using the refined MSP and brightness peaks in a small region (e.g., 6×6 mm) around the estimate are searched. The largest peak is the AC point. The PC point can be refined using the PC estimate above and the refined MSP. A Canny edge map of the MSP image can be computed. Again, a small region (e.g., about 6 mm×6 mm) can be searched for a point that lies on a Canny edge and for which the image gradient is most nearly parallel to the AC-PC direction. The point is moved about 1 mm along the AC-PC direction, towards PC. The largest intensity peak in the direction perpendicular to AC-PC is taken to be the PC point.

TABLE 2C

Plan Entry - Target Step Description

The application can provide the ability to save position coordinates as default values for the STN and Gpi targets. Initially these default values are set to 0, 0, 0.
Saved values can appear as the default for subsequent procedures using that target.
The application can also provide custom targets for which no default coordinate is supplied. When this option is selected, the user will be able to define a set of custom-named targets associated with a single entry point.

TABLE 2C-continued

Plan Entry - Target Step
Description

The application can display anatomic coronal, sagittal, and axial views.
Target points can be editable in any MPR view in this step.
The application can provide functionality to automatically register a brain atlas to the patient volume and generate outlines of structures associated with the selected target and display corresponding contours on the MPR views.
The application can provide interface to manually scale and offset the brain atlas registration to better match observed patient anatomy.

TABLE 2D

Plan Entry - Trajectory Step
Description

For each given target point, the user can specify the corresponding entry point.
The application can display oblique reformatted coronal, sagittal, and axial views aligned to the proposed trajectory.
Entry points can be editable on either the oblique sagittal or coronal viewports in this step.
The oblique axial view can provide cine functionality to animate a fly-through along the trajectory.
The application can also provide an anatomical axial view.
The respective positions of the anatomical and oblique axial views can be represented by lines on the oblique sagittal and coronal views.
When multiple targets (custom targets) have been defined for an entry point, the application can provide means to select the current target to display. Edits to the entry point will change the entry point for all associated targets.
If the user attempts to set the trajectory such that the probe could not be inserted without striking the bore an error can be shown and the trajectory will not be set. This makes use of the bore size typically entered on the Start step.
The application can provide means to define named trajectories within the step. Trajectories from the list of named trajectories may be selected for display in the step.
If the user moves the entry point off the edge of the grid, warning text will be shown.

TABLE 2E

Plan Entry - Grid Step
Description

The application can display a volumetric 3D view showing the planning volume. For a bilateral procedure 2 such views can be shown, the left side in the left viewport, the right in the right viewport.
The application can optionally display the grid coordinates of the marking grid.
The application can optionally display overlay graphics to visually identify edges and positions within grid squares.
On each view, the application can display the corresponding entry point
The application can automatically align the 3D views such that the user's point of view is looking along the trajectory from the entry towards the target. In the case of multiple custom targets, the trajectory to the first target can be used.
The application can set the visualization parameters of the volume such that the grid itself is visible to the user. The initial zoom level can ensure that the entire head is visible.

At this point, holes have been burred at the entry points and the trajectory guides 50*t* have been attached. NOTE: Because the patient has been moved, points defined in the previous image coordinate system may no longer be valid. Also, brain shift may occur at this point.

TABLE 2F

Plan Target - AC-PC Step
Description

The Plan Target AC-PC step can look and function the same as in the planning AC-PC step. However, data received in this step can be stored as the replanning volume. The AC, PC, and MSP annotations and the resultant transformation derived from the replanning volume can be kept distinct from those determined in the planning AC-PC step.

TABLE 2G

Plan Target - Target Step
Description

The Plan Target Step can function the same as in the planning step but with additional functionality to support slab data fusion.
The Plan Target Step can accept DICOM slab data.
While receiving slab data, the UI can be disabled and a message should be shown to indicate that a data transfer is in progress.
The Plan Target Step can provide a thumbnail bar that lists series in their order of acquisition. Selecting a series in the thumbnail bar will cause it to appear fused with the re-planning volume. Selecting the Plan Target volume can cause it to be displayed by itself.
Fused data can appear in the viewports along with the - plan target volume images and will be positioned and scaled to exactly coincide with the position and scale of the plan target volume.
The control panel can contain a slider that controls the relative intensity of the two series in the blended viewports.
The step can display scan plane parameters for an anatomical axial slab through the current target.

TABLE 2H

Plan Target - Trajectory Review Step
Requirement description

The Plan Target Trajectory Review Step can function the same as the Planning Trajectory review step with only the following exceptions:
    Slab fusion support
    Segment out the pivot point from frame
    markers
    Use pivot point position as a fixed entry
    point (not editable)
The Plan Target Trajectory Step can accept DICOM slab data.
While receiving slab data, the UI can be disabled.
The Plan Target Trajectory Review Step can provide a thumbnail bar that lists series in their order of acquisition. Selecting a series in the thumbnail bar will cause it to appear fused with the re-planning volume. Selecting the re-planning volume can cause it to be displayed by itself.
Fused data will appear in the viewports along with the volume images and will be positioned and scaled to exactly coincide with the position and scale of the re-planning volume.
The control panel can contain a slider that controls the relative intensity of each series in the blended viewports.
If for any reason the software is unable to identify the frame markers to find the pivot point, a warning can be displayed.

TABLE 2H-continued

Plan Target - Trajectory Review Step
Requirement description

The step can display scan plane parameters for:
    an oblique sagittal slab along the trajectory
    an oblique coronal slab along the trajectory
The step can display the trajectory angles relative to the
anatomical coronal and sagittal planes.

TABLE 2I

Navigate - Initiate
Description

The step can prompt the user to acquire a small high-
resolution slab through the proximal canula at a distance
such that it will show a cross-section of the proximal
canula even at maximum angulation and maximum
offset. The slab can have a minimum of 4 slices.
(Example: given a canula 83 mm long, a maximum
angulation of +/−35 degrees, and a maximum offset of
4 mm, then a scan plane 65 mm up from the distal canula
marker will be sufficient to ensure that the canula is
visible in the slab.)
The application can also prompt the user to acquire a
small high resolution slab scan with the following
attributes:
    plane aligned to the plane of the frame markers
    (this can be based on the frame segmentation that
    was done for the trajectory review step)
    plane center is positioned at the mechanical
    center of rotation
    slab thickness is large enough to include all of the
    distal canula marker even under maximum
    angulation and offset (Example: given a maximum
    angulation +/−35 degrees, a maximum offset of 4
    mm, and distal canula marker size of 7.1 mm, the
    total thickness required would be 11.6 mm, so any
    larger value may be used, say 13 mm)
    slice spacing can be about 1 mm
The application can identify the positions of the proximal
and distal canula.
Using the detected positions of the frame markers in the
plan target volume, the application can compare the
observed position of the distal canula with the
mechanical center of rotation. Since a locking pin may be
used to ensure that there is no offset, values above a low
threshold can cause a warning to be displayed.
(Example warning text: "Distal canula marker not found
at expected location. Verify that canula is locked in
'down' position and reacquire distal canula scan.")
If no pivot point marker can be identified, the user will be
prompted to verify that the canula is locked in the 'down'
position and re-acquire the slab scan.
The step can provide 3 MPR viewports in which to
display the acquired slabs. These viewports will be
oriented such that their base planes are aligned to the
detected canula axis.
The step can provide a thumbnail bar to allow the user to
select which acquired slab to display.

TABLE 2J

Navigate - Alignment
Description

The application can prompt for an alignment scan with
the following attributes:
    scan plane is perpendicular to planned trajectory
    scan plane is centered around the trajectory
    scan plane position is set such that a cross-
    section of the proximal canula will be shown even
    at maximum angulation and maximum offset.
    a single 2D image can be acquired
The application can display an anatomical axial view
through the currently selected target.
The user may opt to switch the display to show a
trajectory-axial view.

TABLE 2J-continued

Navigate - Alignment
Description

On receiving a 2D image of the top of the canula, the
application can automatically identify the position of the
top of the canula in 3D space. Using this position and,
previously-determined pivot point, and the previously-
determine offset, the application can draw an annotation
representing the intersection of the current trajectory with
the image plane containing the planned target.
This step can display lines from the current projected
target to the planned target that indicate the track the
projected target would travel if the pitch and roll wheels
were turned independently. These lines can be colored
to match colors on the control wheels for pitch and roll
respectively. A tool-tip (e.g., pop-up) can provide text to
describe the suggested action.
(For example: "Turn Roll knob to the Left")
On re-calculating the projected target point, an error
value can indicate the in-plane linear distance between
the projected target point and the planned target point on
the currently-displayed plane.
Images that are not oriented correctly to the requested
scan plane can result in a warning. In this case,
annotations and error measurements may not be
displayed.
Images in which the targeting canula cannot be identified
can result in a warning. Annotations and error
measurements may not be displayed.
When multiple targets have been defined for an entry
point, the application can provide means to select the
current trajectory to display.
When drawing the target and the current projection of the
canula path, the annotations can be drawn to match the
physical size of the probe diameter.

TABLE 2K

Navigate - Insertion
Description

The application can provide a depth value to set on the
depth stop prior to insertion.
The application can prompt with scan parameters for
oblique coronal and sagittal planes aligned to the
trajectory. Also for an oblique axial perpendicular to the
trajectory.
On receiving coronal or sagittal images, the application
can display an overlay graphic indicating the planned
trajectory. The most recent coronal and sagittal images
can appear together in a 1 × 2 display.
On receiving a trajectory axial scan perpendicular to the
trajectory, the application can segment out the cross-
sections of the probe to determine the actual path being
followed by the probe.
On receiving a trajectory axial scan perpendicular to the
trajectory, the application can display two viewports
containing:
    the axial stack with graphic overlays showing the
    detected path of the probe on each image
    an anatomic axial view through the target showing
    the planned target and the target projected from
    the detected path of the probe. An error value can
    show the distance between the current projected
    target and the planned target.
If multiple trajectories have been defined for a single
entry, the application can display the trajectory that is
currently aligned during insertion.
On entering the insertion step, the application can
instruct the user to ensure that if they are using an
imaging probe that it is connected to the scanner as an
internal coil. Failure to do so could cause heating of the
coil and injury to the patient. The user must explicitly
click a button to acknowledge that they understand the
warning.

TABLE 2L

Refine - Target
Description

The step can prompt for either i) a high-resolution 2D image to be acquired using the imaging probe or ii) a high-resolution slab through the target area. The associated scan plane parameters can specify a trajectory axial image centered on the target.
The application can provide means to identify the tip of the probe (or stylet), and provide an error value for the linear distance from the probe to the planned target point in the axial anatomic plane.
The application can provide UI to set an updated target point.
The user may opt to proceed to the X-Y Adjustment step, return to Alignment to align to another target, or advance to the Admin step.
On accepting the current position, the user can be shown a warning not to scan once the MR-incompatible DBS leads (if they are incompatible or potentially incompatible) have been placed. For bilateral cases, the user proceeds to complete the insertion of the probe on both sides before placing the leads. The message can indicate that scanning with MR-incompatible leads may result in serious injury or death.
If the user modifies a target point, the step can prompt the user to confirm removal of the offset locking pin from the targeting frame before going on to the next step.

In the event that the placement is not acceptable, the user may opt to proceed to the X-Y Adjustment workflow step.

TABLE 2M

Refine - Adjust X-Y Offset
Description

The X-Y Adjustment step can display the current target and projected point as annotations to the image data that was acquired during the Target Refinement step.
This step can prompt the user to acquire 2D images with scan plane parameters such that the image lies perpendicular to the trajectory and through the pivot point.
On receiving a 2D image through the pivot point, the step can calculate the current projected target and display an annotation on the 2D image from the imaging probe.
This step can display lines from the current projected target to the revised target that indicate the track the projected target would travel if the X and Y offset wheels were turned independently. The lines can be colored to match colors on the control wheels for X and Y offset respectively. A tool-tip (e.g., pop-up) can provide text to describe the necessary action.
(For example: "Turn X-offset knob to the Left")
This step can display an annotation indicating the location of the original planned target.
When drawing the target and the current projection of the canula path, the annotations can be drawn to match the physical size of the probe diameter.

TABLE 2N

Refine - Insertion
Description

After completing the X-Y Adjustment, the application can provide a workflow step to guide insertion. This is substantially the same as the first instance of the Insertion step above.

TABLE 2O

Refine - Lead Placement
Description

After probe has been placed (or both probes for bilateral case) and position has been accepted by user, the user may proceed to the lead placement step.
This step can provide the user with the depth values for the placement of the leads.
This step may advise the user that once leads have been placed scans may not be performed because heating in the leads could cause injury or death to the patient.

TABLE 2P

Admin Step
Description

The step can provide means to archive data relating to the procedure. This includes:
    trajectory planning data
    log files with case data
    image data
The step can provide functionality to automatically generate a report documenting the performed procedure. This report can include:
    patient information
    AC, PC, and MSP points in MR space (Both detected and user-specified, if user modified.)
    Planned and corrected targets in both MR and ACPC space
    elapsed time for the procedure
    physician case notes (optional)
    any screenshots taken during the procedure
An anonymous version of the report can also be generated automatically with the patient name and id removed.
The step can provide UI whereby the user can:
    selected a target
    specify a position in MR coordinates representing the lead tip
    define a set of offsets indicating the electrode offsets from the lead tip
For each offset value, the step can find provide the ACPC coordinate that corresponds to a point offset from the tip position back along the trajectory of the lead. These values correspond to the electrode positions in ACPC space. These values may be added to a patient report.
The Admin step can include a button to shut down the application on completion of the procedure. The user may not be allowed to otherwise close the application.
The application can have a configuration value to specify whether all patient data is to be cleared from the system on shut down.

Again, it is noted that functional patient data can be obtained in real-time and provided to the circuit 30c/workstation 30 on the display 32 with the visualizations of the patient anatomy to help in refining or planning a trajectory and/or target location for a surgical procedure.

When displaying images or visualizations that were created with the imaging probe 50a (FIG. 5, where used), the circuit 30c may electronically apply a (sigma) correction to correct for a 'volcano' or 'halo' shaped intensity distortion. That is, in some particular embodiments, the imaging probe antenna or coil may introduce a distortion in the images that are created with it that may be described as a bright halo around the probe itself where it appears in the image. Thus, when images from the imaging probe have such a feature, the circuit 30c can be configured to electronically automatically apply a correction to cancel out the halo (or at least reduce it). This feature will only affect the small field, high-resolution images that are created via the imaging probe itself. Images obtained using the main head coil do not typically have such a distortion.

Figure 14A:
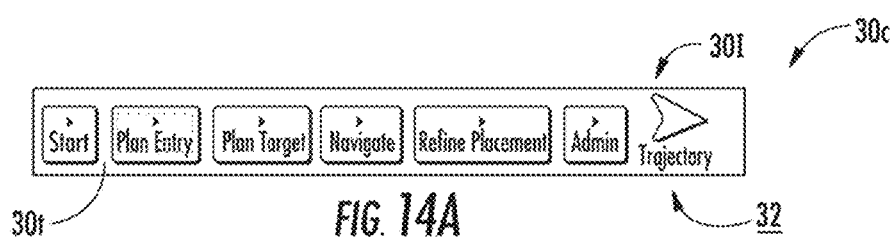
FIGS. 14A and 14B are illustrations of a User Interface (UI) tool bar with exemplary workflow groups according to embodiments of the present invention.
Figure 14B:
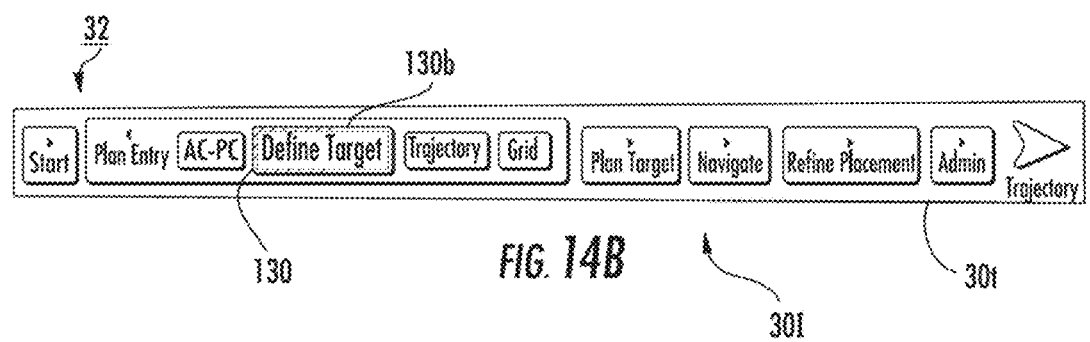

Referring to FIG. 14A, the circuit 30c can be configured with a single control tool bar 30t that is displayed on the display 32 that allows the user to select what group and step to go to and also shows which groups and steps have been completed. FIG. 14B shows an example of the workflow control tool bar 30t with the "Plan Entry" group selected, and the "Define Target" enlarged as the current step. The tool bar 30t can include a color border 130 that can be used to partially or totally surround a button 130b to illustrate completion of a step. For bilateral procedures, the border can be color enhanced on one side when a task for that side is completed, e.g., on the left side when the left target is complete in the Define Target step.

As the user works through the procedure, certain clinical information is stored to be incorporated into a procedure report that may be reviewed at the end of the procedure and/or archived as a patient record. The circuit 30c can be configured to provide a user interface (UI) 30I that provides viewing tools, such as one or more of the following features.

Figure 15:
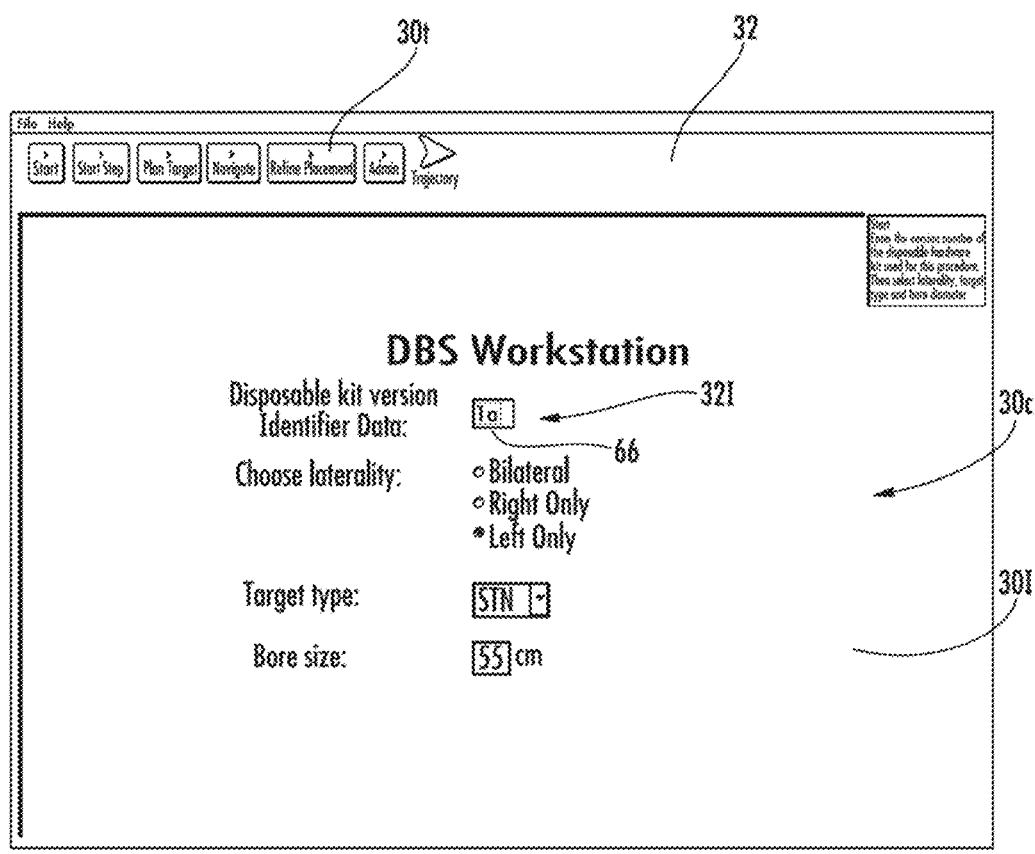
FIG. 15 is a screen shot of an exemplary (e.g., DBS) workstation Start window for a workstation display according to embodiments of the present invention.

Draw measurement lines
Pan view
Zoom, Zoom All, Zoom to Region, Zoom to Point
Magnifying glass
Show/Hide Annotations
Show/Hide Crosshairs
Drag views between panels
Resize view panels
Maximize view to a 1×1 display
Save screen capture (can be added to the report)
Reset view settings to default FIG. 15 is a screen shot of an exemplary UI 30I for the Start Group which may conveniently be configured as a one-screen input to set overall procedure parameters such as laterality, target type and MR Scanner bore size (recognizing that open bore MRI Scanner systems may also be used). Instead of bore size, a drop-down list can be provided that allows a user to select a manufacturer and type of MR Scanner in use that provides the associated bore size. Of course, the system 10 can be configured as an MR Scanner-specific system or the MR Scanners of the future may have a standard bore size or be configured so that bore size is not a constraint and this information may not be required. As shown, the UI 30I can also include an input 32I that requires entry of hardware identifier data 66, shown as disposable kit version input, as discussed above with respect to FIG. 5. In order to assure hardware and software compatibility and/or proper operation, if the identifier data 66 does not match, the system 10 can be configured to not allow a user to proceed to a next step or may prompt the user for other key codes.

Bore size is used in the step Plan Entry/Trajectory. If the user selects a trajectory such that the probe cannot be inserted into the canula 60 because it will not physically fit inside the scanner bore, a warning is generated (visual on the display 32 and/or audible). See Plan Entry/Trajectory step above.

Figure 16:
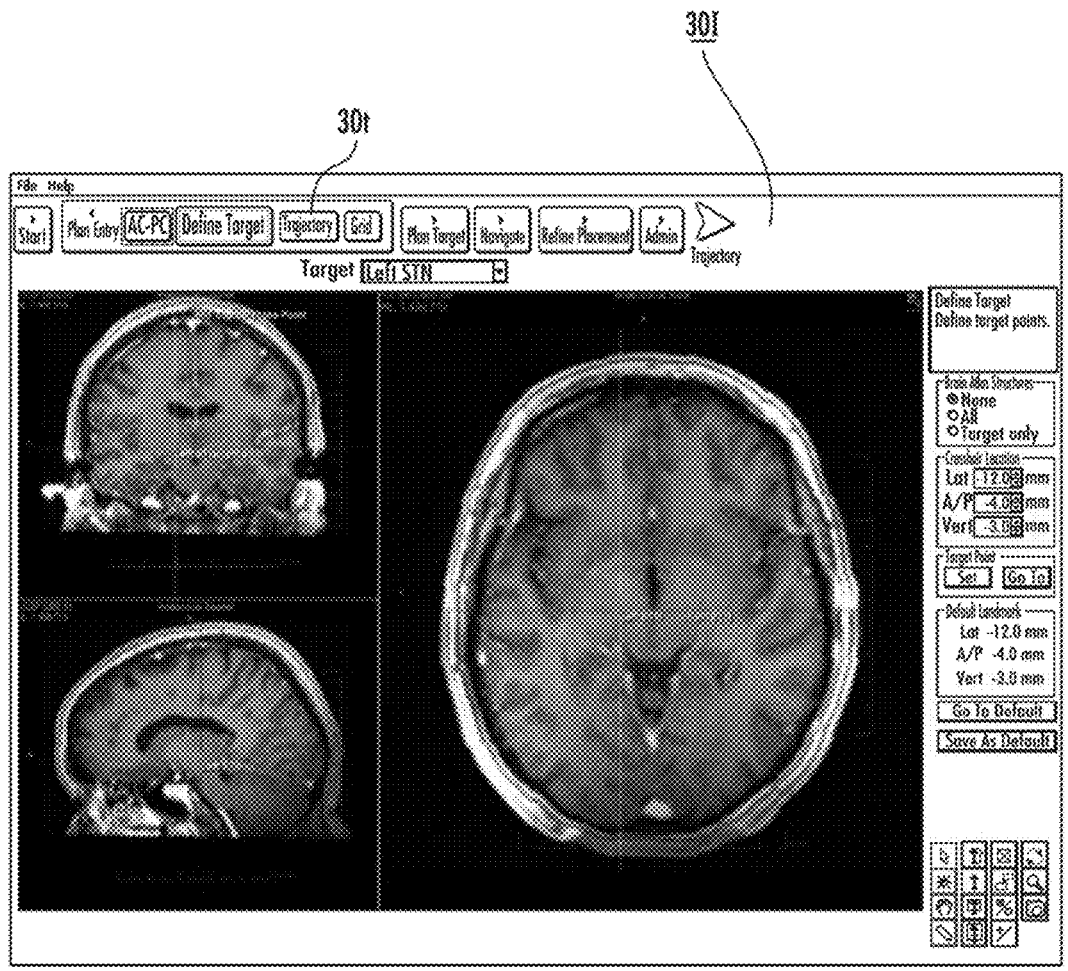

FIG. 16 is a screen shot associated with an exemplary UI 30I with a Plan Entry workflow group for a Define Target step (shown as left STN) illustrating the toolbar 30t and cross hair location data with default landmarks with patient image data. This step can be used to establish the AC PC coordinate system. On receiving a whole-head volume, the step can automatically find candidates for these points. The user is to review and correct these points if necessary. The user can either position the crosshairs at a point and "click" the 'Set' button to set the desired annotation, or they can drag an existing annotation around on the screen. Once points are defined, view planes can automatically reformat to align them to the ACPC coordinate system to show the anatomical planes: Coronal, Sagittal, and Axial. Any subsequent edit to the landmarks can cause the view planes to instantly re-align to match.

Figure 17:
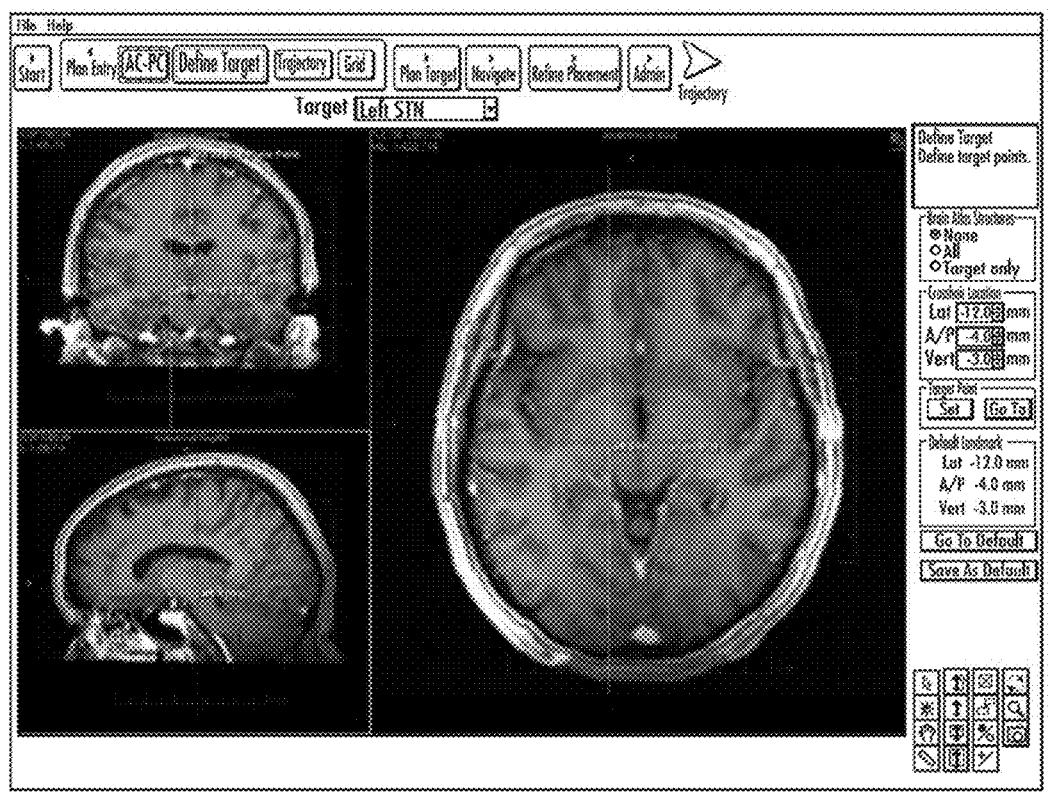
Figure 18:
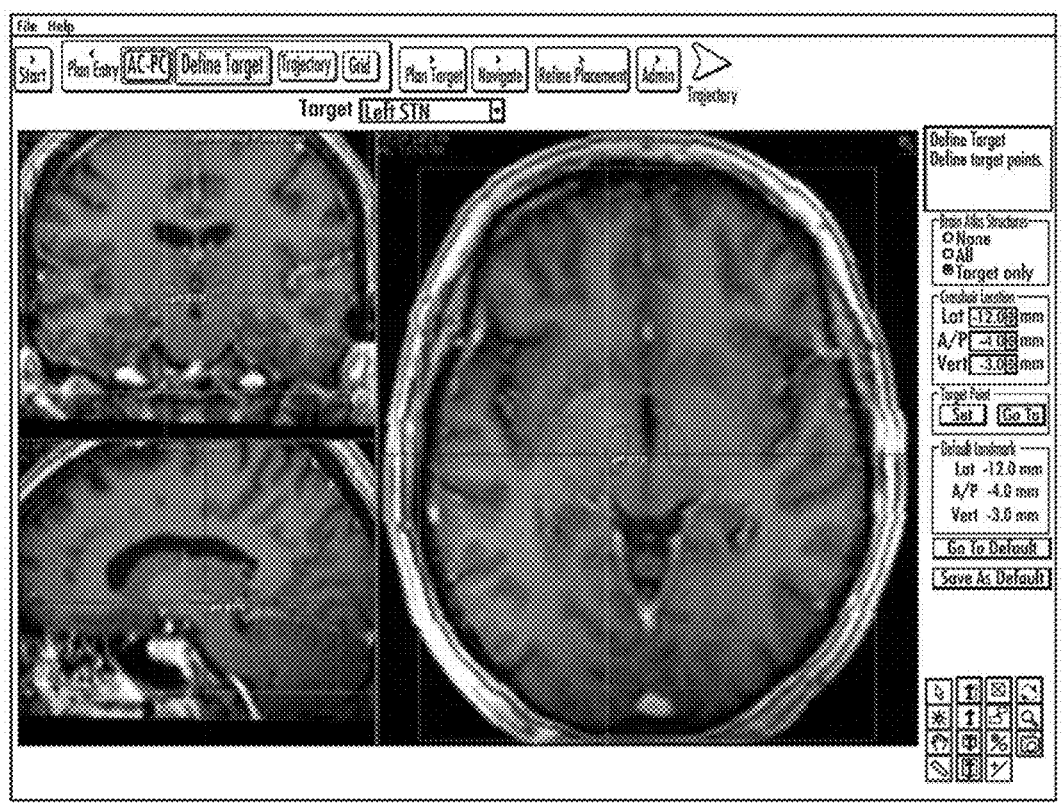
Figure 19:
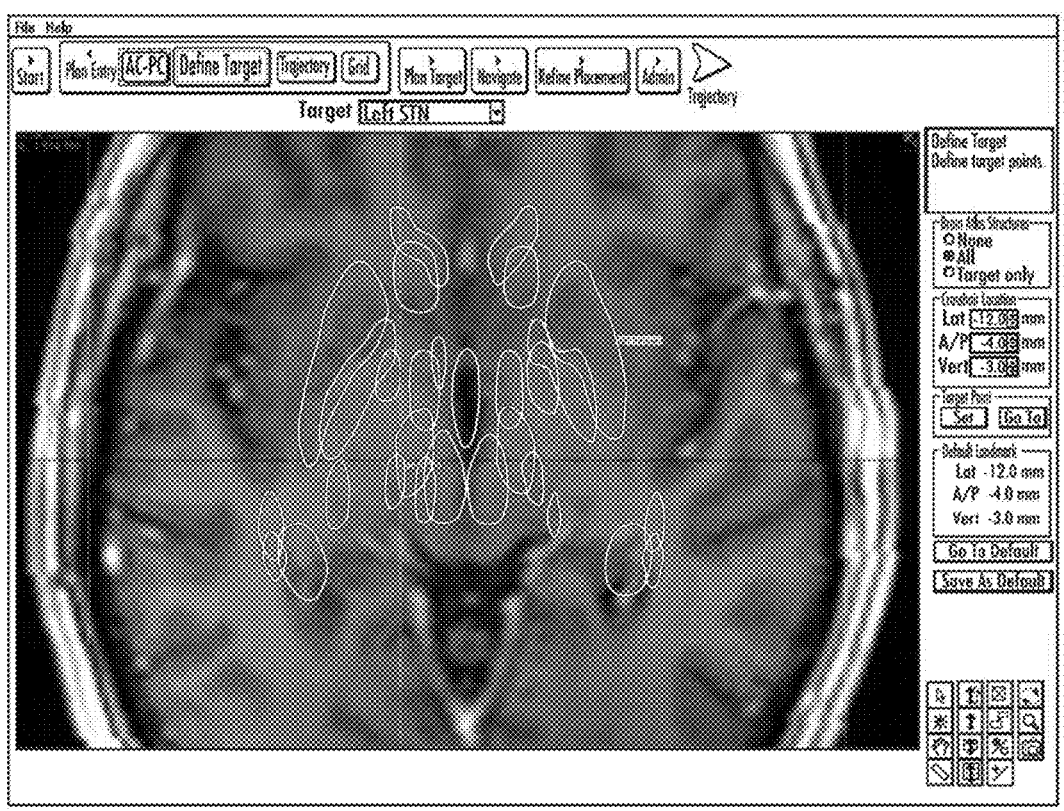

FIG. 17 illustrates another exemplary screen shot for a Define Target step which is used to set target points so that the trajectories through potential entry points can be investigated in the next step. The user may opt to overlay the outlines from a standard brain atlas over the patient anatomy for comparison purposes which may b provided in color with different colors for different structures. FIG. 17 shows the play entry of the Define Target step with no atlas. FIG. 18 illustrates the UI with an atlas showing a target outline in three orthogonal views and FIG. 19 illustrates an atlas showing structures in a 1×1 layout. The view planes show the anatomical planes as defined in the ACPC step. Target points are edited similarly to how the ACPC points are edited. For the bilateral case, once the target has been defined for one side, then when the user selects the target for the other side, the crosshairs will automatically jump to the mirror-image position. If the patient has symmetric anatomy, this will save time in finding the equivalent position. When using the brain atlas, the user may opt to show either just the target structure (STN or GPi) or all structures. In either case, a tooltip (e.g., pop-up) can help the user to identify unfamiliar structures. The user may also opt to scale and/or shift the brain atlas relative to the patient image to make a better match. To do this, the user may drag the white outline surrounding the brain atlas template. Fiber track structures and/or functional information of a patient's brain can be provided in a visually prominent manner (e.g., color coded or other visual presentation) for a surgeon's ease of reference. This information can also be selected or suppressed from views via a UI selection 32F (e.g., toolbar option) as shown in FIG. 4.

Figure 20:
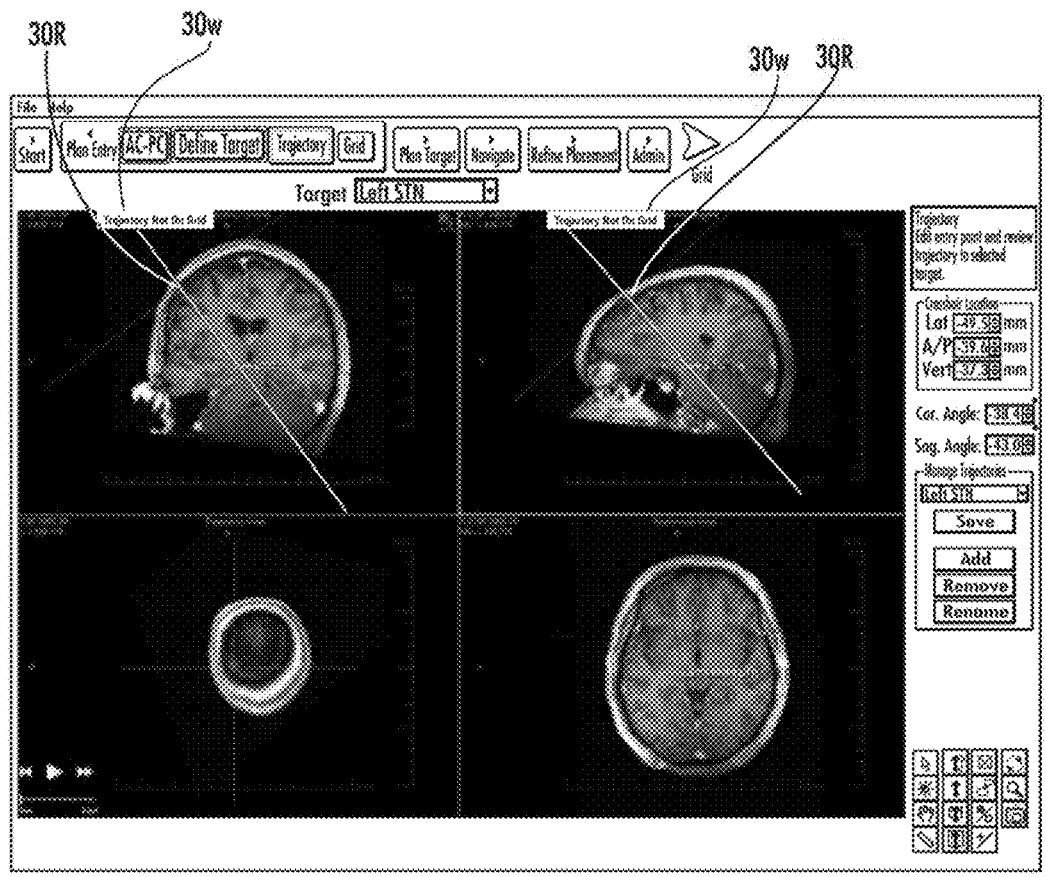
FIGS. 20 and 21 are examples of operational warnings provided to a workstation/display that can be automatically generated by the system according to some embodiments of the present invention.

FIG. 20 is a screen shot of an exemplary screen display for a Trajectory step in the Plan Entry workflow group. This step is used to find a clinically viable trajectory that determines the entry point on the skull typically via a grid such as that provided by the grid patch 50g (FIG. 11). A visual warning can be displayed, e.g., a red warning message 30W on the top of the two top views and a red trajectory line 30R) can be used to indicate that the selected trajectory does not intersect the grid. In operation, upon entering this step, the workstation 30 can automatically search through the image volume for the marking grid(s) 50g. It can be configured to position the initial trajectory such that it runs through the middle of the grid 50g. If the user moves the trajectory such that the entry point is not on the grid, a warning 30W is displayed.

The top two views of FIG. 20 show the coronal and sagittal views aligned along the current trajectory line. The user drags the trajectory line and it rotates freely about the target point. The bottom-left view shows the plane perpendicular to the trajectory at the level of the green line in the coronal and sagittal views. This is the "probe's eye" view. To advance the probe's eye view along the trajectory, in addition to dragging the green line along the trajectory line or using the mousewheel, onscreen VCR-style controls can provide an animated fly-through.

Figure 21:
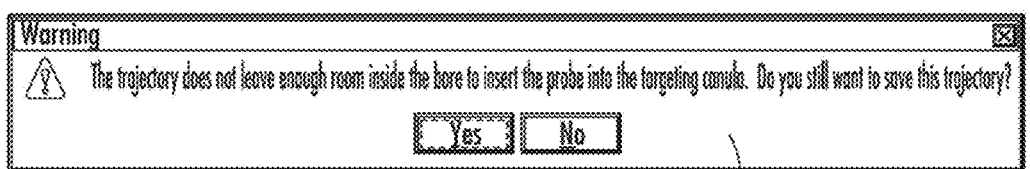

FIG. 21 illustrates a (pop-up) warning 30W' that is automatically generated when a user selects a trajectory that may be blocked by the scanner bore wall. That is, if the user sets a trajectory such that the scanner bore will interfere with the insertion of the probe, a warning is displayed. This calculation is based on the bore size, current trajectory angles, and pre-configured values for the size of the probe 50a/50s/52, canula 60, and frame/trajectory guide 50t (FIG. 5). Similar to the target step, in the bilateral case once the trajectory has been set on one side, the initial default for the other side can be a mirror-image trajectory to start the user closer to a more a likely trajectory. On saving the trajectory, the step automatically finds the surface of the skull along the planned/selected trajectory, identifies the coordinates on the grid and stores that location as the entry point.

Figure 22:
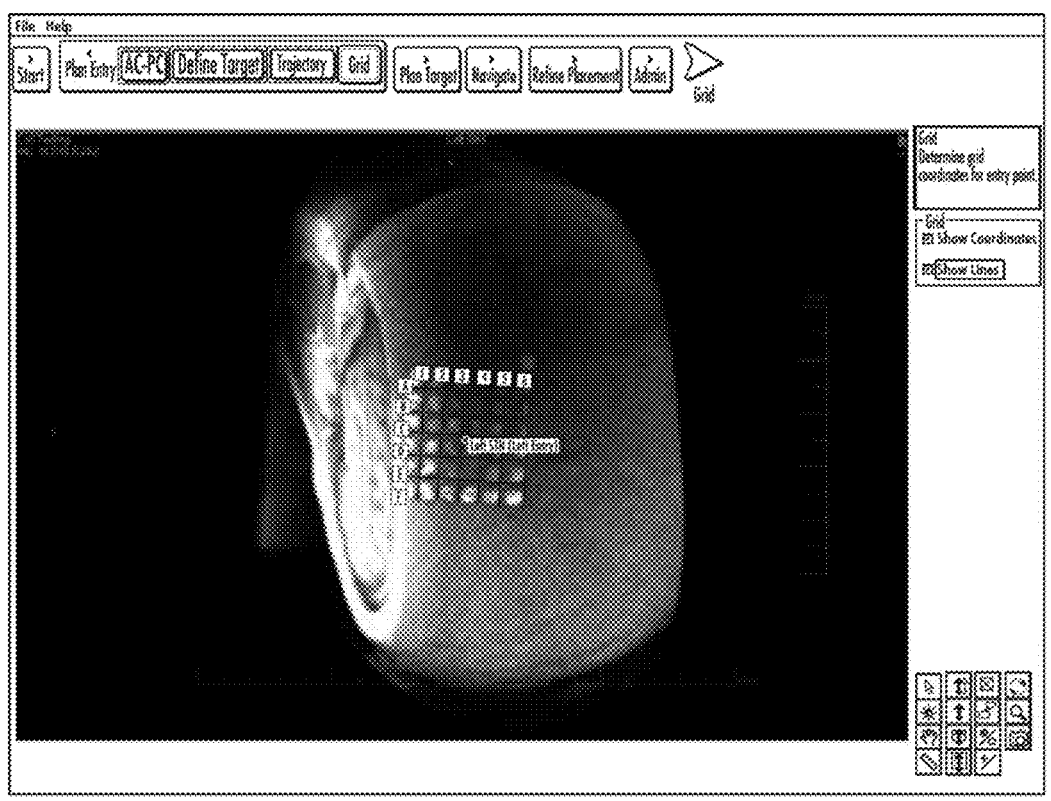
Figure 23:
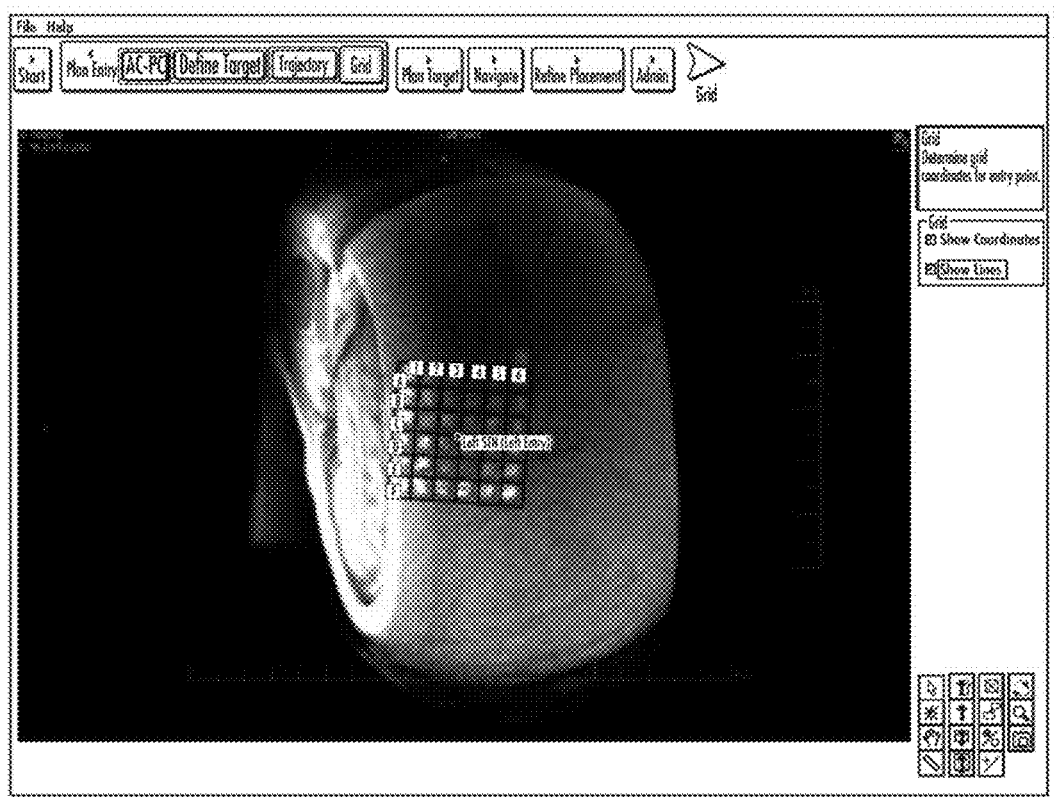

FIG. 22 illustrates an exemplary grid 50g shown overlying a patient's skull on a display 32 (without annotation lines), illustrating coordinates for selecting an entry location (shown as columns 1-6 and rows A-F) with a left STN entry location. FIG. 23 shows the same screen view as FIG. 22 but with optional annotation grid lines. Typically, a user can see the grid coordinates clearly enough that the optional overlay grid lines are not required in order to identify the grid elements. However, in some embodiments, as shown a UI will allow a user to display the lines.

Figure 24:
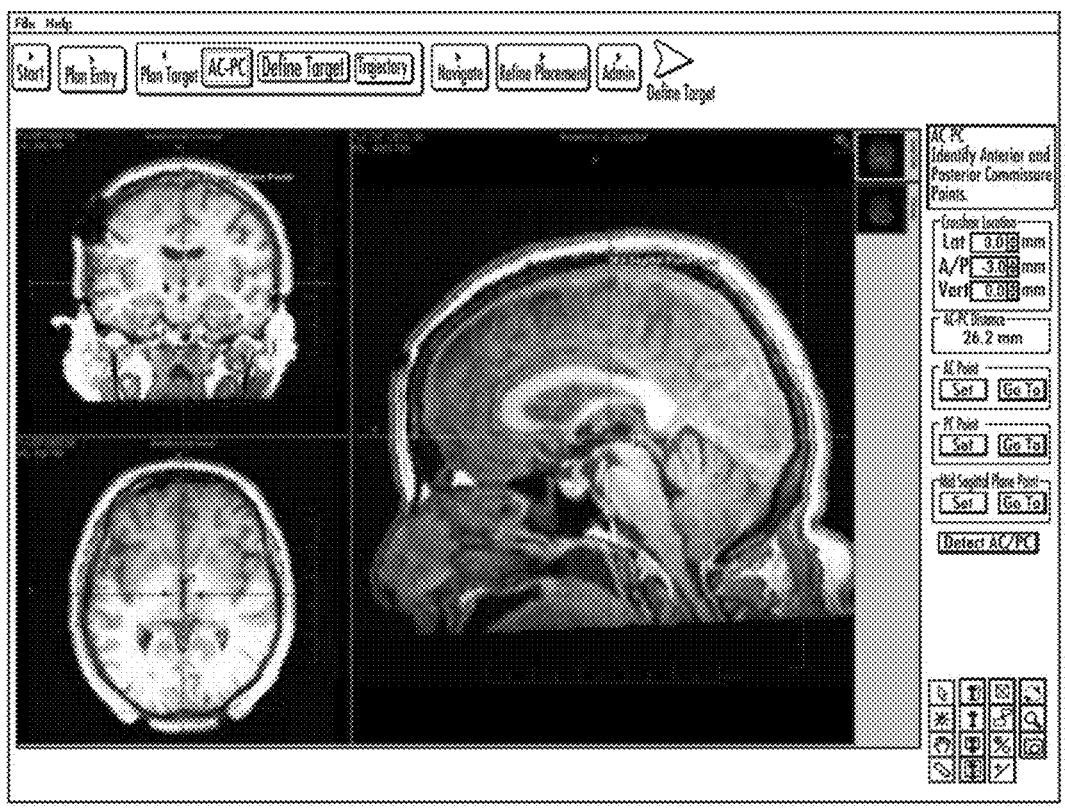
Figure 25:
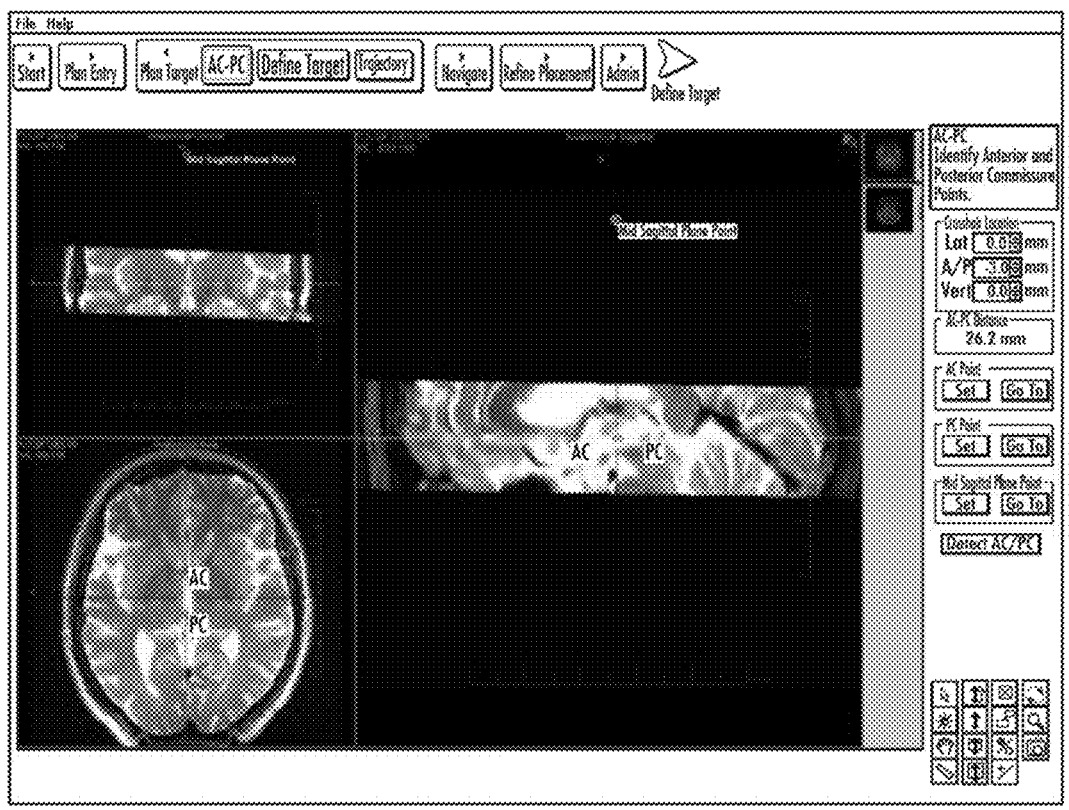

FIG. 24 is an exemplary screen shot of a Plan Target Group workflow with the ACPC step selected. This workflow group is used to precisely determine target points after one burr hole has been formed for a unilateral procedure or both burr-holes have been formed for bilateral procedures (the surgical entries have been burred and the frames attached). Previous planning is typically invalidated by brain shift that occurs with the loss of cerebral spinal fluid pressure. This step is substantially similar to the Plan Entry ACPC step discussed above. The difference is that in addition to the whole-head volume, the user may optionally also send one or more high-resolution slabs containing the ACPC points. The user can use a thumbnail bar to select which data to use to display and edit the ACPC landmarks. FIG. 25 illustrates a screen shot with a Plan Target/ACPC step showing slab data.

Figure 26:
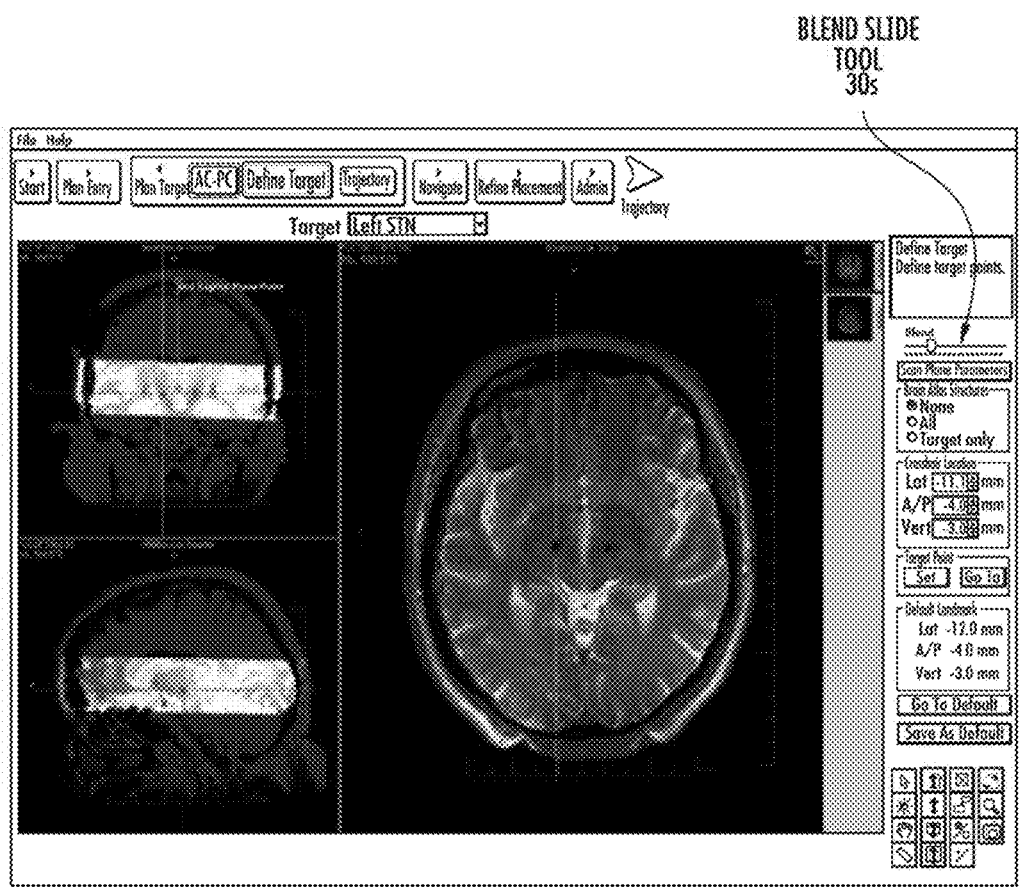

FIG. 26 is an exemplary screen shot of a Plan Target Group workflow with the Define Target step selected. The brain images can be shown with blended volume and slab image data. This step is similar to the Define Target step in the Plan Entry group, but like the preceding step it also supports high-resolution slabs to increase the precision with which the target can be defined. Thus, this step has the ability to show a blended image using data from both the volume and a high-resolution slab. A slider 30S (shown to right under the word "blend") in the UI allows the user to control the ratio of how much of the image comes from either source.

Figure 27:
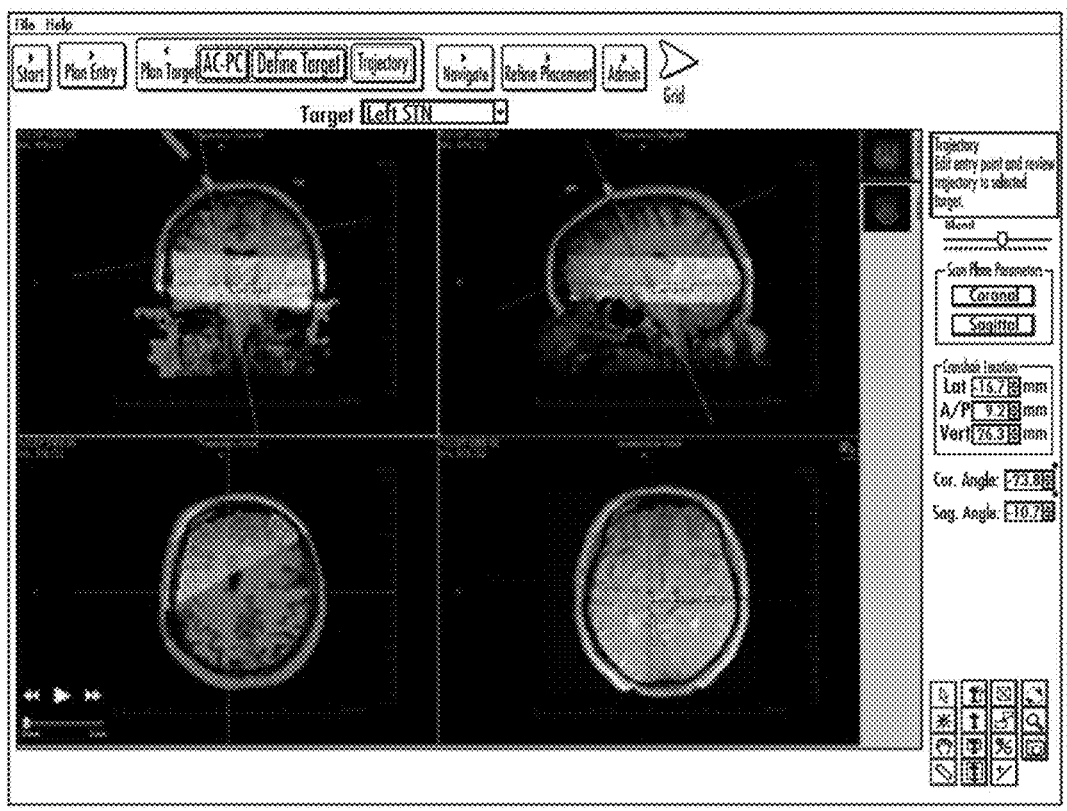

FIG. 27 is a screen shot of a Trajectory step in the Plan Target workflow group. This step is similar to the Plan Entry/Trajectory step, but in this case this step is typically only used to review the trajectory. The entry point cannot be changed since the hole has been burred and the frame attached. Also, like the preceding step, this can support the use of high-resolution slabs and can blend between the volume and the slab. On entering this step, the software can automatically search through the whole-head volume and find the frame marker fiducials. From these, the system 10 and/or circuit 30c can determine the frame locations and orientation and uses this to calculate the actual entry point on the head. This is used along with the target from the previous step to determine the trajectory. Otherwise, the trajectory may be reviewed as described above in the Plan Entry/Trajectory step.

Figure 28:
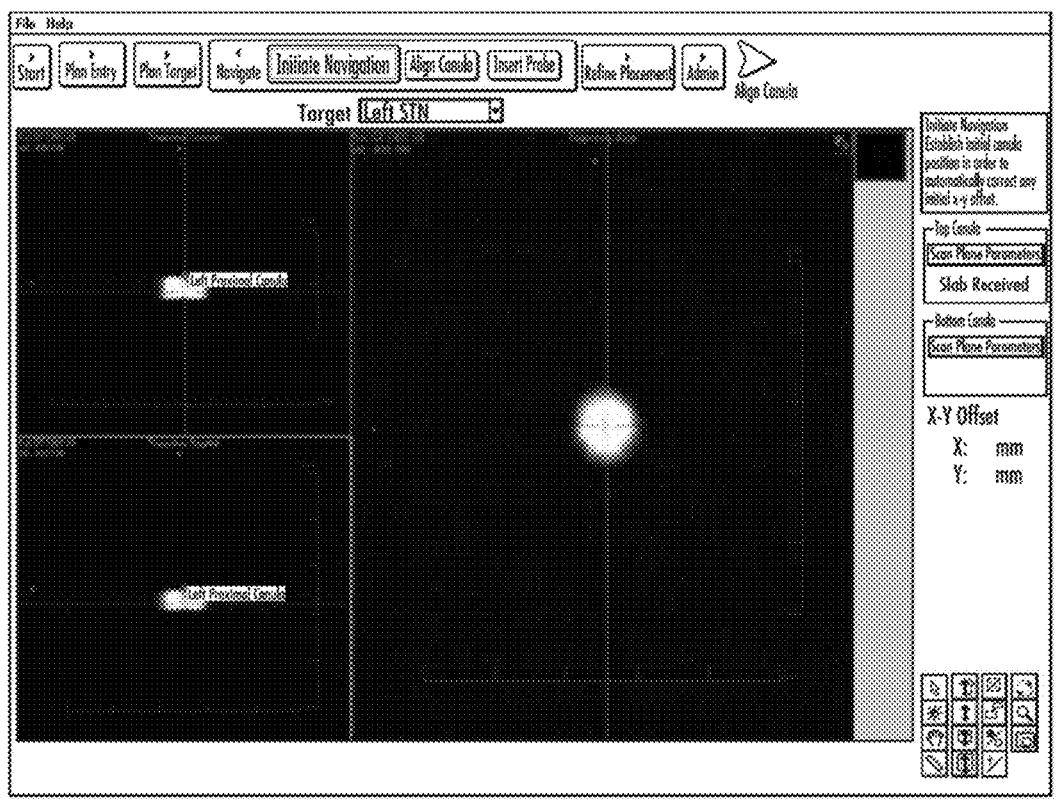
Figure 29:
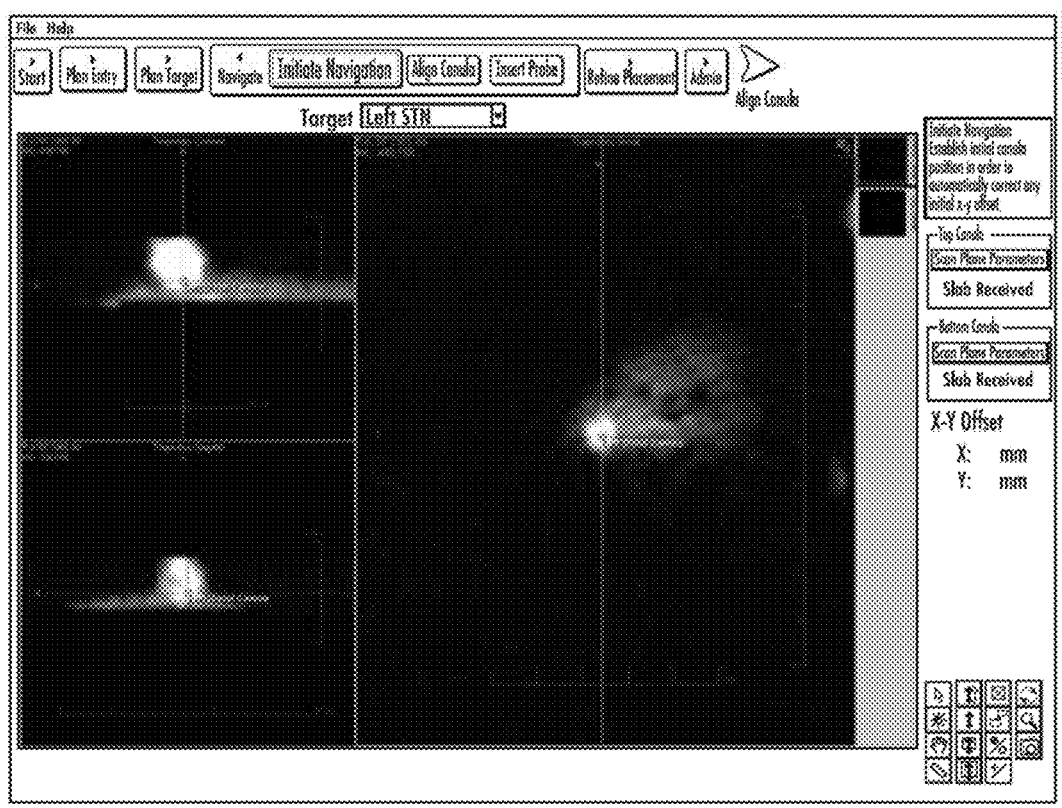

FIG. 28 is a screen shot of a Navigate workflow group with the Initiate Navigation step selected. This visualization shows the proximal canula slab. On entering this group, the user has already burred the entry hole, attached the frame, and finalized their planned targets. This group will guide the user through aligning the canula 60 (FIG. 8) to match the planned trajectory and inserting the probe through the canula to the correct depth. This step is used to determine the initial physical location of the canula. The user acquires a scan through the top of the canula and another through the bottom. The circuit 30c (e.g., software) automatically finds the canula in each slab and determines its position and orientation in space. FIG. 29 illustrates the distal canula slab in the Navigate/Initiate Navigation step.

Figure 30:
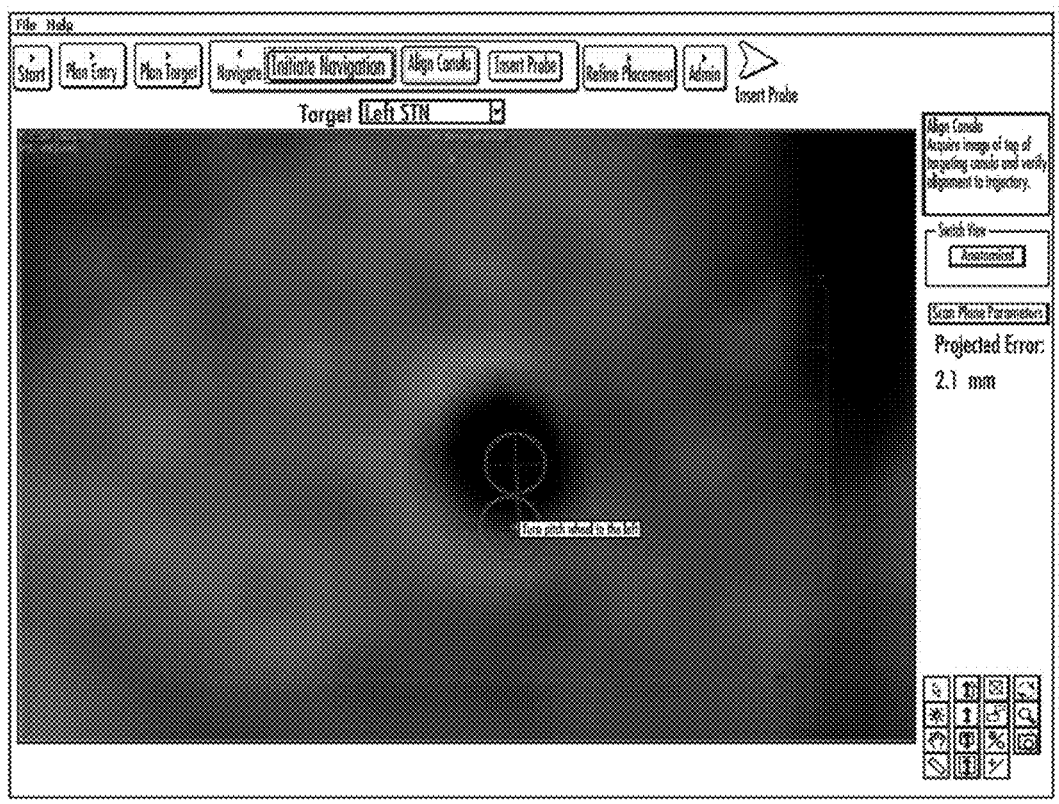

FIG. 30 is a screen shot of a Navigate workflow group with the Align Canula step selected. This step is used to physically align the canula 60 (FIG. 8) to the planned trajectory. The user iteratively adjusts the canula angulation via the pitch and roll control knobs as they rapidly re-acquire an image through the top of the canula 60p. With each update, the circuit 30c (e.g., software) calculates the position of the canula 60 and displays an annotation showing where it's currently pointing on the target plane. FIG. 30 illustrates that user feedback such as a prompt over overlay or a tooltip-style pop-up can tell the user which control to turn and which direction. In some embodiments, as shown, annotations can be drawn as circles corresponding to the probe diameter. The circle with the crosshair is the planned target, the other circle is the current projected point based on the trajectory of the canula. The lines in between show the relative amount of pitch and roll to apply and the text can specify which known to turn and in which direction (shown as "turn pitch wheel to the left").

Figure 31:
Figure 32:
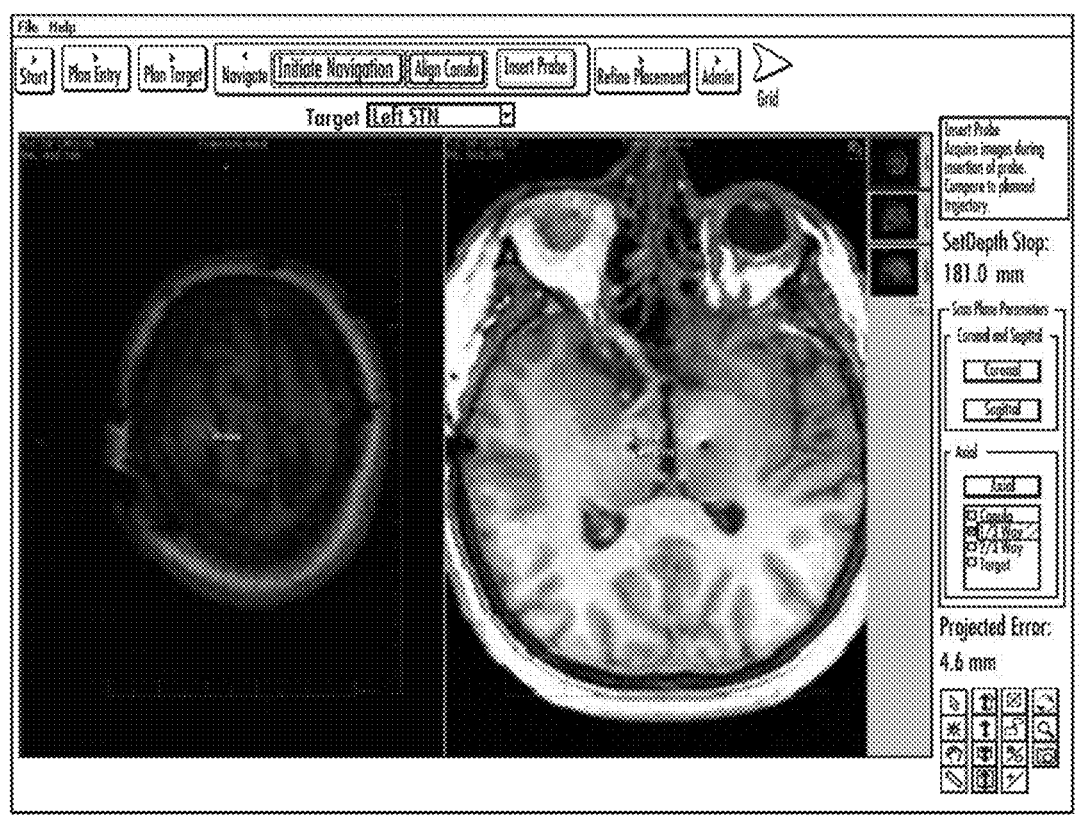

FIG. 31 illustrates a screen shot from an exemplary Navigate/Insert Probe step. This screen shot illustrates coronal and sagittal views to the target (e.g., STN) and can provide a set depth stop dimension (shown on the upper right hand side of the UI). This step allows the user to see how well the probe is following the trajectory as it is inserted. The user may opt to scan Coronal and Sagittal slabs along the probe to visually determine the probe alignment in those planes. The user can also scan perpendicular to the probe. In that case, the circuit 30c (e.g., software) can automatically identify where the probe is in the slab and it then shows a projection of the current path onto the target plane to indicate the degree and direction of error if the current path is continued. FIG. 32 illustrates an axial slab and projected point with a projected error if the current trajectory continues (the probe is shown in the right image offset by 4.6 mm and the offset is also noted on the UI as "Projected Error". The user can perform these scans multiple times during the insertion. The automatic segmentation of the probe and the display of the projected target on the target plane provide fully-automatic support for verifying the current path. The Coronal/Sagittal views can provide the physician with a visual confirmation of the probe path that doesn't depend on software segmentation.

Figure 33:
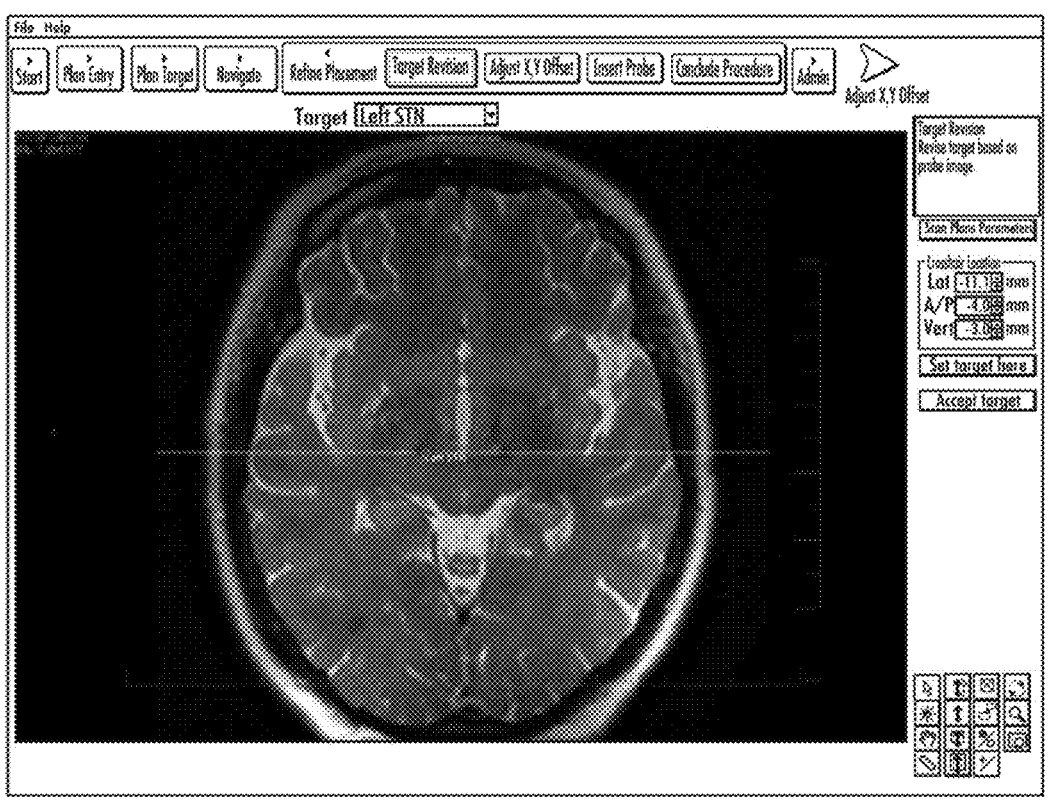

FIG. 33 illustrates an exemplary screen shot of a Refine Placement workflow group with the Target Revision step selected. This step can illustrate the target slab. After completing the initial insertion, the user (e.g., physician) may find that either the placement doesn't correspond sufficiently close or perfectly to the plan, or the plan was not correct. This may be particularly likely if an imaging probe (50a) is used, since a user will be able to more clearly visualize structures like the STN that are usually indistinct with external coils. This workflow group can support functionality whereby the physician can withdraw the probe and use the X and Y offset adjustments to obtain a parallel trajectory to a revised target. This step can prompt the user or otherwise acquire an image slab through the distal tip of the probe. (Optionally, this step may use the imaging probe). The step displays the slab and on it the user may opt to modify the target point to a new location or accept the current position as final.

Figure 34:
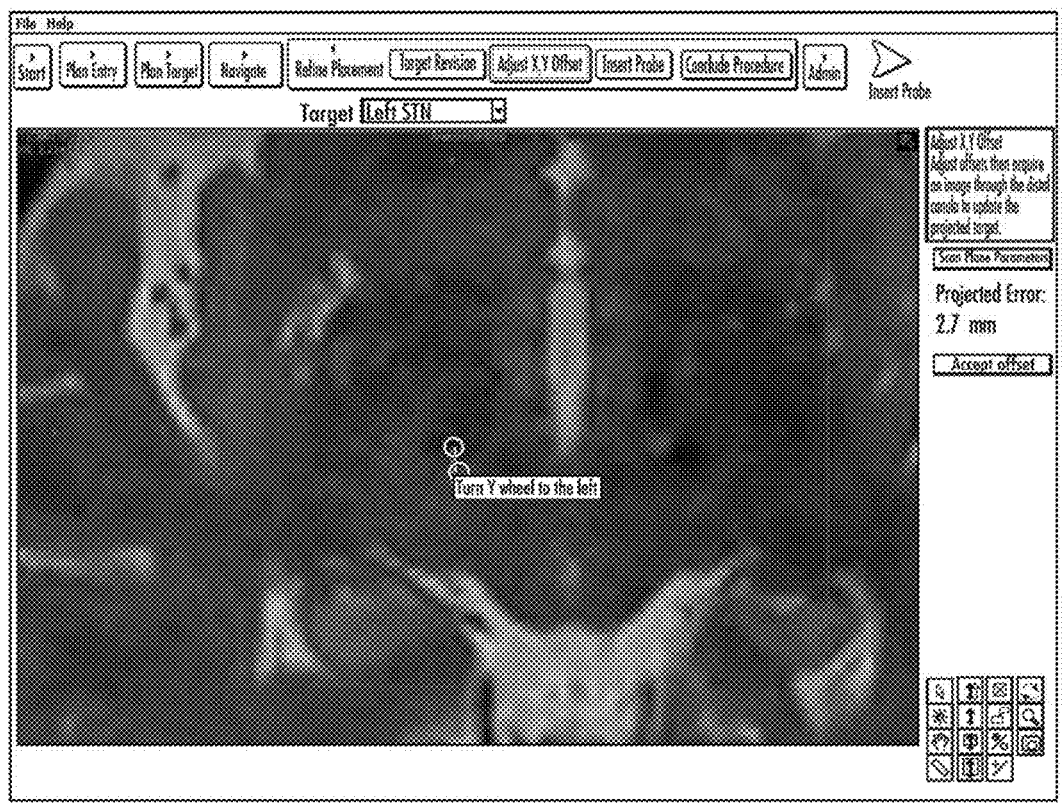
Figure 35:
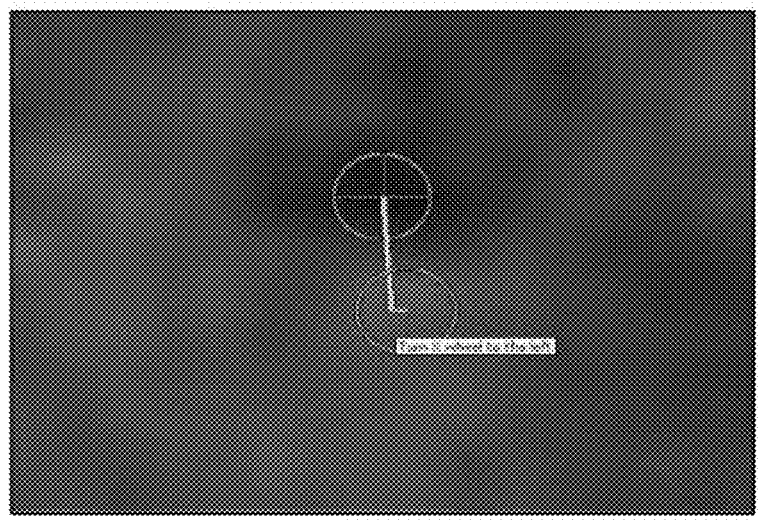

FIG. 34 illustrates an exemplary screen shot of the Refine Placement workflow group with the Adjust X-Y Offset step selected. This step is very similar to the Navigate/Align Canula step described above. The primary difference is that instead of adjusting the angulation of the canula 60, the user is adjusting a small X-Y offset to set the canula 60 to a trajectory parallel to the original one. FIG. 34 shows the display with an visualization f the position of the probe tip relative to the target and with instructions on what physical adjustments to make to obtain the desired parallel trajectory (shown as "turn Y wheel to the right") and the projected error (shown a 2.7 mm). FIG. 35 illustrates a detail of the adjust annotations and pop-up (shown as "turn X wheel to the left").

After the X-Y adjustments are made, the Insert Probe of the Refine Placement workflow group is selected and carried out in the same manner as the Navigate/Insert Probe step described above.

Figure 36:
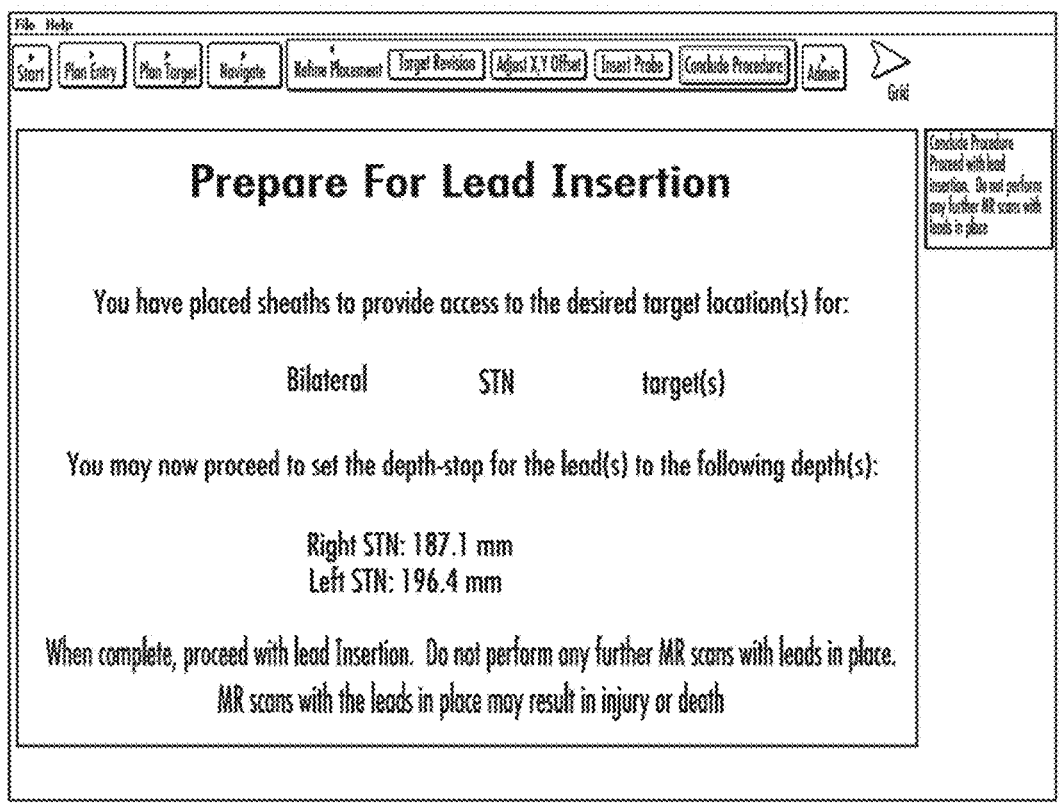

FIG. 36 illustrates the Refine Placement workflow group with the "conclude procedure" step selected. This step occurs after all probes have been inserted and have had their positions verified by the physician. At this point, the UI can prompt them to insert both leads where implantable stimulation leads are to be placed (using the defined trajectory) and can warn them not to perform any additional scans if MRI-incompatible or potentially incompatible leads are used. As shown, the system 10 can be configured to define (and output to a user) or depth stops to set the lead or other therapy or diagnostic device for each STN or target site. The depth stops can be different for each implant location on the left and right targets (for bilateral procedures) so that the electrodes of the leads or other components for other devices are positioned in the desired location.

Figure 37:
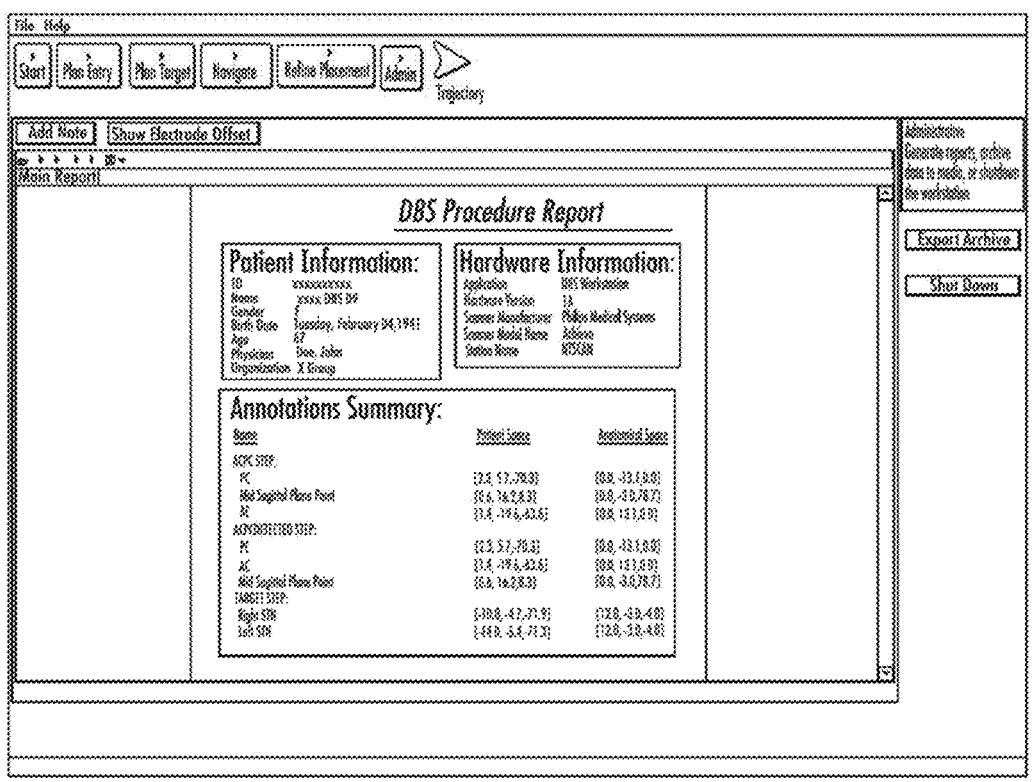

FIG. 37 illustrates an example of a display that may be used for the ADMIN workflow group. This group has one step that provides reporting and archive functionality. The report automatically documents the entire procedure including annotations, measurements, and screen captures. The circuit 30*c* can generate a full version and an anonymous version of the report and may include a date as to when everything is archived to CD.

The circuit 30*c* may also be configured to determine where individual electrodes on the DBS leads are situated in ACPC coordinates. Given the tip position in MR coordinates (the circuit 30*c* can ill in the planned position, but the user may change it) the user will provide a set of offset values that represent the distance of each electrode from the lead tip. In other embodiments, a lead type can be selected such as from a pull-down list and those values can automatically be input based on the manufacturer and lead type (e.g., design thereof). The circuit 30*c* can be configured so that the UI displays the corresponding electrode positions in ACPC coordinates.

Figure 38:
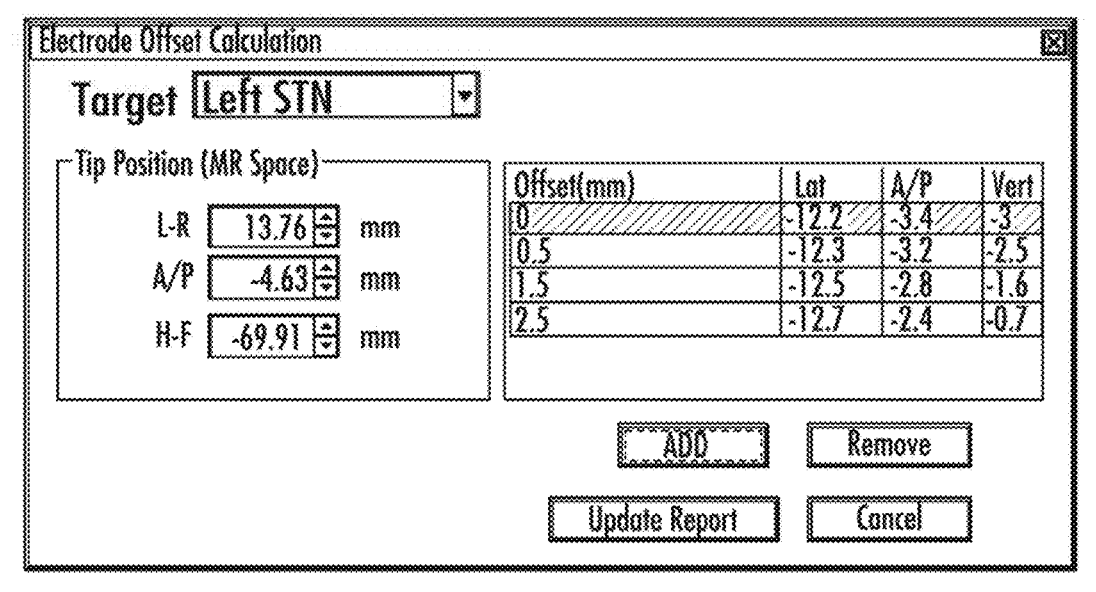

FIG. 38 illustrates an example of a display with a UI that may be used for the ADMIN workflow group shown as— Admin Page/Electrode Offset dialog step selected. This step may also be included in the Conclude Procedure/step or provided as a separate workflow group. The electrode offset values may significantly speed up the process by which the pulse generator is programmed since the physician will know where the electrodes are anatomically.

The system 10 may also include a decoupling/tuning circuit that allows the system to cooperate with an MRI scanner 20 and filters and the like. See, e.g., U.S. Pat. Nos. 6,701,176; 6,904,307 and U.S. Patent Application Publication No. 2003/0050557, the contents of which are hereby incorporated by reference as if recited in full herein. As noted above, one or more of the tools can include an intrabody MRI antenna 50*a* (FIG. 5) that is configured to pick-up MRI signals in local tissue during an MRI procedure. The MRI antenna can be configured to reside on the distal portion of the probe. In some embodiments, the antenna has a focal length or signal-receiving length of between about 1-5 cm, and typically is configured to have a viewing length to receive MRI signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928, 145; 6,263,229; 6,606,513; 6,628,980; 6,284,971; 6,675, 033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein.

In some embodiments, the implanted leads and/or intrabody tools can be configured to allow for safe MRI operation so as to reduce the likelihood of undesired deposition of current or voltage in tissue. The leads or tools can include RF chokes such as a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current. The conductors connecting electrodes or other components on or in the tools can also include a series of back and forth segments (e.g., the lead can turn on itself in a lengthwise direction a number of times along its length) and/or include high impedance circuits. See, e.g., U.S. patent application Ser. Nos. 11/417,594; 12/047,602; and Ser. No. 12/090,583, the contents of which are hereby incorporated by reference as if recited in full herein.

Although not shown, in some embodiments, one or more of the surgical tools can be configured with one or more lumens and exit ports that deliver desired cellular, biological, and/or drug therapeutics to the target area, such as the brain. The tools may also incorporate transseptal needles, biopsy and/or injection needles as well as ablation means. The lumens, where used, may receive extendable needles that may exit the probe from the distal end or from the sides, proximal, distal, or even, through the electrodes to precisely deliver cellular/biological therapeutics to the desired anatomy target. This delivery configuration may be a potential way to treat patients, where the cellular/biological therapeutics can be delivered into the desired anatomy to modify their cellular function. The cells (e.g., stem cells) may improve function. MRI can typically be effectively used to monitor the efficacy and/or delivery of the therapy.

Figure 39:
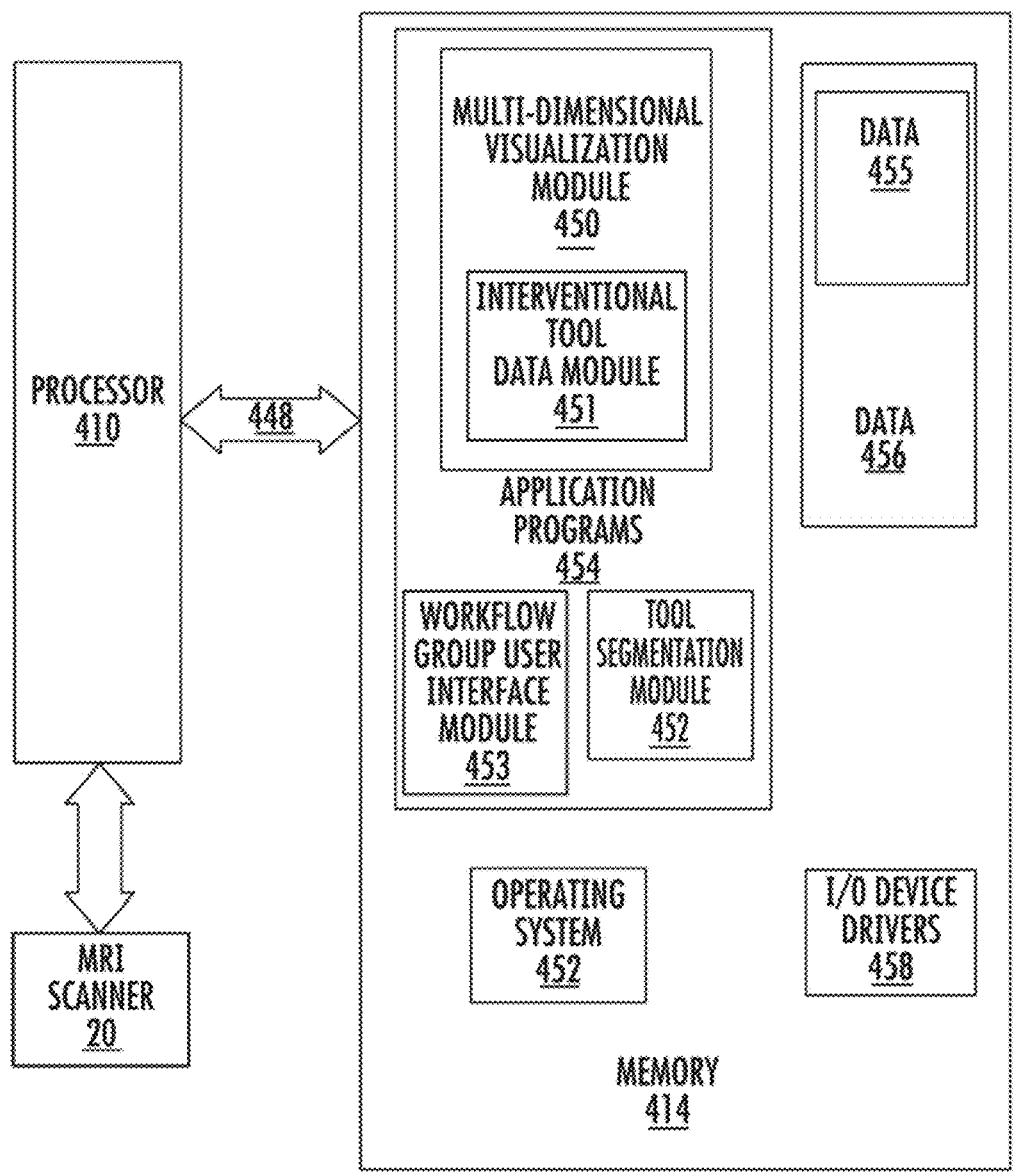
FIG. 39 is a data processing system according to some embodiments of the present invention.

The system 10 can include circuits and/or modules that can comprise computer program code used to automatically or semi-automatically carry out operations to generate visualizations and provide output to a user to facilitate MRI-guided diagnostic and therapy procedures. FIG. 39 is a schematic illustration of a circuit or data processing system that can be used with the system 10. The circuits and/or data processing systems may be incorporated in one or more digital signal processors in any suitable device or devices. As shown in FIG. 39, the processor 410 communicates with an MRI scanner 20 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

As shown in FIG. 39 illustrates that the memory 414 may include several categories of software and data used in the data processing system: the operating system 452; the application programs 454; the input/output (I/O) device drivers 458; and data 456. The data 456 can also include predefined characteristics of different surgical tools and patient image data 455. FIG. 39 also illustrates the application programs 454 can include a Visualization Module 450, Interventional Tool Data Module 451, a Tool Segmentation Module 452 (such as segmentation modules for a grid patch, a targeting canula, and a trajectory guide frame and/or base), and a workflow group User Interface Module 453 (that facilitates user actions and provides guidance to obtain a desired trajectory such as physical adjustments to achieve same).

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components. The application programs 454 are illustrative of the programs that implement the various features of the data processing system and can include at least one application, which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the Modules 450-453 being application programs in FIG. 39, as will be appreciated by those of skill in the art, other configurations may also be utilized while still benefiting from the teachings of the present invention. For example, the Modules 450-453 and/or may also be incorporated into the operating system 452, the I/O device drivers 458 or other such logical division of the data processing system. Thus, the present invention should not be construed as limited to the configuration of FIG. 39 which is intended to encompass any configuration capable of carrying out the operations described herein. Further, one or more of modules, i.e., Modules 450-453 can communicate with or be incorporated totally or partially in other components, such as a workstation, an MRI scanner, an interface device. Typically, the workstation 30 will include the modules 450-453 and the MR scanner with include a module that communicates with the workstation 30 and can push image data thereto.

The I/O data port can be used to transfer information between the data processing system, the circuit 30c or workstation 30, the MRI scanner 20, and another computer system or a network (e.g., the Internet) or to other devices controlled by or in communication with the processor. These components may be conventional components such as those used in many conventional data processing systems, which may be configured in accordance with the present invention to operate as described herein.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. More particularly, the workflow steps may be carried out in a different manner, in a different order and/or with other workflow steps or may omit some or replace some workflow steps with other steps. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A computer program product for facilitating an MRI-guided surgical procedure, the computer program product comprising:
a non-transitory computer readable storage medium having computer readable program code embodied in the medium, the computer-readable program code comprising:
computer readable program code that comprises predefined physical data of a plurality of different surgical tools;
computer readable program code that obtains MR image data of a patient;
computer readable program code that generates multi-dimensional visualizations using the predefined physical data of the different surgical tools and data from the obtained MR images of the patient in substantially real time during the MRI-guided surgical procedure; and
computer readable program code that provides a User Interface to a display that defines workflow progression for the MRI-guided surgical procedure and allows a user to select steps in the workflow,
wherein the computer readable program code that comprises predefined physical data of a plurality of different surgical tools includes computer readable program code associated with a trajectory guide as one of the surgical tools, the trajectory guide comprising fiducial markers in a fixed geometric relationship, the trajectory guide configured to define a trajectory path for a subsurface brain target in the patient, the trajectory guide having a base that affixes to a patient's skull,
wherein the computer program product further comprises computer readable program code that segments the obtained MR image data including computer readable program code that segments the obtained MR image data to locate the fiducial markers of the trajectory guide and identify an orientation of the trajectory guide.

2. The computer program product of claim 1, wherein the computer readable program code that obtains MR image data of the patient is configured to obtain MR image data of patient function, and wherein the computer readable program code that generates the visualizations also shows patient function including active regions in a brain of the patient based on fMRI and/or patient stimulation.

3. The computer program product of claim 1, further comprising computer readable program code that selectively displays brain fiber tracks of the patient in at least some of the visualizations on at least one display.

4. The computer program product of claim 1,
wherein the computer readable program code that segments the image data is configured to segment the image data while the patient is in a high-magnetic field of an MRI scanner using the predefined physical data,
wherein the predefined physical data comprises predefined physical characteristics of a flexible grid attached to a skull of the patient; and
computer readable program code that deforms an electronic model of the grid to fit a head surface of the patient and identify associated vertices.

5. The computer program product of claim 1, wherein the computer readable program code that provides the User Interface that defines workflow progression for the MRI-guided surgical procedure comprises a series of selectable workflow groups including "start", "plan entry", "plan target", "navigate", and "refine" that is used to guide the MRI-guided surgical procedure resulting in delivering a therapy after the "refine" workflow group.

6. The computer program product of claim 5, wherein the computer readable program code that provides the User Interface also provides a "bilateral" selection option.

7. The computer program product of claim 5, wherein the computer readable program code that provides the User Interface also includes an "Administrative" workflow group that electronically generates a medical report automatically summarizing clinical information regarding the patient and certain surgical information including at least a plurality of the following:
(a) AC, PC, and MSP points in MR space (both detected and user-specified, if user modified);
(b) planned and corrected targets in both MR and ACPC space;
(c) elapsed time for the procedure; and
(d) screenshots taken during the procedure.

8. The computer program product of claim 1, wherein the computer readable program code that provides the User Interface further comprises computer readable program code that allows a user to select different intrabody procedures including a unilateral or bilateral procedure and a desired intrabody target, then, if a bilateral procedure is selected, the computer readable program code provides a toolbar with left and right workflow steps.

9. The computer program product of claim 1, further comprising computer readable program code that generates a different workflow group when a bilateral option is selected so as to display workflow steps that guides a user to complete grid entry locations for both bilateral sides, hole formation for both sides and trajectory frame attachment to both sides before proceeding to a "plan target" step due to brain shift and before directing a patient to be returned to an imaging location.

10. The computer program product of claim 1, further comprising:
computer readable program code that presents on a display, a user-selectable trajectory line to a deep brain location that intersects a flexible grid on a patient's skull and defines a location on the grid for marking a burr entry hole based on the desired trajectory line; and
computer readable program code that generates an audible and/or visual warning when a user selects a trajectory line that does not intersect the grid.

11. The computer program product of claim 1, further comprising computer readable program code that accepts input of an identifier associated with the tools and blocks use of a surgical system if the identifier indicates that it is not an authorized tool or that the at least one tool has a version that is not compatible with the surgical system.

12. The computer program product of claim 1, further comprising:
computer readable program code configured to analyze data regarding a bore size of a scanner being used for the MRI-guided surgical procedure of the patient;
computer readable program code configured to monitor for a physical limitation or interference of a surgical tool based on: (a) pre-defined physical characteristics of the surgical tool; (b) scanner bore size; and (c) patient size; and
computer readable program code configured to generate an audible or visual warning or an audible and visual warning when one or more of the surgical tools will be blocked by physical interference with a wall defining at least a portion of the bore size of the scanner.

13. The computer program product of claim 1, further comprising:
computer readable program code that identifies a position and orientation of a flexible patch as one of the surgical tools based on predefined physical characteristics of the patch, the patch comprising a grid and is adapted to reside on the patient;
computer readable program code that deforms an electronic model of the patch to fit curvature of a skull of the patient; and
computer readable program code that displays a visual overlay of the deformed electronic model of the patch on the skull of the patient on at least one display.

14. The computer program product of claim 1, further comprising computer readable program code that:
segments the image data while the patient is in a high-magnetic field of an MRI scanner using predefined physical characteristics of a flexible patch with a grid attached to a skull of the patient and of a trajectory guide as two of the surgical tools with the predefined physical data;
deforms an electronic model of the flexible patch with the grid to fit a head surface of the patient and identify associated vertices;
calculates user adjustments to move at least one of a pitch, roll, X or Y actuator to adjust a trajectory of a trajectory guide to provide a desired intrabody trajectory to a target site; and
displays the calculated user adjustments to at least one display associated with an MRI suite to thereby provide a user with adjustment data regarding actuator adjustment for at least one of a pitch, roll, X or Y actuator of the trajectory guide to achieve the desired intrabody trajectory thereby facilitating an MRI-guided surgical procedure.

15. The computer program product of claim 1, wherein the predefined physical data comprises predefined characteristics of a flexible patch as one of the surgical tools, wherein the generated visualizations include a visualization presented on a display which shows the flexible patch as an overlay on the patient with defined grid coordinates for a surgical entry site.

16. The computer program product of claim 1, wherein the computer readable program code that provides the User Interface on a display is configured to allow a user to select a bilateral procedure, and in response thereto, the User Interface displays workflow steps that guides a user to complete grid entry locations for two sides of a brain, hole formation for both sides and trajectory frame attachment to both sides before proceeding to a "plan target" step due to brain shift and before directing a patient to be returned to an imaging location in a bore of a magnet of an MRI scanner.

17. The computer program product of claim 1, wherein the computer readable program code that comprises predefined physical data of a plurality of different surgical tools includes an imaging probe with an intrabody antenna as one of the different surgical tools, the imaging probe configured to collect small field, high-resolution image data, and wherein the computer program product further comprises computer readable program code that is configured to electronically apply a correction to reduce intensity distortion associated with image data collected from the imaging probe.

18. The computer program product of claim 1, wherein the trajectory guide fiducial markers are circumferentially spaced apart and positioned relative to each other such that at least two are closer together than another to define an affirmative orientation of the trajectory guide.

19. The computer program product of claim 18, wherein the fiducial markers comprise three fluid-filled annular fiducial markers.

20. The computer program product of claim 1, further comprising computer readable program code that generates color coded electroanatomical visualizations of target anatomy in substantially real-time as at least some of the generated visualizations, using at least one of:
    (a) electrical signals obtained from electrodes associated with one or more of the surgical tools, correlated to time and position of the electrodes to render visualizations to illustrate neural electrical potentials and locations; or
    (b) patient functional data including fMRI data or MRI image data or fMRI and MRI image data showing electrical activity in response to a stimulation.

21. The computer program product of claim 1, wherein the generated visualizations comprise a spatially encoded position and orientation of a tool of the plurality of different surgical tools.

* * * * *